United States Patent [19]

Ressemann et al.

[11] Patent Number: 5,897,567
[45] Date of Patent: Apr. 27, 1999

[54] EXPANDABLE INTRAVASCULAR OCCLUSION MATERIAL REMOVAL DEVICES AND METHODS OF USE

[75] Inventors: Thomas V. Ressemann, St. Cloud; Anthony C. Vrba; Steven S. Hackett, both of Maple Grove; Chad J. Kugler, Spring Lake Park; Hans A. Mische, St. Cloud, all of Minn.

[73] Assignee: SciMed Life Systems, Inc., Maple Grove, Minn.

[21] Appl. No.: 08/924,850

[22] Filed: Sep. 9, 1997

Related U.S. Application Data

[63] Continuation of application No. 08/621,350, Mar. 25, 1996, abandoned, which is a continuation-in-part of application No. 08/206,053, Mar. 3, 1994, Pat. No. 5,501,694, and application No. 08/261,813, Jun. 17, 1994, Pat. No. 5,540,707, which is a continuation-in-part of application No. 08/055,995, Apr. 29, 1993, Pat. No. 5,490,859, said application No. 08/206,053, is a continuation-in-part of application No. 08/055,995.

[51] Int. Cl.$^6$ ..................................................... A61B 17/32
[52] U.S. Cl. .............................. 606/159; 606/170; 604/22
[58] Field of Search ................................. 606/1, 159, 170, 606/180, 171; 604/22

[56] References Cited

U.S. PATENT DOCUMENTS

| | | |
|---|---|---|
| 1,112,982 | 10/1914 | Conine . |
| 1,612,697 | 12/1926 | Cecil . |
| 2,498,692 | 2/1950 | Mains . |
| 2,621,651 | 12/1952 | Wallace . |
| 2,816,552 | 12/1957 | Hoffman . |

(List continued on next page.)

FOREIGN PATENT DOCUMENTS

| | | |
|---|---|---|
| 0 117 519 A1 | 2/1984 | European Pat. Off. . |
| 0 254 414 A1 | 6/1987 | European Pat. Off. . |
| 0 335 861 B1 | 10/1989 | European Pat. Off. . |
| 0 533 321 A2 | 3/1993 | European Pat. Off. . |
| BD 867144 | 12/1952 | Germany . |
| 2 020 557 | 11/1979 | United Kingdom . |
| WO 83/03752 | 11/1983 | WIPO . |
| WO 91/17714 | 11/1991 | WIPO . |
| WO 92/03097 | 3/1992 | WIPO . |
| WO 92/03098 | 3/1992 | WIPO . |
| WO 93/01753 | 2/1993 | WIPO . |
| WO 93/01849 | 2/1993 | WIPO . |
| WO 93/19679 | 10/1993 | WIPO . |

OTHER PUBLICATIONS

Technical Bulletin P.B.S. vs. Electroplating Abrasive Technology, Inc. from Manufacturers of Diamond and CBN Products for Industry.

Percutaneous Aspiration Thromboembolectomy, Interventional Radiology, Jul. 1985, 156:61–66.

(List continued on next page.)

*Primary Examiner*—Michael Buiz
*Assistant Examiner*—William W. Lewis
*Attorney, Agent, or Firm*—Crompton, Seager & Tufte, LLC

[57] ABSTRACT

An improved expandable removal element (16) for an atherectomy device wherein the expandable removal element (16) is movable between an expanded position and a contracted position. In one embodiment of the present invention, a single drive shaft (92) is operatively connected to the distal end of the expandable material removal element (16) for rotating the removal element (16). A catheter (178) may surround a portion of the drive shaft (92). The catheter (178) is shiftable with respect to the drive shaft (92) for moving the material removal element between the expanded position and the contracted position. In another embodiment of the present invention, dual coaxial drive shafts are employed. The inner drive shaft (312) and the outer drive (314) are shiftable with respect to one another for moving the removal element (252) between the expanded position and the contracted position. The present invention also describes several embodiments for an improved removal element (252).

12 Claims, 18 Drawing Sheets

U.S. PATENT DOCUMENTS

| | | |
|---|---|---|
| 3,352,303 | 11/1967 | Delaney . |
| 3,416,531 | 12/1968 | Edwards . |
| 3,433,226 | 3/1969 | Boyd . |
| 3,485,234 | 12/1969 | Stevens . |
| 3,568,659 | 3/1971 | Karnegis . |
| 3,605,725 | 9/1971 | Bentov . |
| 3,623,483 | 11/1971 | Dyer, Jr. . |
| 3,692,029 | 9/1972 | Adair . |
| 3,773,034 | 11/1973 | Burns et al. . |
| 3,788,318 | 1/1974 | Kim et al. . |
| 3,789,852 | 2/1974 | Kim et al. . |
| 3,868,956 | 3/1975 | Alfidi et al. . |
| 3,894,673 | 7/1975 | Lowder et al. . |
| 3,923,065 | 12/1975 | Nozick et al. . |
| 3,965,909 | 6/1976 | Waddell et al. . |
| 3,968,800 | 7/1976 | Vilasi . |
| 3,996,938 | 12/1976 | Clark, III . |
| 4,018,576 | 4/1977 | Lowder et al. . |
| 4,046,150 | 9/1977 | Schwartz et al. . |
| 4,137,906 | 2/1979 | Akiyama et al. . |
| 4,177,815 | 12/1979 | Patel . |
| 4,195,637 | 4/1980 | Grüntzig et al. . |
| 4,273,128 | 6/1981 | Lary . |
| 4,307,722 | 12/1981 | Evans . |
| 4,323,071 | 4/1982 | Simpson et al. . |
| 4,347,846 | 9/1982 | Dormia . |
| 4,445,509 | 5/1984 | Auth . |
| 4,465,072 | 8/1984 | Taheri . |
| 4,572,186 | 2/1986 | Gould et al. . |
| 4,577,631 | 3/1986 | Kreamer . |
| 4,607,618 | 8/1986 | Angelchik . |
| 4,650,466 | 3/1987 | Luther . |
| 4,679,557 | 7/1987 | Opie et al. . |
| 4,696,667 | 9/1987 | Masch . |
| 4,732,154 | 3/1988 | Shiber . |
| 4,771,774 | 9/1988 | Simpson et al. . |
| 4,784,636 | 11/1988 | Rydell . |
| 4,819,634 | 4/1989 | Shiber . |
| 4,838,853 | 6/1989 | Parisi . |
| 4,842,579 | 6/1989 | Shiber . |
| 4,883,458 | 11/1989 | Shiber . |
| 4,885,003 | 12/1989 | Hillstead . |
| 4,886,061 | 12/1989 | Fischell et al. . |
| 4,886,490 | 12/1989 | Shiber . |
| 4,894,051 | 1/1990 | Shiber . |
| 4,895,166 | 1/1990 | Farr et al. . |
| 4,895,560 | 1/1990 | Papantonakos . |
| 4,921,484 | 5/1990 | Hillstead . |
| 4,957,482 | 9/1990 | Shiber . |
| 4,966,604 | 10/1990 | Reiss . |
| 4,979,939 | 12/1990 | Shiber . |
| 4,990,134 | 2/1991 | Auth . |
| 5,002,553 | 3/1991 | Shiber . |
| 5,007,896 | 4/1991 | Shiber . |
| 5,009,659 | 4/1991 | Hamlin et al. . |
| 5,011,488 | 4/1991 | Ginsburg . |
| 5,024,651 | 6/1991 | Shiber . |
| 5,030,201 | 7/1991 | Palestrant . |
| 5,034,001 | 7/1991 | Garrison et al. . |
| 5,041,082 | 8/1991 | Shiber . |
| 5,100,425 | 3/1992 | Fischell et al. . |
| 5,116,350 | 5/1992 | Stevens . |
| 5,135,483 | 8/1992 | Wagner et al. . |
| 5,135,531 | 8/1992 | Shiber . |
| 5,154,724 | 10/1992 | Andrews . |
| 5,176,693 | 1/1993 | Pannek, Jr. . |
| 5,217,474 | 6/1993 | Zacca et al. . |
| 5,224,945 | 7/1993 | Pannek, Jr. . |
| 5,250,060 | 10/1993 | Carbo et al. . |
| 5,314,407 | 5/1994 | Auth et al. . |
| 5,314,438 | 5/1994 | Shturman . |
| 5,490,859 | 2/1996 | Mische et al. . |
| 5,501,694 | 3/1996 | Ressemann et al. . |
| 5,507,292 | 4/1996 | Jang et al. ............................ 606/159 |
| 5,540,707 | 7/1996 | Ressemann et al. . |

OTHER PUBLICATIONS

Mechanical Spiral Embolectomy Catheter, Irvin F. Hawkins, Jr., M.D., et al., Seminars in Interventional Radiology, vol. 2, No. 4, Dec. 1985, pp. 414–418.

PAT–RAT Acc. to "Starck"–Rotational Aspiration Thromboembolectomy, Angiomed.

Pecutaneous Embolectomy by Transcatheter Aspiration, Kenneth W. Sniderman, M.D., et al., Radiology, Feb. 1984 150:357–361.

Percutaneous Transluminal Thrombus Aspiration, E. Starck et al., Angiographic Management of Vascular Obstruction, pp. 625–632.

Advantages of Percutaneous Aspiration Thromboembolectomy, E. Starck et al., pp. 241–247.

Mechanical Thrombectomy, S. Murthy Tadavarthy, M.D., Interventional Radiology, vol. 1, Second Edition, pp. 635–664.

Transvenous Removal of Pulmonary Emboli by Vacuum–Cup Catheter Technique, Lazar J. Greenfield, M.D., Journal of Surgical Research, vol. 9, No. 6, Jun. 1969, pp. 347–352.

Balloon Embolectomy Catheter Used Percutaneously, John c. McDermott, M.D., Radiology, vol. 160, No. 1., p. 279.

Correspondence and Brief Communication/Calendar of Events, Arch Surg—vol. 120, Jan. 1985, p. 116.

Percutaneous Aspiration Thromboembolectomy (PAT): An Alternative to Surgical Balloon Techniques for Clot Retrieval, William D. Turnipseed, M.D., et al., Journal of Vascular Surgery, vol. 3, No. 3, Mar. 1986, pp. 437–441.

Peripheral Percutaneous Aspiration Thrombectomy and Angioplasty Following Failed Lytic Therapy for Acute Popliteal Artery Occlusion, George Li, M.D., Journal of Interventional Cardiology, vol. 5, No. 3, 1992, pp. 159–162.

The Roto–Drill, A New Instrument for Thromboendarterectomy, Shafiroff et al., 1961, pp. 316–319.

Percutaneous Embolectomy by Transcatheter Aspiration, Kenneth W. Sniderman, M.D. et al., Radiology, vol. 150, No. 2., pp. 357–361.

Pecutaneous Aspiration Thromboembolectomy, Erhard E. Starck, M.D. et al., Radiology, vol. 156, No. 1., pp. 61–66.

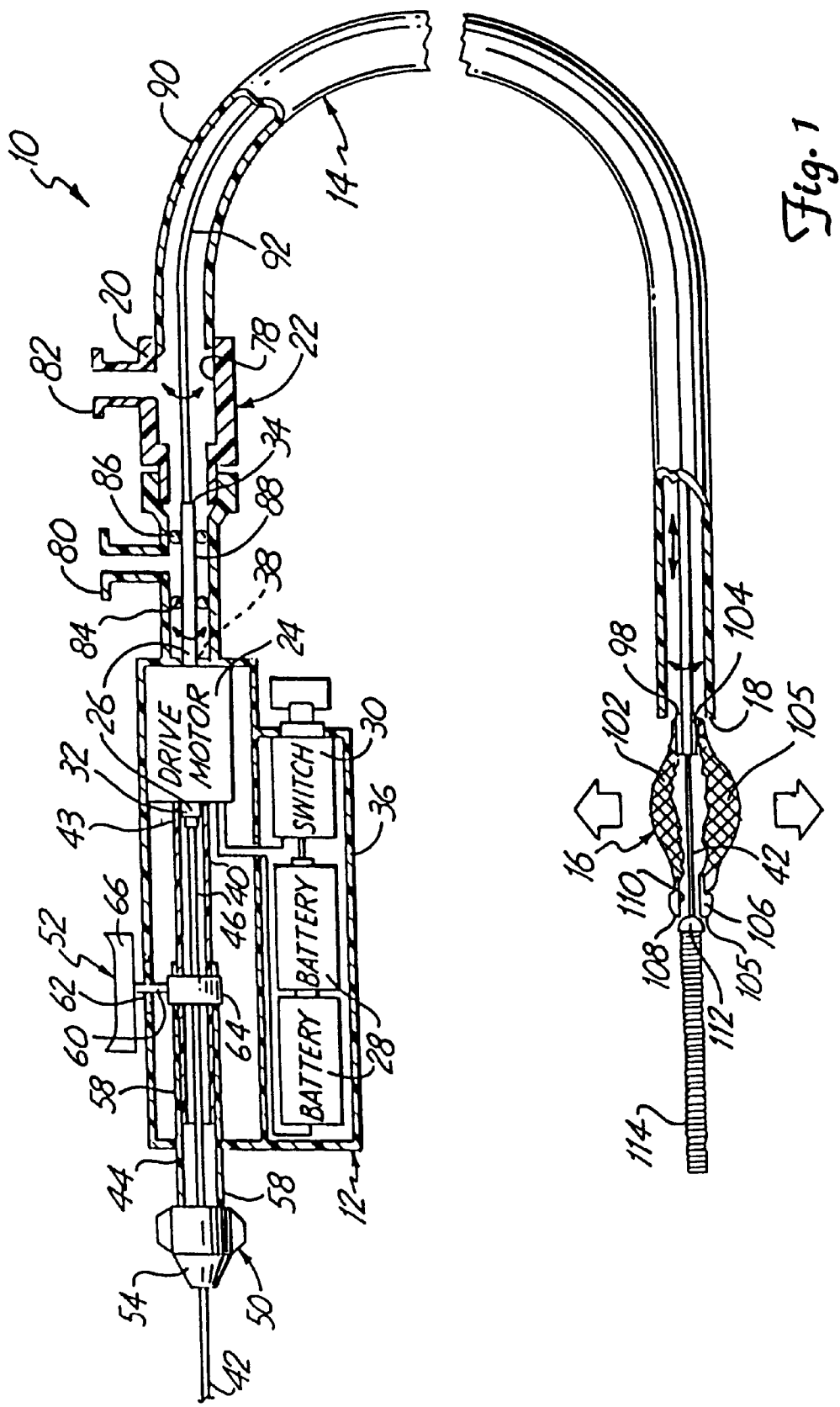

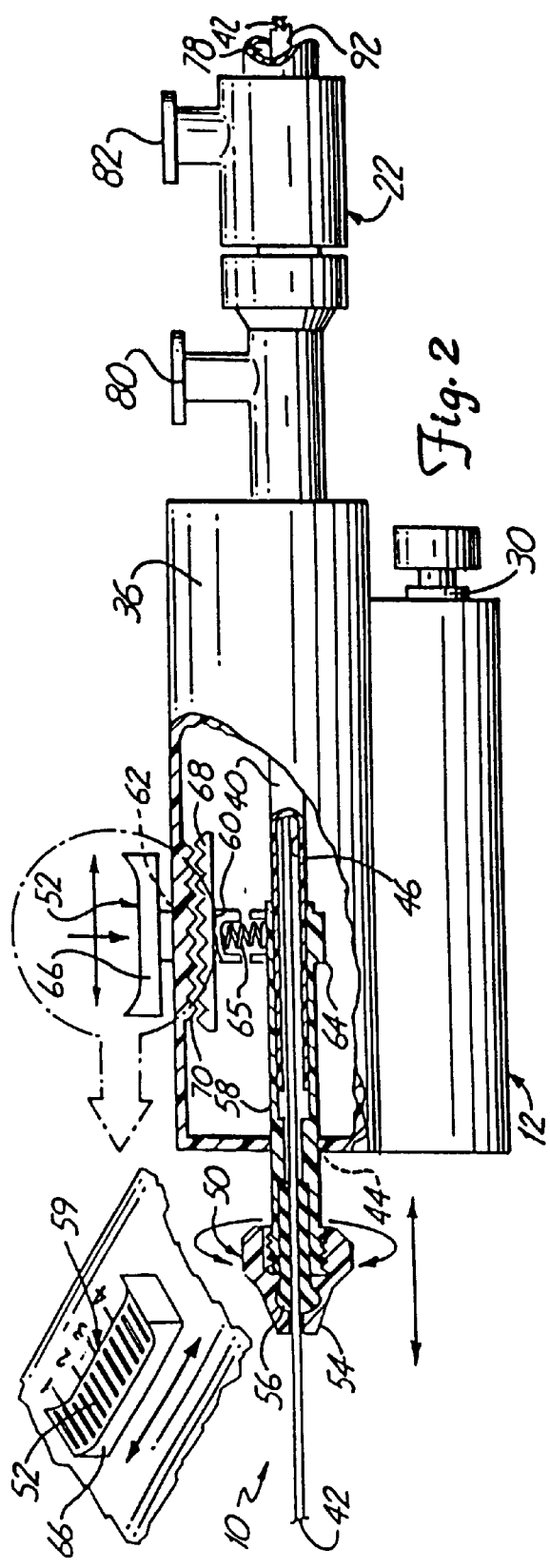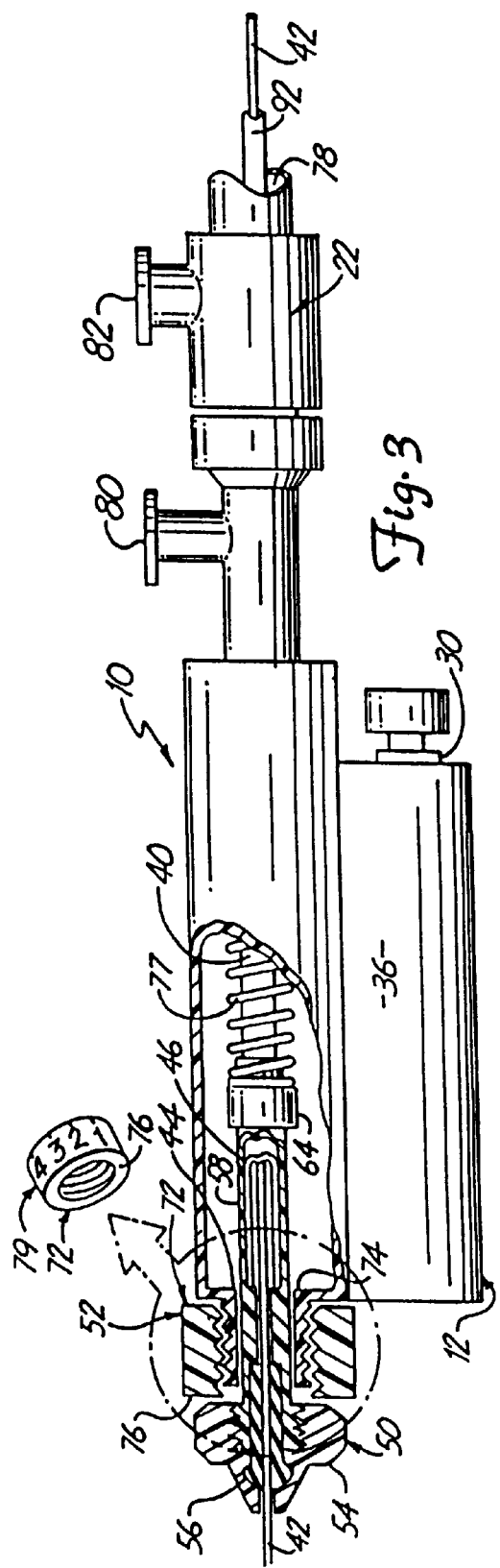

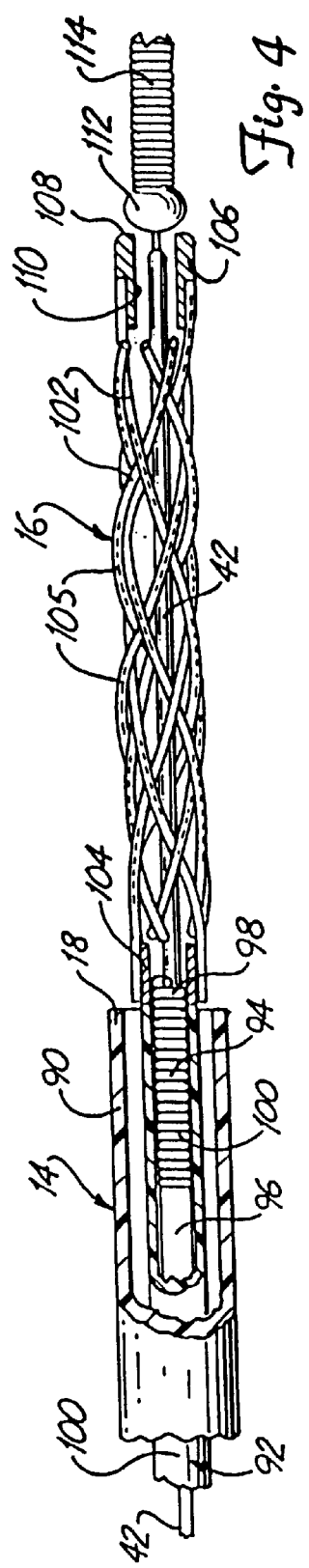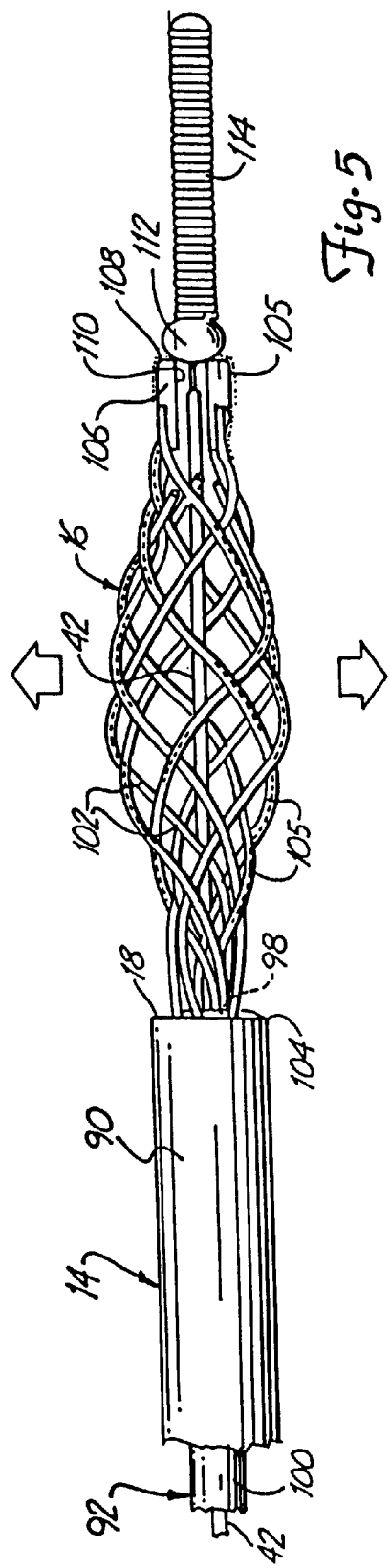

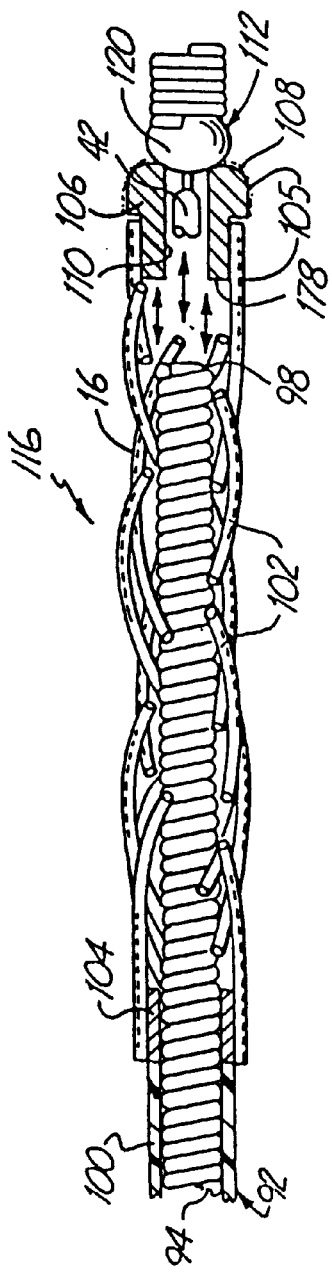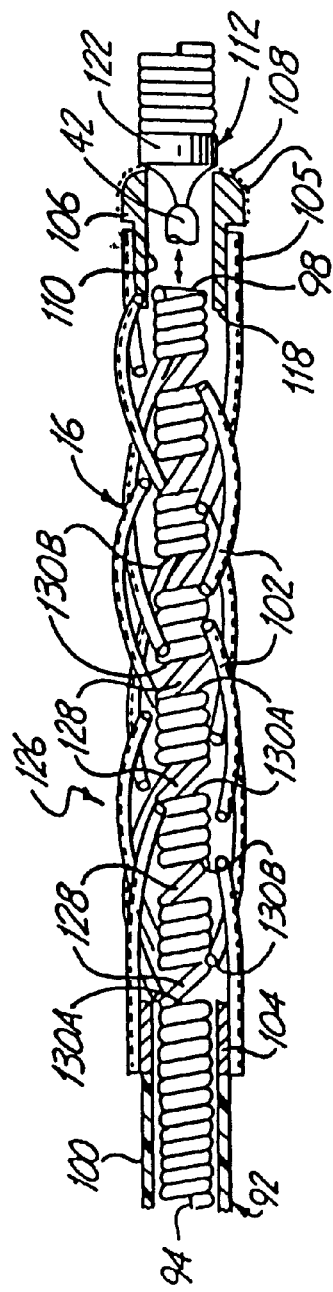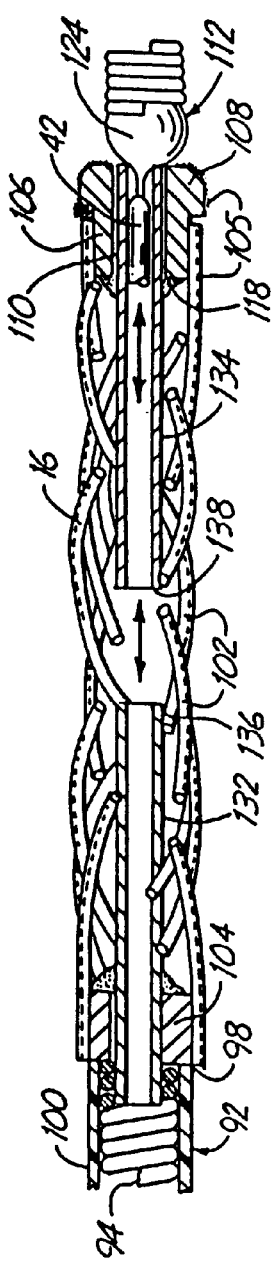

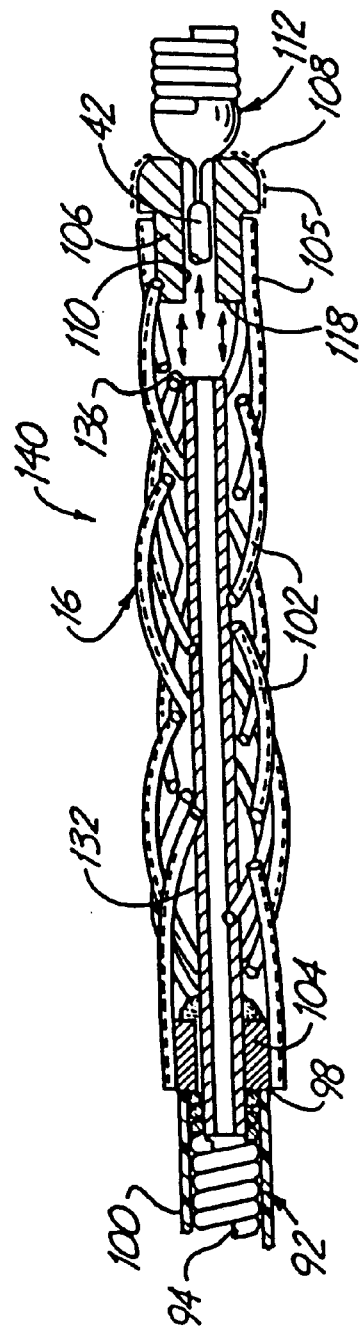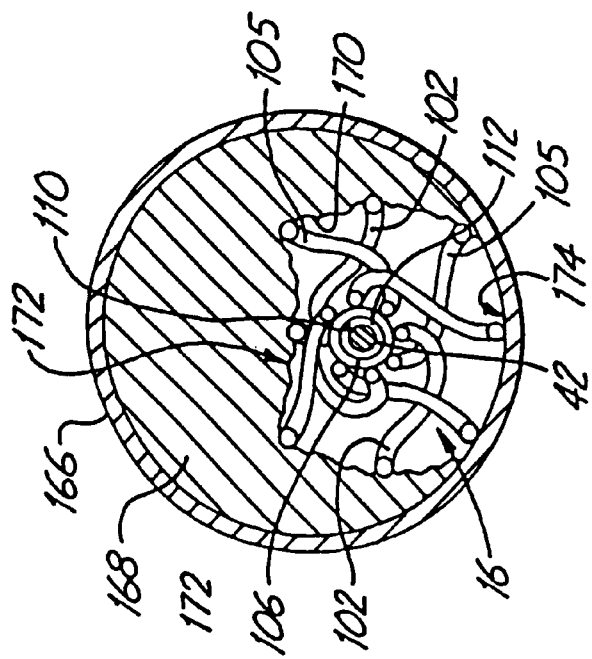

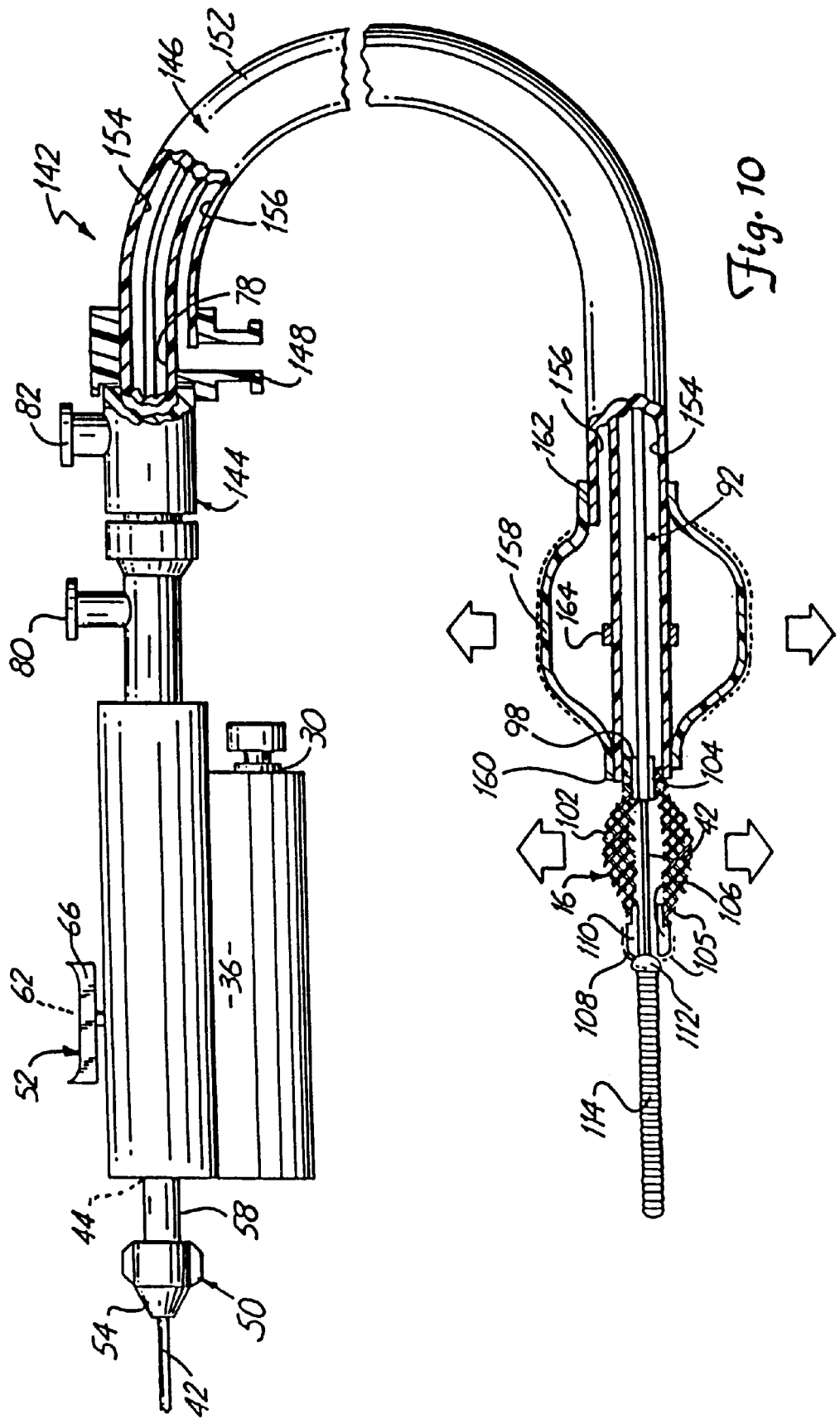

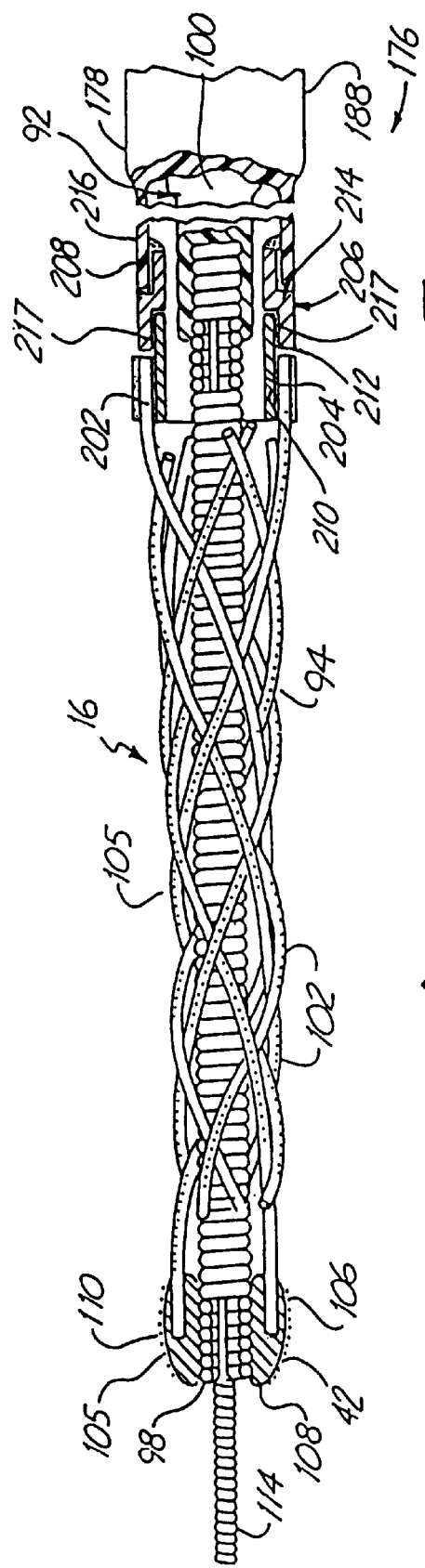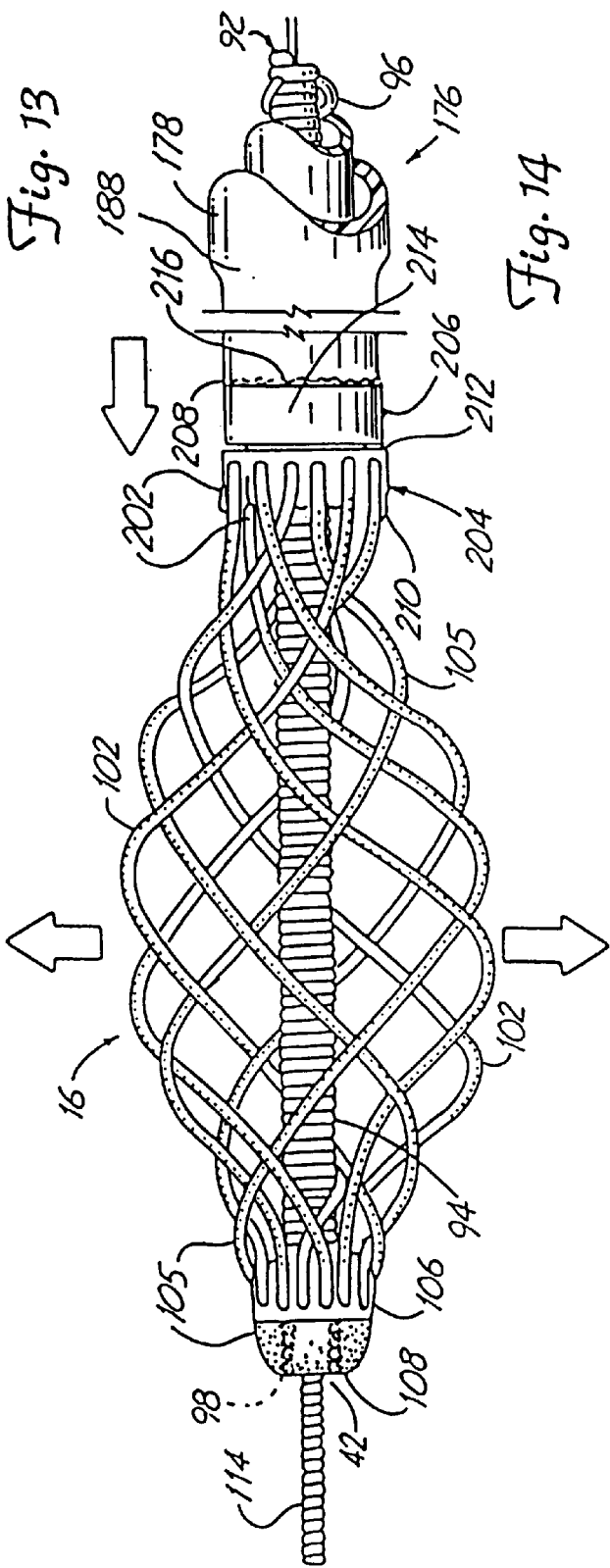

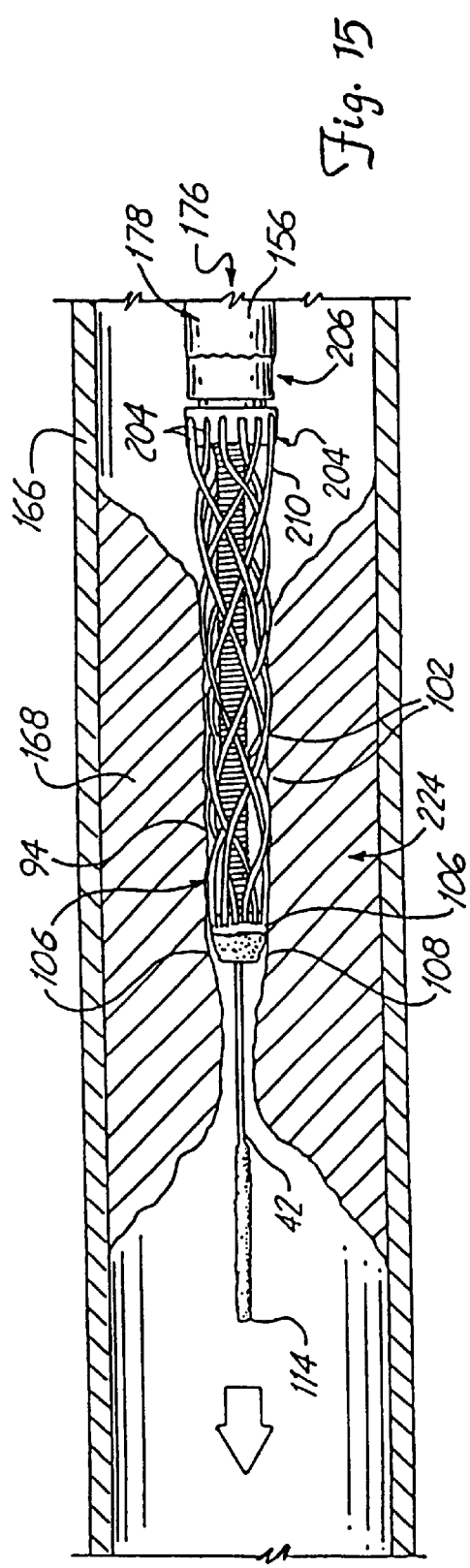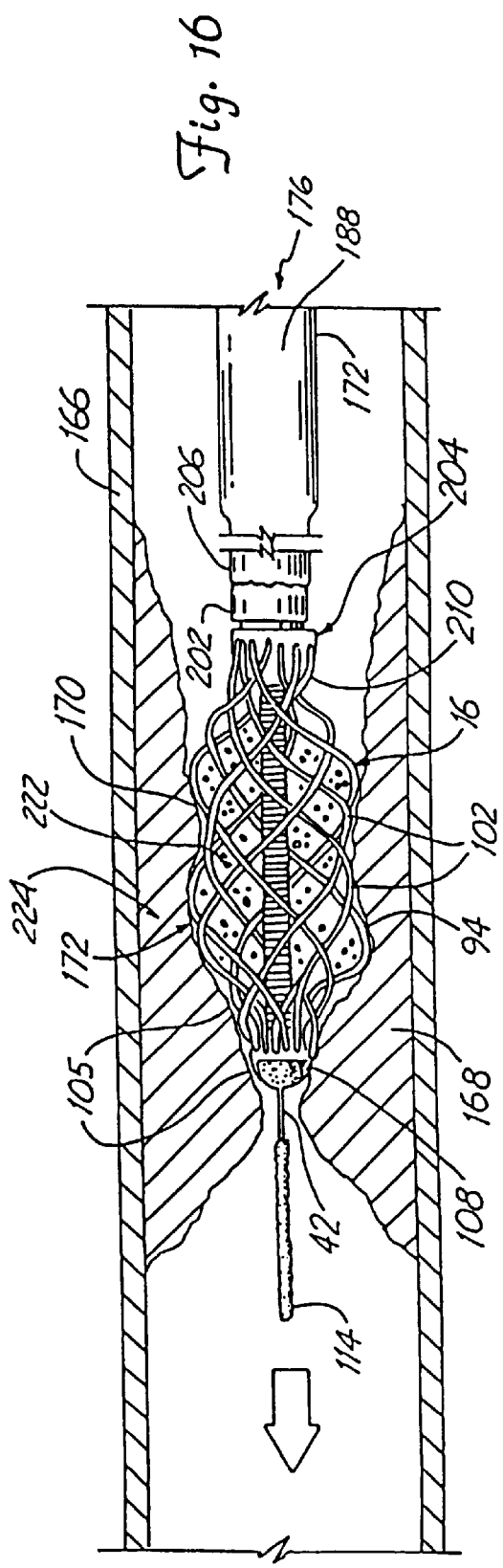

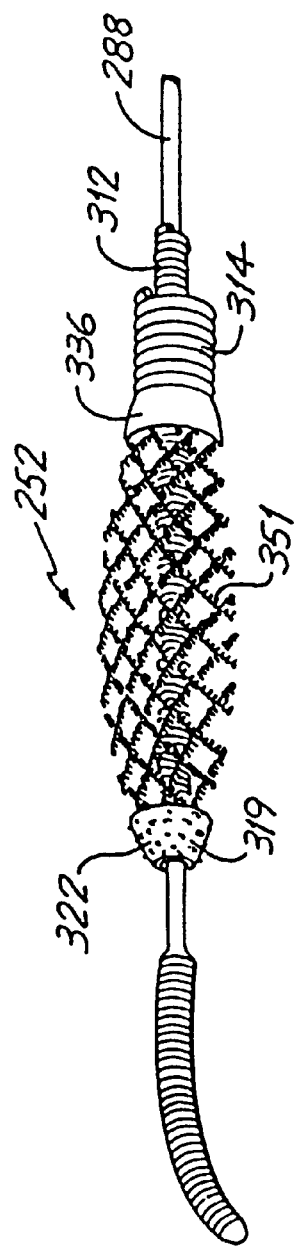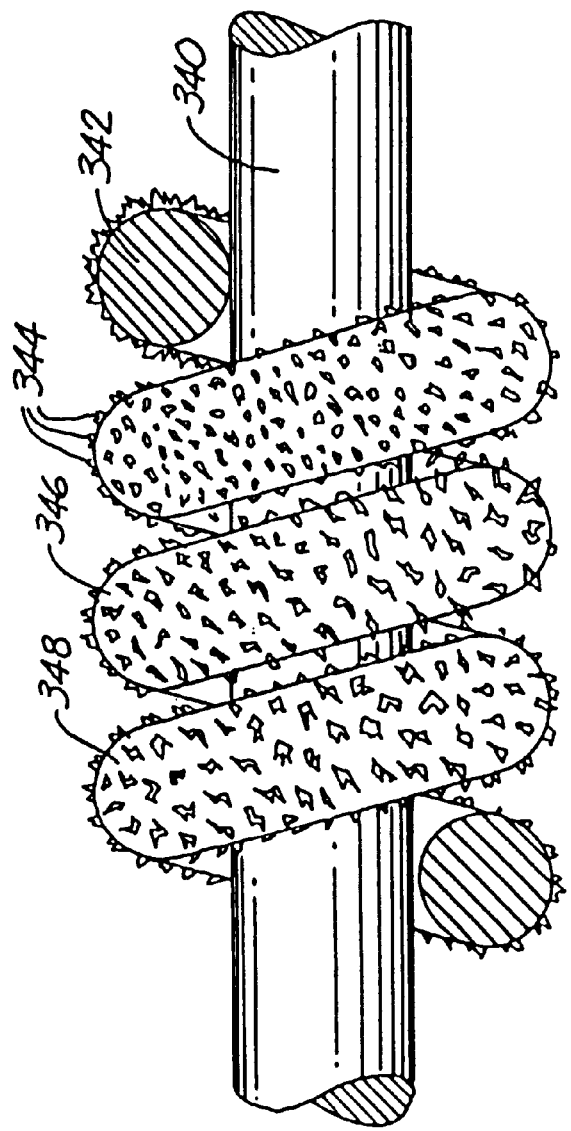

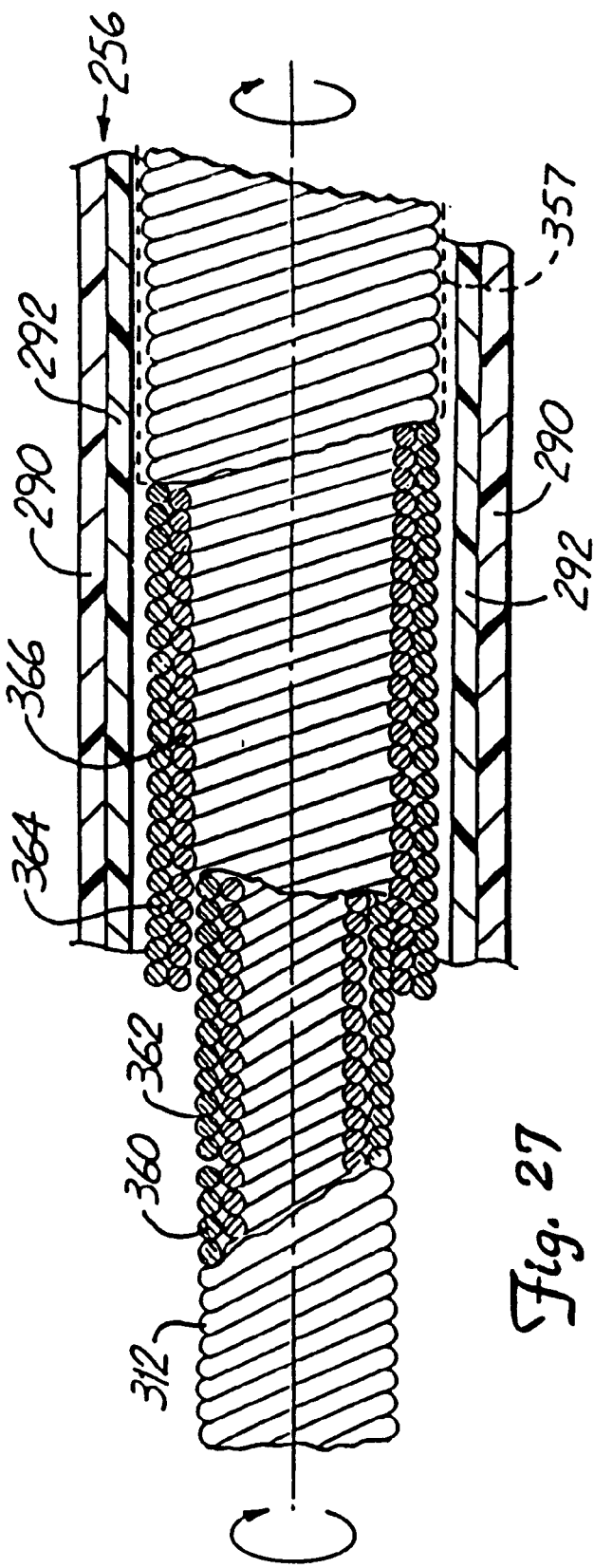
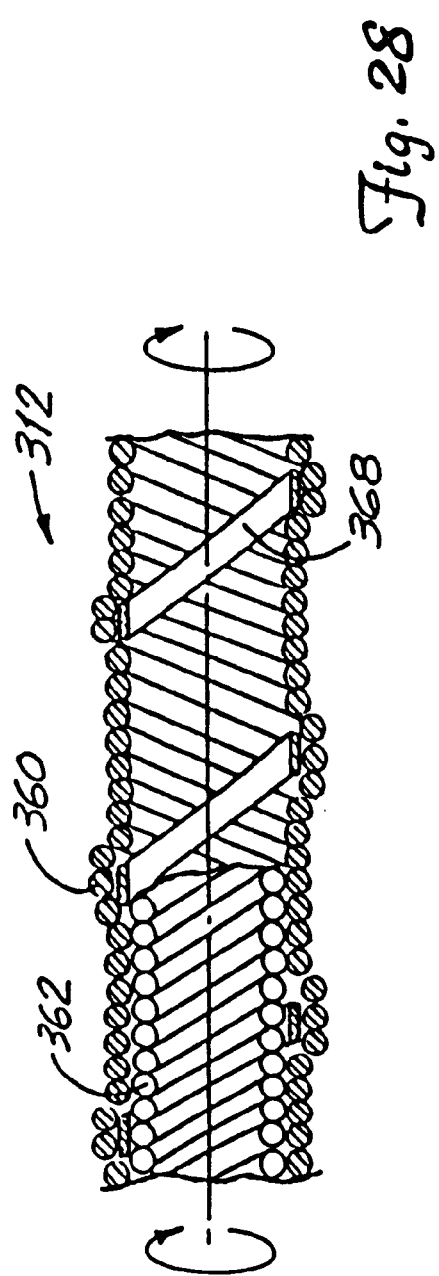
Fig. 27
Fig. 28

EXPANDABLE INTRAVASCULAR OCCLUSION MATERIAL REMOVAL DEVICES AND METHODS OF USE

CROSS REFERENCE TO RELATED APPLICATIONS

This application is a continuation application of U.S application Ser. No. 08/621,350, filed on Mar. 25, 1996, abandoned, which in turn is a continuation-in-part of U.S. application Ser. Nos. 08/206,053, filed on Mar. 3, 1994, now U.S. Pat. No. 5,501,694, and U.S. application Ser. No. 08/261,813, filed Jun. 17, 1994, now U.S. Pat. No. 5,540,707, which in turn are continuation-in-part applications of U.S. application Ser. No. 08/055,995, filed Apr. 29, 1993, now U.S. Pat. No. 5,490,859.

BACKGROUND OF THE INVENTION

The present invention generally relates to constructions for intravascular treatment devices useful for removing vascular occlusion material from a vascular occlusion or from a vascular lumen. The invention more specifically relates to expandable intravascular occlusion material removal devices, as well as to methods of using those devices to treat vascular diseases.

Vascular diseases, such as atherosclerosis and the like, have become quite prevalent in the modern day. These diseases may present themselves in a number of forms. Each form of vascular disease may require a different method of treatment to reduce or cure the harmful effects of the disease. Vascular diseases, for example, may take the form of deposits or growths in a patient's vasculature which may restrict, in the case of a partial occlusion, or stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies are being developed. While a number of invasive therapies are available, it is desirable to develop non-invasive therapies as well. Non-invasive therapies may be less risky than invasive ones, and may be more welcomed by the patient because of the possibility of decreased chances of infection, reduced post-operative pain, and less post-operative rehabilitation. One type of non-invasive therapy for vascular diseases is pharmaceutical in nature. Clot-busting drugs have been employed to help break up blood clots which may be blocking a particular vascular lumen. Other drug therapies are also available. Further non-invasive, intravascular treatments exist that are not only pharmaceutical, but also revascularize blood vessels or lumens by mechanical means. Two examples of such intravascular therapies are balloon angioplasty and atherectomy which physically revascularize a portion of a patient's vasculature.

Balloon angioplasty comprises a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member which is placed adjacent the vascular occlusion and then is inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It is to be noted, however, that this procedure does not remove the occluding matter from the patient's vasculature, but displaces it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus are not prone or susceptible to angioplastic treatment. Even if angioplasty is successful, thereby revascularizing the vessel and substantially restoring normal blood flow therethrough, there is a chance that the occlusion may recur. Recurrence of an occlusion may require repeated or alternative treatments given at the same intravascular site.

Accordingly, attempts have been made to develop other alternative mechanical methods of non-invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty and/or drug therapies.

One such alternative mechanical treatment method involves removal, not displacement, as is the case with balloon angioplasty, of the material occluding a vascular lumen. Such treatment devices, sometimes referred to as atherectomy devices, use a variety of means, such as lasers, and rotating cutters or ablaters, for example, to remove the occluding material. The rotating cutters may be particularly useful in removing certain vascular occlusions. Since vascular occlusions may have different compositions and morphology or shape, a given removal or cutting element may not be suitable for removal of a certain occlusion. Alternatively, if a patient has multiple occlusions in his vasculature, a given removal element may be suitable for removing only one of the occlusions. Suitability of a particular cutting element may be determined by, for example, its size or shape. Thus, a treating physician may have to use a plurality of different treatment devices to provide the patient with complete treatment. This type of procedure can be quite expensive because multiple pieces of equipment may need to be used (such intravascular devices are not reusable because they are inserted directly into the blood stream), and may be tedious to perform because multiple pieces of equipment must be navigated through an often-tortuous vascular path to the treatment site.

SUMMARY OF THE INVENTION

The present invention overcomes the disadvantages found in the prior art by providing an improved expandable removal element for an atherectomy device. The expandable removal element is movable between an expanded position and a contracted position and may be utilize in a single or multiple drive shaft configuration.

In one embodiment of the present invention, a drive shaft is operatively connected to a distal end of the expandable material removal element for rotating the removal element. A catheter surrounds a portion of the drive shaft. The catheter has a distal end for operatively variably contacting the proximal end of the material removal element such that the removal element is rotatable with respect to the catheter. The catheter is shiftable with respect to the drive shaft for moving the material removal element between the expanded position and the contracted position. A number of methods, according to the teachings of this embodiment of the present invention, for removing vascular occlusion material are provided. One such method comprises the steps of: providing a vascular occlusion material removal device having an expandable occlusion material removal element, wherein the removal element comprises a plurality of braided wires, further comprising an abrasive disposed on the wires; providing a drive shaft disposed in and shiftable with respect to the removal element; intravascularly positioning the removal element distally of the occlusion material; shifting the drive shaft with respect to the removal element to expand the element intravascularly; and moving the removal element proximally within the vascular lumen to remove occlusion material. The removal element can also be moved distally within the vascular lumen to engage the occlusion material. Also, removed occlusion material can be collected by a collection portion on the removal element.

In another embodiment of the present invention, dual coaxial drive shafts are employed. An outer drive shaft is operatively connected to the proximal end of the expandable material removal element and an inner drive shaft is operatively connected to the distal end of the expandable material removal element. The inner drive shaft and the outer drive are shiftable with respect to one another for moving the removal element between the expanded position and the contracted position. An outer sheath surrounds a portion of the coaxial inner and outer drive shafts such that the drive shafts and the removal element are rotatable and shiftable with respect to the outer sheath. It is contemplated that the entire assembly including the inner drive shaft, outer drive shaft, and the outer sheath can be used in conjunction with a standard guide catheter.

A number of methods, according to the teachings of the dual drive shaft embodiment of the present invention for removing vascular occlusion material are provided. One such method for operating this embodiment of the present invention comprises the steps of: providing a vascular occlusion material removal device having an expandable occlusion material removal element, wherein the removal element comprises a plurality of braided wires, further comprising an abrasive disposed on the wires; providing two coaxial drive shafts wherein an inner drive shaft is operatively coupled to a distal end of the removal element and an outer drive shaft is operatively coupled to the proximal end of the removal element and wherein the two drive shafts are shiftable with respect to one another for moving the material removal element between the expanded position and the contracted position; intravascularly positioning the removal element distally of the occlusion material; shifting the drive shafts with respect to one another causing the removal element to expand intravascularly; and moving the removal element proximally within the vascular lumen to remove occlusion material. The removal element can also be moved distally within the vascular lumen to engage the occlusion material. Also, removed occlusion material can be collected by a collection portion on the removal element.

The present invention describes a number of embodiments of improved removal elements. One embodiment of the removal element of the present invention includes a plurality of individual wires in a "multi-ended" configuration to increase the abrasive surface area of the removal element. In this "multi-ended" configuration, a plurality of wires are bundled together to form a multi-ended strand. A plurality of multi-ended strands are then braided together and an abrasive is disposed thereon to form the removal element.

Another embodiment of the removal element of the present invention comprises a plurality of braided strands having an abrasive disposed thereon wherein each strand is individually radially wrapped with a second "wrapping" wire. One advantage of the exemplary embodiment is that primary braid wire 340 may be manufactured from a material with advantageous properties to enhance proper expansion and contraction of removal element 252 while wrapping wire 342 may be made from a material which readily accepts an abrasive 344. In addition, primary braid wire 340 may continually be expanded and contracted as removal element 252 is expanded and contracted and therefore primary braid wire 340 may experience some stress. As a result, abrasive coating 344 placed thereon may become fatigued after prolonged use. Wrapping wire 342, on the other hand, is in a coil configuration around primary braid wire 340 and therefore may not experience the same level of stress as primary braid wire 340. Therefore, abrasive coating 344 placed thereon may then remain in tact despite prolonged use.

BRIEF DESCRIPTION OF THE DRAWINGS

The organization and manner of the structure and operation of the invention, together with further advantages thereof, may best be understood by reference to the following description taken in connection with the accompanying drawings, wherein like reference numerals identify like elements in which:

FIG. 1 is a partially sectioned side elevational view of an expandable vascular occlusion material removal device;

FIG. 2 is an enlarged partially sectioned side elevational view of a proximal portion of the occlusion material removal device of FIG. 1;

FIG. 3 is a view, similar to that of FIG. 2, of an alternative embodiment of the proximal portion of the occlusion material removal device of FIG. 1;

FIG. 4 is an enlarged, partially sectioned side elevational view of a distal portion of the occlusion material removal device of FIG. 1 showing an expandable material removal element in a contracted position;

FIG. 5 is a view, similar to that of FIG. 4 illustrating the expandable material removal element in an expanded position;

FIG. 6 is an enlarged, partially sectioned side elevational view of an alternative embodiment of the distal portion of the removal device of FIG. 1;

FIG. 7 is a view, similar to that of FIG. 6, of another embodiment of the distal portion;

FIG. 8 is a view, similar to that of FIG. 7, of an additional embodiment of the distal portion;

FIG. 9 is a view, similar to that of FIG. 8, of yet a further embodiment of the distal portion;

FIG. 10 is a view, similar to that of FIG. 1, of another embodiment of the expandable occlusion material removal device having a dilating member at a distal portion thereof;

FIG. 11 is a sectional view of an expandable occlusion material removal element disposed within an occluded vascular lumen showing the conformity of the removal element to the non-occluded lumen;

FIG. 13 is an enlarged sectional view of a distal end of the removal device of FIG. 12 showing the removal element in a contracted position;

FIG. 14 is a view, similar to that of FIG. 13, illustrating the removal element in an expanded position;

FIG. 15 is a sectional view of the removal element of FIG. 14 in a contracted position forming a pilot hole through an occlusion within a vascular lumen;

FIG. 16 is a view, similar to that of FIG. 15, showing the removal element expanded against the occlusion.

FIG. 25 is an enlarged side elevational view of an exemplary embodiment of expandable removal element 252.

FIG. 26 shows an expandable view of an exemplary embodiment of one strand 351 within the braid pattern of removal element 252.

FIG. 27 is an enlarged partially-sectioned side elevational view of the dual drive shaft embodiment of the present invention.

FIG. 28 is an expanded partial sectional side view of another embodiment of the inner drive shaft.

DETAILED DESCRIPTION OF THE PREFERRED EMBODIMENTS

Figure 12:
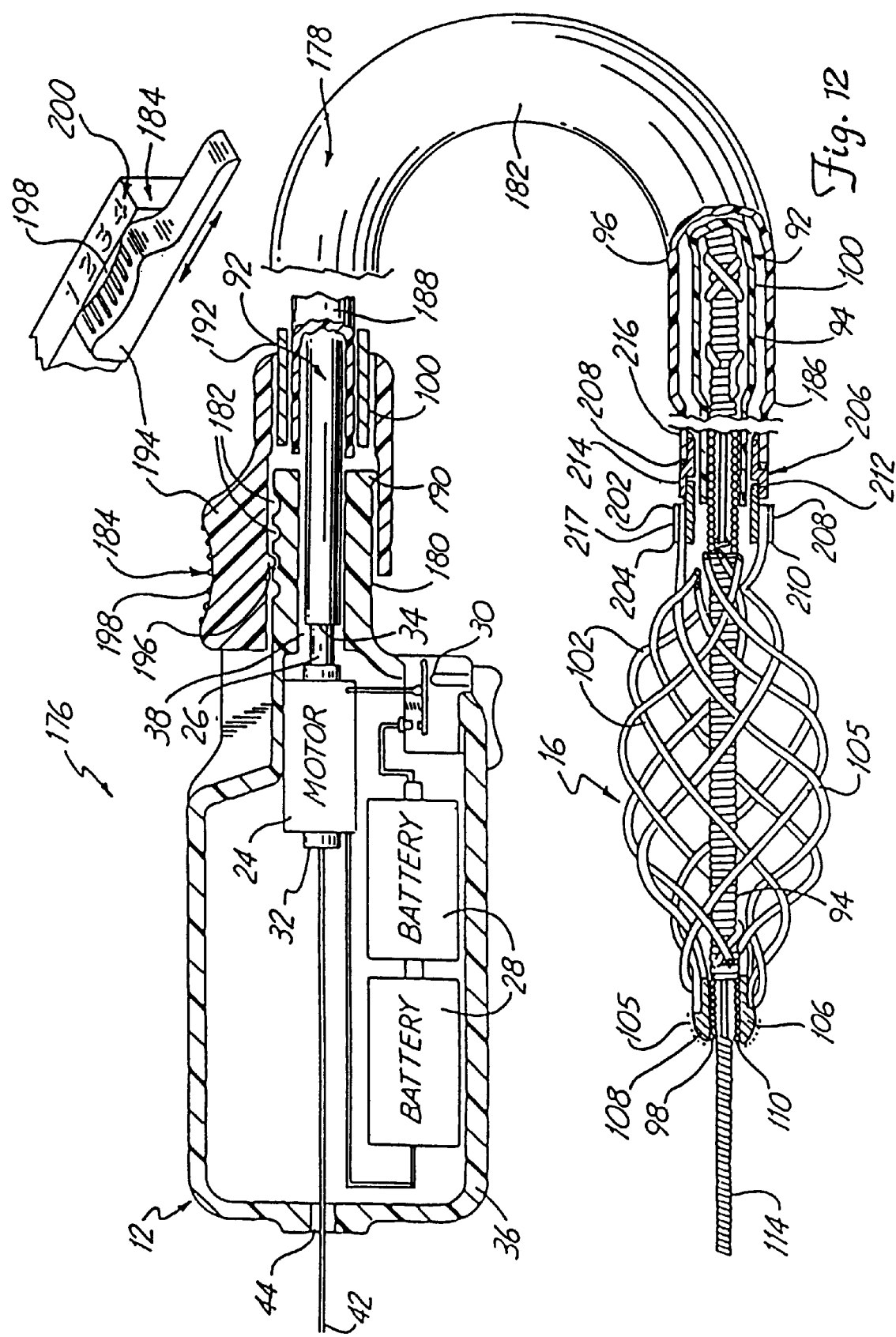
FIG. 12 is a sectional view of yet another embodiment of an expandable occlusion material removal device with the removal element in an expanded position.

While the invention may be susceptible to embodiment in different forms, there are shown in the drawings, and herein will be described in detail, specific embodiments with the understanding that the present disclosure is to be considered an exemplification of the principles of the invention, and is not intended to limit the invention to that as illustrated and described herein.

The various embodiments of the present invention provide a number of constructions of expandable vascular occlusion material removal devices, intravascular material removal elements, and the like, which can be utilized to perform a plurality of different intravascular treatments, such as atherectomy, thrombectomy, angioplasty and the like. The embodiments of the present invention also provide a plurality of methods for using those devices and their associated vascular occlusion material removal elements for performing intravascular treatments on a patient. It is to be fully recognized that the different teachings of the below-discussed embodiments can be employed separately or in any suitable combination to produce desired results. The embodiments provide, in the form of expandable intravascular removal elements, ways of changing cutting or removing profiles, configurations or characteristics of a particular intravascular treatment device while only using a single removal element.

Referring initially to FIG. 1, an expandable intravascular occlusion material removal device 10 is illustrated. The removal device 10 generally comprises a drive assembly 12, a catheter assembly 14, and an expandable material removal element 16 located at a distal end 18 of the catheter assembly 14. A proximal end 20 of the catheter assembly 14 is connected to a manifold assembly 22 which forms a connection between the drive assembly 12 and the catheter assembly 14.

The constructions of the drive assembly 12 and the manifold assembly 22 are more clearly shown in FIGS. 1 and 2. The drive assembly 12 generally comprises an electric motor 24 having a hollow, rotatable drive shaft 26, a power source 28, illustrated as a plurality of batteries electrically connected in series, for energizing the motor 24, and a control switch 30 connected electrically between the motor 24 and the power source 28 such that actuation of the control switch 30 allows current to flow between the power source 28 and the motor 24, thereby causing the drive shaft 26 to rotate. In an exemplary embodiment of the invention, the motor 24 is a direct current micro-motor available from Micro Mo Electronics, Inc. of St. Petersburg, Fla., series number 2233-04.5S, and the power source 28 is a pair of 3 Volt lithium batteries. The motor 24 can rotate the drive shaft 26 at a speed of about 10,000 revolutions per minute, but it is envisioned that greater speeds, on the order of 100,000 revolutions per minute may be possible with different motors 24. For example, the motor 24 may be similar to the brushless direct current motor available from Transicoil Inc. of Valley Forge, Pa., model number U-222285, which can reach speeds of 100,000 revolutions per minute. By rotating the drive shaft 26 at this speed, more efficient removal of occlusion material may be achieved because the intravascular treatment may take less time. Thus, the removal device 10 can operate at speeds substantially within the range of 0 to 100,000 revolutions per minute. As FIG. 1 shows, the drive shaft 26 extends through the motor 24 with a proximal end 32 thereof projecting from a proximal end of the motor 24, and with a distal end 34 thereof extending out of an aperture 38 located on a distal end of a housing 36 which contains elements of the drive assembly 12. The significance of this structure will become clear later.

An inner hollow tube or sheath 40 is located between an inner, proximal end of the housing 36 and the proximal end of the motor 24 such that the proximal end 32 of the drive shaft 26 extends into the hollow interior of the inner sheath 40. The inner sheath 40 defines a lumen 46 of dimensions sufficient for accepting a medical guidewire 42, made of stainless steel, nitinol, and the like, which can extend from the guidewire lumen 46 within the inner sheath 40, and through an aperture 44 in the proximal end of the housing 36 to the exterior of the housing 36. Because the drive shaft 26 of the motor 24 is hollow, the guidewire 42 can pass through the catheter assembly 14, into the manifold assembly 22 and into the drive shaft 26. A fluid seal 43, such as a diaphragm and the like, is provided at the proximal end 32 of the drive shaft 26 so that fluid within the drive shaft 26 cannot leak into the interior of the housing 36. However, the fluid seal 43 is of appropriate construction to allow the guidewire 42 to extend from the drive shaft 26 into the inner sheath 40.

The distal end 34 of the drive shaft 26 of the motor 24 is fixedly connected to a hollow drive shaft 92 which extends axially through the catheter assembly 14 and is connected to the material removal element 16. In an exemplary embodiment, the drive shaft 92 has an outer diameter of about 0.025". The hollow drive shaft 92 also defines a guidewire lumen, thereby allowing for passage of the guidewire 42 from the material removal element 16 to the exterior of the housing 36. Thus, the removal device 10 is of an over-the-wire construction which can facilitate removing the device 10 from, and replacing the device 10 in the patient because the guidewire 42 can remain within the patient. Comparatively, some prior art devices require removal of the guidewire along with the device, thereby necessitating additional intravascular navigation not only of the device, but also of the guidewire to replace the device adjacent the occlusion material to be removed. In addition, the presence of the guidewire 42 facilitates intravascular navigation of the removal device 10, because the device 10 can be delivered over the guidewire 42, which is an improvement over some expandable intravascular devices.

The guidewire 42 is also axially shiftable with respect to the drive assembly 12 and the catheter assembly 14 so that shifting of the guidewire 42 induces corresponding movement of the material removal element 16 between a contracted position (FIG. 4) and an expanded position (FIG. 5). This operation will be discussed in greater detail hereinbelow. The guidewire 42 must have sufficient strength to transmit force to the material removal element 16 to cause movement between the contracted and expanded positions. This is an important distinction from some prior art devices which require a mechanism in addition to a medical guidewire to expand an element intravascularly. Thus, the expandable intravascular occlusion material removal device 10 is of a construction substantially simpler than some of the prior art devices. A variable length of the guidewire 42 can be shifted distally of the removal element 16 for facilitating intravascular navigation of the removal device 10. In an exemplary embodiment of the removal device 10, the guidewire 42 has an outer diameter measuring substantially within the range of 0.010" to 0.014". Also, the guidewire 42 may be coated with a low friction coating, such as a nickel-silver alloy like nikasil, or a fluoropolymer infused nickel substance like nedox, for reducing friction between the guidewire 42 and the removal device 10.

Because axial shifting of the guidewire 42 causes expansion or contraction of the material removal element 16, the drive assembly 12 includes structures for providing a treating physician with positive control over axial movement of the guidewire 42. Specifically, as shown in FIG. 2, the drive assembly 12 includes a guidewire lock mechanism 50 and a material removal element expansion control mechanism 52, both of which serve to positively control expansion or contraction of the material removal element 16 by controlling axial shifting of the guidewire 42. The guidewire lock mechanism 50 holds the guidewire 42 fixed with respect to itself and to the control mechanism 52 which allows a treating physician to positively axially shift the guidewire 42 and the guidewire lock mechanism 50 by actuation of the expansion control mechanism 52, as will be discussed in greater detail later.

The guidewire lock mechanism 50 is located at a proximal end of the housing 36 adjacent the aperture 44. The guidewire lock mechanism 50 may function substantially similarly to a pin vise, and comprises a wire lock knob 54 and an inner collet 56, shown in section in FIG. 2, through which the guidewire 42 passes. The wire lock knob 54 and the inner collect 56 are disposed at a proximal end of an outer hollow tube or sheath 58 which also passes through the aperture 44 into the interior of the housing 36. The outer sheath 58 accepts the guidewire 42 and also the inner sheath 40. The outer sheath 58 is axially shiftable with respect to the inner sheath 40, and slides along an outer surface of the inner sheath 40, which remains fixed within the housing 36, responsive to actuation of the expansion control mechanism 52, as will be discussed below.

A portion of the inner collet 56 extends into the interior of the outer sheath 58 where that portion can engage an outer diameter surface of the guidewire 42. The wire lock knob 54 is rotatable with respect to the inner collet 56 and the outer sheath 58, and is threaded variably onto the proximal end of the outer sheath 58. Thus, as the wire lock knob 54 is appropriately rotated with respect to the inner collet 56 and the outer sheath 58, the wire lock knob 54 moves distally along the outer sheath 58 by means of the threaded engagement therebetween, which forces the inner collet 56 to engage the outer surface of the guidewire 42. The wire lock knob 54 is rotated on the outer sheath 58 sufficiently to compress the inner collet 56 against the guidewire 42 such that the guidewire 42 is fixed with respect to the guidewire lock mechanism 50 and the outer sheath 58. However, the outer sheath 58 is axially shiftable with respect to the inner sheath 40, the motor 24 and the drive shaft 26 responsive to actuation of the expansion control mechanism 52. Thus, the guidewire 42 is also positively shiftable responsive to movement of the control mechanism 52. Proper application of the guidewire lock mechanism 50 to the guidewire 42 allows a physician to positively vary expansion and/or contraction of the expandable material removal element 16. To release the guidewire 42 from the grip of the inner collet 56 and the wire lock mechanism 50, the wire lock knob 54 is rotated in an opposite direction, thereby allowing a portion of the inner collet 56 to move out of the outer sheath 58, and out of engagement with the outer surface of the guidewire 42.

The material removal element expansion control mechanism 52 is operatively connected to the outer sheath 58 such that actuation of the control mechanism 52 causes conjoint motion of the outer sheath 58 and the guidewire 42, which causes expansion and/or contraction of the material removal element 16 (assuming that the wire lock mechanism 50 holds the guidewire 42 fixed with respect to the control mechanism 52 and the outer sheath 58). Specifically, the material removal element expansion control mechanism 52 comprises a shaft 60 extending substantially perpendicularly from the inner sheath 40 and the outer sheath 58 through an elongate slot 62 in the housing 36. One end of the shaft 60 is connected to a shoulder portion 64 located adjacent a distal end of the outer sheath 58 by a compressible spring 65. The spring 65 biases the shaft 60 away from the outer sheath 58. An opposite end of the shaft 60 extends out of the housing 36 through the slot 62 where it is connected to a thumb pad 66. The thumb pad 66 is configured for facilitating application of a force from a treating physician's thumb to induce axial shifting of the guidewire 42, and thus, corresponding expansion and/or contraction of the expandable material removal element 16.

Means is provided within the housing 36 to facilitate positive shifting of the guidewire 42, and also positive movement of the expandable material removal element 16 between the expanded and contracted positions. Specifically, in the illustrated embodiment, a first set of teeth 68 is attached to the shaft 60 such that the teeth 68 extend perpendicularly with respect to an axis of elongation of the shaft 60 and substantially parallel with respect to an adjacent portion of the housing 36. Because the shaft 60 can move against the spring 65 under the influence of forces applied to the thumb pad 66, the first set of teeth 68 is also movable in corresponding fashion. A second set of teeth 70 depend from the interior surface of the housing 36 adjacent the slot 62 such that the first set of teeth 68 is interengagable with the second set of teeth 70. The second set of teeth 70 is fixed with respect to the housing 36 such that, when the teeth 68 and 70 are interengaged, the outer sheath 58 is fixed with respect to the housing 36. This prevents axial shifting of the guidewire 42 with respect to the drive assembly 12, the catheter assembly 14, and the removal element 16 if the guidewire lock mechanism 50 is applied.

The structure of the guidewire lock mechanism 50 and the material removal element expansion control mechanism 52 may be more readily understood with reference to the following discussion of the operation thereof. The guidewire 42 is disposed through the drive shaft 26, the motor 24, the inner sheath 40, the outer sheath 58, the inner collet 56 and the wire lock knob 54. The wire lock knob 54 is rotated with respect to the outer sheath 58 such that threads on the lock knob 54 and the outer sheath 58 cooperate to cause distally directed movement of the lock knob 54 with respect to the outer sheath 58. Distally directed movement of the lock knob 54 forces the inner collet 56 progressively further into the interior of the outer sheath 58. As the inner collet 56 moves into the outer sheath 58, a portion of the inner collet 56 within the outer sheath 58 engages an outer surface of the guidewire 42. The wire lock knob 54 is rotated on the outer sheath 58 so that the portion of the inner collet 56 engages the outer surface of the guidewire 42 with sufficient force to hold the guidewire 42 fixed with respect to the outer sheath 58 and the guidewire lock mechanism 50. The guidewire 42, the guidewire lock mechanism 50 and the outer sheath 58 now move conjointly.

A treating physician applies an appropriate force to the thumb pad 66, thereby causing movement of the shaft 60 towards the shoulder portion 64 of the outer sheath 58 and compressing the spring 65 between an end of the shaft 60 and the shoulder portion 64 of the outer sheath 58. Sufficient movement of the shaft 60 towards the shoulder portion 64 and sufficient compression of the spring 65 disengages the teeth 68 from the teeth 70 because the teeth 68 move conjointly with the shaft 60 while the teeth 70 remain fixed. The treating physician can now apply forces to the thumb pad 66 to conjointly axially shift the guidewire 42, the outer sheath 58, the guidewire lock mechanism 50 and the material removal element expansion control mechanism 52.

Specifically, the treating physician can apply forces to the thumb pad 66 to move or shift the guidewire 42 and the outer sheath 58 proximally rearwardly. This movement, as will be discussed in greater detail later, causes expansion of the material removal element 16. As these forces are applied to the thumb pad 66, those forces are transmitted to the shoulder portion 64 of the outer sheath 58. The outer sheath 58 slides proximally along the outer surface of the inner sheath 40 towards the aperture 44 in the housing 36. The range of sliding motion of the outer sheath 58 along the inner sheath 40 is limited by engagement of a proximal end of the teeth 68 with the adjacent interior surface of the housing 36, as well as by the dimensions of the elongate slot 62 in which a portion of the shaft 60 moves conjointly with the outer sheath 58.

The degree of material removal element 16 expansion is directly proportional to the length of axial shifting of the guidewire 42 and the outer sheath 58 proximally. Thus, the degree of material removal element 16 expansion and/or contraction can be measured by suitable scaling means 59 or 79 disposed on the housing 36 adjacent the elongate slot 62. When a desired degree of material removal element 16 expansion has been achieved, the thumb pad 66 can be released. The spring 65 now expands and forces the teeth 68 into engagement with the teeth 70. Interengagement of the teeth 68 and 70 positively locks the axial position of the guidewire 42, and thus, also the expanded position of the material removal element 16. Because a plurality of teeth 68 and 70 are provided, the material removal element expansion control mechanism 52 allows for positively controlled, incremental expansion of the material removal element 16. To contract the expandable material removal element 16, the above-discussed steps are repeated, but this time, the treating physician moves the thumb pad 66 and the guidewire 42 distally.

An alternative embodiment of the material removal element expansion control mechanism 52 is illustrated in FIG. 3. It is to be noted that the construction of this embodiment is substantially similar to that illustrated in FIGS. 1 and 2, except for the differences noted hereinbelow, hence the like reference numerals for similar structures. The guidewire lock mechanism 50 of the embodiment of FIG. 2 is the same as that of the embodiment of FIG. 3.

Specifically, in the embodiment of FIG. 3, the material removal element expansion control mechanism 52 comprises an expansion knob 72 and a threaded hub 74. The threaded hub 74 extends from and is fixed to a proximal end of the housing 36 and surrounds the aperture 44 in the housing 36 and the outer sheath 58. The expansion knob 72 has internal threads matable with the threads on the threaded hub 74, and is disposed on the hub 74 such that the knob 72 surrounds the hub 74. The expansion knob 72 is rotatable on the threaded hub 74, and the threads thereon cooperate so that rotation of the expansion knob 72 on the threaded hub 74 causes the expansion knob 72 to move proximally or distally with respect to the hub 74, depending upon the direction of rotation. Distal movement of the expansion knob 72 causes contraction of the material removal element 16 and proximal movement of the expansion knob 72 causes expansion of the material removal element 16.

To expand the material removal element 16, the expansion knob 72 is rotated such that the knob 72 moves proximally on the threaded hub 74 so that a proximal end 76 of the expansion knob 72 contacts a distal end of the wire lock knob 54. Further proximal motion of the expansion knob 72 forces the wire lock knob 54 to shift proximally with respect to the drive assembly 12, thereby shifting the guidewire 42 proximally as well. The outer sheath 58 conjointly slides proximally along the outer surface of the inner sheath 40, as discussed above. Proximal movement of the expansion knob 72 on the threaded hub 74 is positively limited, thereby limiting the maximum size of the expandable material removal element 16. Specifically, upon sufficient rotation and proximal movement of the expansion knob 72, a proximal end of the shoulder portion 64 engages an interior proximal side of the housing 36.

The expandable material removal element 16 can be contracted by reversing the direction of rotation of the expansion knob 72. To facilitate return of the material removal element 16 from the expanded position to the contracted position, a coiled spring 77 may be disposed between the shoulder portion 64 and the proximal end of the motor 24, as shown in FIG. 3, or, alternatively, disposed between the shoulder portion 64 and the proximal end of the housing 36. The spring 77 relaxes as the expansion knob 72 moves distally on the threaded hub 74. Relaxation of the spring 77 moves the outer sheath 58, the wire lock knob 54 and the guidewire 42 proximally with respect to the drive assembly 12. Suitable scaling means 59 or 79 can be provided on the expansion knob 72 and/or the housing 36 for providing a treating physician with a positive indication of the degree of expansion and/or contraction of the expandable material removal element 16.

The construction of the manifold assembly 22 is illustrated in FIGS. 1 through 3. The manifold assembly 22 connects the drive assembly 12 to the catheter assembly 16. The manifold assembly 22 generally comprises a main lumen 78 which extends from a distal end of the housing 36 to the proximal end 20 of the catheter assembly 14, and has at least two ports 80 and 82, accessible from the exterior of the manifold assembly 22, which communicate with the main lumen 78. The hollow drive shaft 26 of the motor 24 extends through the aperture 38 in the housing 36 and into the main lumen 78. The drive shaft 26 has a lumen therein of dimensions sufficient for accepting the guidewire 42 so that the guidewire 42 can also extend into the main lumen 78 within the drive shaft 26.

In the illustrated embodiment, the drive shaft 26 extends into the main lumen 78 a distance sufficient to locate the distal end 34 of the drive shaft 26 distally of the port 80. A pair of fluid seals 84 and 86 are provided within the main lumen 78 on opposite sides of the port 80. The fluid seals 84 and 86 extend from the main lumen 78 to an outer surface of the drive shaft 26 and form a fluid-tight seal around a portion of the drive shaft 26 therebetween. A longitudinal aperture 88 is located on the drive shaft 26 between the fluid seals 84 and 86 for allowing fluid to pass into the hollow interior of the drive shaft 26. This construction allows the port 80 to be dedicated to infusion of fluids into the drive shaft 26. This infused fluid can provide for increased lubrication between the outer surface of the guidewire 42 and the inner surface of the drive shaft 26, which may be beneficial during operation of the motor 24, and for allowing irrigation of an intravascular treatment site, which may be necessary to maintain a fluid balance within a vascular lumen if aspiration techniques are also used. Accordingly, the port 80 is connectable to a suitable fluid source, not shown, but well known in the art. The port 82 can be utilized for infusion of fluids, such as contrast media, saline, a drug therapy, and the like, into the patient, and for aspiration of the intravascular treatment site. The fluid seals 84 and 86 provide for this independent operation of the ports 80 and 82, and also insure that fluids introduced into the main lumen 78 will not reach the motor 24. To insure delivery of the fluids for infusion or negative pressures for aspiration, the port 82 communicates with a catheter sheath 90 connected to the distal end of the manifold assembly 22. The catheter sheath 90 is of well known construction, and can be made from polyethylene, KYNAR, a fluoropolymer and the like. In an exemplary embodiment, the catheter sheath 90 can have an axial length of about 133 cm and an outer diameter of about 0.072", thereby enabling it to be inserted into a 7 French guide catheter. The proximal end of the catheter sheath 90 defines the proximal end 20 of the catheter assembly 14.

The distal end 34 of the hollow drive shaft 26 is fixedly attached to another hollow drive shaft 92, which extends through the catheter sheath 90 of the catheter assembly 14, so that the drive shafts 24 and 92 rotate conjointly. The construction of the drive shaft 92 is illustrated in FIGS. 4 and 5. Specifically, the drive shaft 92 comprises an inner coil 94, preferably formed from a plurality of intertwined strands of a wire composed of a suitable metal, such as stainless steel or nitinol, wound in a predetermined direction such that the coil 94 expands radially upon rotation of the drive shaft 92. This maintains or increases the clearance between the outer surface of the guidewire 42 and the inner surface of the coil 94. In order to limit radial and axial expansion of the inner coil 94, a wire braid 96, formed from a metal such as stainless steel, nitinol or the like, is applied over a portion of the outer diameter surface of the coil 94. Wires forming the inner coil 94 and the braid 96 can have a rounded or flattened configuration.

An end of the braid 96 is applied over the outer diameter surface of the coil 94 and attached by suitable means, such as solder, braze, and the like, to a proximal end of the inner coil 94. The braid 96 is then stretched axially or tensioned along the length of the inner coil 94, thereby closely confining radial expansion of the individual windings of the inner coil 94. Once stretched, an end of the braid 96 is attached to a portion of the inner coil 94 preferably offset proximally of a distal end 98 of the inner coil 94. This, in the illustrated embodiment, leaves a number of distal-most windings of the inner coil 94 uncovered by the braid 96, however, it is to be understood that the braid 96 can extend along the entire axial length of the coil 94 or may be entirely eliminated.

Tensioning the braid 96 over the outer diameter surface of the inner coil 94 limits the radial expansion of the coil 94 during operation of the motor 24. In addition, by covering the proximal portion of the inner coil 94 with the braid 96, the drive shaft 92 has an increased torque rigidity as compared to the coil 94 alone. Torque transfer to the expandable material removal element 16 is correspondingly increased, and the distal end 98 of the inner coil 94 is more responsive to proximally applied torques. Furthermore, by leaving a distal-most portion of the coil 94 uncovered by the braid 96, that portion is rather flexible and has increased trackability, thereby making it easier to torque the distal end 98 through tight curves within a patient's vasculature. To further improve trackability, as well as to reduce friction between the outer surface of the drive shaft 92 and the inner surface of the catheter sheath 90, a lubricous or low friction coating 100, comprised of a fluoropolymer and the like, is applied to the outer surface of the drive shaft 92. The coating 100 may be provided in the form of a sheath of a fluoropolymer which shrinks upon application of heat. In this manner, the coating 100 can reduce friction between the drive shaft 92 and the coating 100, provide the drive shaft 92 with increased torsional rigidity, limit radial expansion of the drive shaft 92, and form a fluid-tight lumen through the drive shaft 92. The coating 100 can also insure proper aspiration through the catheter sheath 90 by minimizing friction between the drive shaft 92 and occlusion material aspirated into the catheter sheath 90. Also, as shown in FIGS. 1, 4 and 5, the catheter sheath 90 terminates at a location offset proximally of the distal end 98 of the drive shaft 92 and a proximal end of the material removal element 16. This provides for proper irrigation and aspiration of an intravascular treatment site because the irrigation site is located distally of the aspiration site.

In some embodiments, the drive shaft 92 may not include the braid 96. In these embodiments, the inner coil 94 of the drive shaft 92 is formed by wires wound opposite to the intended direction of rotation of the drive shaft 92. In this manner, the coil 94 may radially expand upon rotation of the drive shaft 92. Another coil, formed by wires wound in the intended direction of drive shaft 92 rotation surrounds the inner coil 94. Because this outer coil is wound in the direction of drive shaft 92 rotation, the outer coil may radially contract upon rotation of the drive shaft 92. The radial expansion of the inner coil 94 is balanced by the radially contraction of the outer coil. Thus, the outer coil can perform substantially the same function as the braid 96. Some embodiments of the drive shaft 92 may axially expand or contract responsive to radial contraction or expansion, respectively, thereof during operation of the removal device 10. The drive shaft 92 may be constructed, by appropriately winding the inner and outer coils, to render axially expansion and/or contraction of the drive shaft 92 controllable.

The axial expansion or contraction of the drive shaft 92 may also effect radial expansion of the removal element 16. This will be discussed further later.

The distal end 98 of the inner coil 94 is fixedly attached to the expandable material removal element 16 so that the drive shaft 92 and the material removal element 16 rotate conjointly. The material removal element 16 generally comprises a plurality, preferably 8 or 16, of braided wires 102. The wires 102 themselves preferably have a substantially round latitudinal cross section defining an outer diameter of about 0.002" to 0.006", although wires having flat, square, or triangular cross sections can also be used. In an exemplary embodiment of the removal element 16, the wires 102 comprise nitinol super-elastic wire, chromium-doped as drawn, having a diameter of about 0.003". In this embodiment, 16 nitinol wires 102 are braided at about 80 to 120 pics per inch and heat set at approximately 500 degrees Celsius for about 5 minutes. This embodiment of the removal element 16 has a length substantially within the range of about 1 cm to 3 cm, a contracted diameter substantially within the range of 1 mm to 1.125 mm, and a maximum expanded diameter of about 4 mm. In another exemplary embodiment, the wires 102 define a removal element 16 having an axial length of about 1.5 cm, and an outer diameter of about 1.25 mm in the contracted position. In the fully expanded position, this other embodiment of the removal element 16 can define an outer diameter measuring substantially within the range of 2.0 to 4.0 mm.

The outer surfaces of the wires 102 may be sharpened, etched or coated with an abrasive 105, such as a diamond grit and the like, to improve the removing or cutting characteristics of the material removal element 16. In one embodiment, a diamond grit having a grit size substantially within the range of 5 to 100 microns is electroplated onto the wires 102 in substantially uniform manner, however, the grit may be asymmetrically deposited on the wires 102 if desired. In another exemplary embodiment, the abrasive 105 may comprise a diamond grit or synthetic abrasive, such as a cubic boron nitride and the like, having a grit size approximately within the range of 10 to 25 microns, attached to the wires 102 by a nickel electroplating process. The disposition of the abrasive 105 on the wires 102 may depend upon the particular embodiment of the vascular occlusion material removal device.

In some embodiments, after the wires 102 are coated with the abrasive 105, a radiopaque material, such as gold, platinum, a radiopaque ink and the like, may be placed over the abrasive coated wires 102 to render the removal element 16 radioscopically visible. In still other embodiments, the abrasive coated wires 102 may be further coated with a low friction substance, such as nickel, a nickel plating infused with a fluoropolymer and the like. If nickel is used, a well known electroless plating process may be used to apply the nickel to the removal element 16. If a fluoropolymer infused nickel plating, such as nedox, is used, then this plating may be applied to the removal element 16 by the process performed by General Magnaplate Texas of Arlington, Tex. Other embodiments of the removal element 16 may not include an abrasive 105. In these embodiments, the wires 102 may be substantially ribbon-like in configuration. These ribbon-like wires are axially twisted and then braided to form the removal element 16. The edges of the twisted ribbon-like wires act substantially similarly to the abrasive 105 to remove occlusion material.

The wires 102 are preferably made from a super-elastic or shape memory metal alloy, such as nitinol and the like, which allows the wires 102 to recover strains greater than those recoverable by other metals. This increased strain recovery allows the wires 102 to resist permanent deformation during repeated expansions and contractions as well as during contact with vascular occlusion material. The use of super-elastic alloys for the wires 102 facilitates return of the material removal element 16 to its original low profile, contracted condition, which also makes intravascular navigation of the material removal element 16 easier and facilitates retention of vascular occlusion material within the material removal element 16. In an exemplary construction, the expandable material removal element 16 and the catheter assembly 14 as a whole have a sufficiently low profile to allow insertion of the catheter assembly 14 and the material removal element 16 through a conventional 7 French guide catheter.

A proximal annulus 104 is attached to the distal end 98 of the inner coil 94 by suitable means, such as an adhesive, solder, braze or a weld, and the proximal ends of the braided wires 102 are attached to the outer surface of the proximal annulus 104 by similar means. Thus, the braided wires 102 comprising the material removal element 16 rotate conjointly with the drive shafts 26 and 92 and the proximal annulus 104 under the influence of forces generated by the motor 24. The distal ends of the wires 102 are attached to a distal annulus 106, which may be made of a metal. In an exemplary embodiment, the distal annulus 106 is a hypotube, such as a 304 stainless steel 21XX hypotube available from Micro Group, Inc. of Medway, Mass., and the wires 102 are brazed to the distal annulus 106 with a Turbo braze paste available from Turbo Braze Corporation of Union, N.J. The wires 102, proximal annulus 104, and the distal annulus 106 are radioscopically visible when the wires 102 are attached to the annuluses 104 and 106. The distal annulus 106 is provided with a cutting surface 108 located distally of the point of attachment of the wires 102. The cutting surface 108 may also be coated with an abrasive 105, such as the diamond grit or synthetic abrasive disclosed earlier.

The braided wires 102 of the material removal element 16 define a hollow interior which can ingest or capture vascular occlusion material, as will be discussed in greater detail below. Abrasive 105 on the portions of the wires 102 facing the hollow interior may facilitate retention of the captured occlusion material within the hollow interior. In addition, the dimensions of the hollow interior are sufficient to accept a distal portion of the guidewire 42. Specifically, an aperture 110 is provided in the distal annulus 106 so that the guidewire 42 can be inserted therethrough and into the hollow interior of the material removal element 16. From there, the guidewire 42 can be inserted through the proximal annulus 104 into the hollow drive shaft 92, the drive shaft 26, the motor 24, and through the inner sheath 40, the outer sheath 58, and the guidewire lock mechanism 50. To traverse this distance, the guidewire 42 may be of a length suitable for facilitating removal and replacement of the device 10 within a patient, or may be extendable, and may be coated with a lubricous or a low friction substance, such as a fluoroploymer or a fluoropolymer-loaded nickel plating, to facilitate force transfer from the guidewire 42 to the distal end of the material removal element 16. The removal device 10 can also be exchanged intravascularly according to the methods disclosed in the co-pending U.S. patent application of Mazzola et al., Ser. No. 07/789,183, filed on Nov. 8, 1991. That application is assigned to the assignee of the present invention, and the disclosure thereof is incorporated herein by reference.

A distal end of the guidewire 42 includes a bearing surface 112, which can have one of several embodiments (FIGS. 6 through 9), which is fixedly attached to the guidewire 42. For example, the bearing surface 112 may be a short tube, a bearing or a bead 120 (FIG. 6) slipped onto the guidewire 42 having a smooth, low friction surface, a braze or solder fillet 122 (FIG. 7), or may be a centerless ground bump 124 (FIG. 8) on the guidewire 42. In some embodiments, the bearing surface 112 may be coated with a low friction substance, such as a fluoropolymer and the like. The bearing surface 112 is located at a proximal end of a radiopaque coil 114 which defines a distal-most end of the guidewire 42. The coil 114 may be made from platinum or other suitable substance, and, in an exemplary embodiment, has an axial length of about 3 cm and an outer diameter of 0.014". The dimensions of the bearing surface 112 are larger than the corresponding dimensions of the aperture 110 in the annulus 106 so that the bearing surface 112 butts up against a distal end of the annulus 106, the significance of which will become more clear later. For example, the bearing surface 112 may define an outer diameter of about 0.016" and the aperture 110 may define an inner diameter of about 0.010" to 0.014". As stated above, the outer diameter surface of the guidewire 42 may be coated with a lubricous or low friction coating, such as fluoropolymer, a fluoropolymer-loaded metallic coating, a silicone dispersion, and the like, to minimize friction between the guidewire 42 and the drive shafts 26 and 92. This may be desirable because the guidewire 42 remains within the drive shafts 26 and 92 and is secured against axial movement by the wire lock mechanism 50 during operation of the occlusion material removal device 10.

With the basic structure of the occlusion material removal device 10 being thusly disclosed, a greater appreciation of the construction and benefits of the expandable material removal element 16 of the device 10 may be gained from the following discussion of the operation of the device 10. It is to be noted that this discussion is provided for illustrative purposes only.

The guidewire 42 is inserted intravascularly into the patient and navigated to the intravascular treatment site. If possible, the radiopaque coil 114 may be located through or distally of vascular occlusion material to be removed. A proximal end of the guidewire 42 is inserted through the distal annulus 106, and is guided through the more proximal portions of the removal device 10 until the distal end of the distal annulus 106 is proximate to the proximal end of the bearing surface 112 within the patient's vasculature. This procedure can be used if the guidewire 42 has sufficient length, i.e. is of exchange length. For shorter guidewires 42, the guidewire 42 can be pre-loaded into the removal element 16, and then the guidewire 42 and the element 16 can be conjointly inserted into the patient's vasculature. Sufficient length of the guidewire 42 can be positioned distally of the removal element 16 to facilitate intravascular navigation thereof.

The material removal element 16 is inserted into the patient's vasculature over the guidewire 42 while in the contracted position illustrated in FIG. 4. In an exemplary method of use, the removal device 10 is inserted into the patient's vasculature through a guide catheter or an introducer sheath in common fashion. If such a guide is used, then a fluid seal may be provided between the guide catheter and the device 10 to limit blood loss from the patient due to axial shifting of the device 10 with respect to the guide catheter. Thus, back flow of blood or other bodily fluids through a lumen between the guide catheter and the removal device 10 can be limited.

As shown, the axial distance between the distal end 98 of the inner coil 94 and the proximal end of the bearing surface 112 can be sufficient to allow the braided wires 102 comprising the material removal element 16 to completely axially relax or expand, thereby causing the material removal element 16 to contract radially. The proximal end of the bearing surface 112 may not contact the distal end of the distal annulus 106 when the material removal element 16 is in this contracted position. When in the contracted position, the material removal element 16 defines a low profile and an outer diameter slightly larger than the outer diameter of the drive shaft 92. This low profile facilitates intravascular navigation of the material removal element 16.

The removal element 16 is positioned adjacent the occlusion material to be removed. With some embodiments, the coil 114 of the guidewire 42 may have to be located across the occlusion, but it is envisioned that other embodiments may not require this. If the treating physician wishes to shift the material removal element 16 towards the expanded condition illustrated in FIG. 5, then the physician moves the guidewire 42 proximally as described above with reference to the guidewire lock mechanism 50 and the material removal element expansion control mechanism 52. As the treating physician moves the guidewire 42 proximally, the length of the guidewire 42 disposed within the patient's vascular system is reduced. Correspondingly, the axial distance between the bearing surface 112 and the distal annulus 106 decreases until the proximal end of the bearing surface 112 engages the distal end of the distal annulus 106. The guidewire 42 is moved progressively proximally and the axial distance between the distal annulus 106 and the distal end 98 of the inner coil 94 decreases. The braided wires 102 comprising the expandable material removal element 16 are axially compressed, thereby causing the material removal element 16 to expand radially.

Once the material removal element 16 is expanded to the desired degree, which can be positively verified by checking the scaling means 59 or 79 on the drive assembly 12, the thumb pad 66 of the material removal element expansion control mechanism 52 is released and now maintains the expanded position of the material removal element 16. The degree of expansion of the removal element 16 may also be positively verified by radioscopic techniques, i.e. if the particular embodiment of the removal element 16 is radioscopically visible. If the physician wishes to radially contract the material removal element 16, then he moves the guidewire 42 distally, as described hereinabove. By suitable manipulation of the guidewire 42, the guidewire lock mechanism 50, and the material removal element expansion control mechanism 52, the material removal element 16 can take on a number of different configurations and sizes, thereby changing the cutting profiles or characteristics of the material removal element 16 without having to remove the material removal element 16 from the patient's vasculature. This can provide the treating physician with greater flexibility in performing intravascular treatments, and may possibly reduce the cost of an intravascular procedure because multiple pieces of equipment need not be used.

While an expandable intravascular removal element 16 is highly desirable for the reasons discussed earlier, it may be desirable to limit the maximum size of these intravascular elements 16. It may be desirable not to over-expand the expandable removal elements 16. While some means for positively limiting radial expansion of the expandable intravascular removal element 16 have been detailed hereinabove, it may be desirable to provide additional safety mechanisms. For instance, it is to be noted that the expansion of the material removal element 16 shown in FIGS. 1, 4, and 5 is limited by contact between a proximal end 118 of the distal annulus 106 and the distal end 98 of the inner coil 94. The embodiments of the invention illustrated in FIGS. 6 through 9 provide constructions of removal element expansion limiting means which are included within the expandable elements 16 themselves. In addition, these Figures show some alternative constructions for the bearing surface 112, as indicated earlier.

In the construction 116 of FIG. 6, the distal end 98 of the inner coil 94 extends through and distally of the proximal annulus 104 and into the hollow interior of the material removal element 16 defined by the braided wires 102. This is the currently preferred embodiment of the material removal element radial expansion limiting means. The distal end 98 of the inner coil 94 extends into the interior of the material removal element 16 a specific, predetermined distance which limits the radial expansion of the braided wires 102 by a corresponding distance. In other words, the proximal end 118 of the distal annulus 106 of the construction 116 can travel a maximum distance smaller than the distance traveled by the proximal end 118 of the distal annulus 106 of the embodiments of FIGS. 1, 4, and 5 upon maximum proximal movement of the bead 120 and the guidewire 42. Contact between the proximal end 118 of the distal annulus 106 and the distal end 98 of the inner coil 94 positively limits axial compression and radial expansion of the material removal element 16. Once the proximal end 118 engages the distal end 98, the removal element 16 cannot be further axially compressed because the guidewire 42 and the bead 120 cannot be moved further proximally. Thus, the material removal element 16 of the construction 116 can radially expand a predetermined maximum distance smaller than the maximum distance of radial expansion of the material removal element 16 of the embodiments of FIGS. 1, 4 and 5.

Another construction 126 of the distal portion of the vascular occlusion material removal device 10 is shown in FIG. 7. This construction 126 utilizes material removal element radial expansion limiting means in the form of elongated windings 128 on a portion of the inner coil 94 that extend into the interior of the material removal element 16 in much the same manner as discussed hereinabove with respect to the construction 116. However, in this construction 126, the distal end 98 of the of the inner coil 94 is fixedly attached to the distal annulus 106 by solder, weld, braze or similar means. Thus, when the guidewire 42 is moved proximally and the fillet 122 engages the distal annulus 106, the expanded windings 128 within the hollow interior of the material removal element 16 are compressed until adjacent windings 130A and 130B on opposite sides of each of the expanded windings 128 contact each other. In this manner, the axial compression and the radial expansion of the braided material removal element 16 are positively limited by the sum of the distances between the adjacent windings 130A and 130B within the interior of the material removal element 16 when the material removal element 16 is in the relaxed, contracted position as shown.

Yet another embodiment of the material removal element radial expansion limiting means is shown in FIG. 8. Here, the means takes the form of two tubes 132 and 134, such as hypotubes and the like. The tube 132 is fixedly attached to an inner surface of the distal-most windings of the inner coil 94 by suitable means, such as adhesive, solder, braze or weld, and is also attached by similar means to the proximal annulus 104. This insures proper torque transfer from the drive shaft 92 to the material removal element 16. The tube 132 extends into the hollow interior of the material removal element 16 a certain, predetermined distance to locate a distal end 136 of the tube 132 within the hollow interior.

The tube 134 is fixedly attached to the distal annulus 106 by similar means, and extends proximally into the hollow interior of the material removal element 16 to locate a proximal end 138 of the tube 134 within the hollow interior. Thus, the distal end 136 of the tube 132 is offset from the proximal end 138 of the tube 134 by a predetermined distance which limits axial compression of the radially expandable material removal element 16. The tubes 132 and 134 both have inner diameters sufficient for accepting the guidewire 42 therethrough so that the material removal element 16 of this embodiment radially expands in the same manner as the other embodiments. As the guidewire 42 and the bump 124 move proximally, the bump 124 engages the distal annulus 106 and forces the distal annulus 106 and the tube 134 proximally. The braided wires 102 expand radially until the distal end 136 of the tube 132 contacts the proximal end 138 of the tube 134. This contact positively limits radial expansion of the material removal element 16. Thus, the lengths of both tubes 132 and 134 and the distance between the distal end 136 and the proximal end 138 determine the maximum radial expansion of the material removal element 16.

An additional embodiment of the material removal element radial expansion limiting means is contained in the construction 140 of FIG. 9. Here, the tube 134 is eliminated and the tube 132 is elongated with respect to the embodiment of FIG. 8. When the material removal element 16 is expanded fully, the proximal end 118 of the distal annulus 106 engages the distal end 136 of the tube 132. Thus, the length of the tube 132 and the distance between the distal end 136 of the tube 132 and the proximal end 118 of the distal annulus 106 within the hollow interior of the material removal element 16 determine and positively limit the maximum radial expansion of the material removal element 16.

In some cases, it may be desirable to perform balloon angioplasty in conjunction with vascular occlusion material removal. Because of this desire, another embodiment of the invention, an expandable intravascular occlusion removal device 142, is provided and is shown in FIG. 10. The removal device 142 is substantially similar to the removal device 10, except for the differences noted in the following paragraphs, hence the like reference numerals for similar structures. While the removal device 142 is illustrated as having the lock knob 54 and the thumb pad 66, it is to be remembered that the elements of the various embodiments of the invention can be combined in any desired fashion.

The removal device 142 includes a manifold assembly 144 and a catheter assembly 146 which differ from the catheter assembly 14 and the manifold assembly 22. Specifically, the manifold assembly 144 includes a third port 148 located distally of the port 82. The port 148 is connectable with a suitable source of fluid, not shown, but known in the art, for supplying the catheter assembly 146 with fluid to dilate a dilating member 158 for performing balloon angioplasty. The port 148 is located distally of a proximal end 150 of the catheter assembly 146.

The catheter assembly 146 includes a catheter sheath 152 having at least two lumens: a drive shaft lumen 154 and a fluid inflation lumen 156. The drive shaft 92 extends through the drive shaft lumen 154 from the distal end 34 of the drive shaft 26 to the proximal annulus 104, and the drive shaft lumen 154 can be utilized for infusion and aspiration in much the same manner as the catheter sheath 90 can. The drive shaft lumen 154 extends substantially the entire length from the manifold assembly 144 to the proximal annulus 104.

A dilating member 158, constructed substantially similarly to an angioplasty balloon, is located on the catheter assembly 146 offset proximally of a distal end 160 of the catheter assembly 146 and the distal end of the drive shaft lumen 154. The inflation lumen 156 extends from the port 148 to a proximal end 162 of the dilating member 158 and conveys fluid from the fluid source, conventionally referred to as an inflation device, to and from the dilating member 158, thereby causing the dilating member 158 to inflate and deflate. To facilitate intravascular location of the dilating member 158, a radiopague marker band 164 is provided on the outer surface of the drive shaft lumen 154, thereby rendering the intravascular portion of the dilating member 158 radioscopically visible to a treating physician. Intravascular inflation of the dilating member 158 provides added stability to the distal portion of the removal device 142 during operation thereof, while also allowing the treating physician to occlude blood flow through the vascular lumen being treated and further allowing the physician to perform balloon angioplasty if desired. With the removal device 142 it is possible for a treating physician to cut, remove, and/or angioplasticly displace vascular occlusion material while only using a single piece of equipment.

Yet another embodiment 176 of an expandable intravascular occlusion material removal device is illustrated in FIG. 12. This embodiment 176 is substantially similar to the devices 10 and 142 described hereinabove, except for the differences detailed below, hence the like reference numerals for similar structures. The device 176 uses the same material removal element 16 and substantially the same drive assembly 12 as described earlier. However, because the device 176 does not use the guidewire 42 to move the removal element 16 between the contracted and the expanded positions, certain modifications can be made to the drive assembly 12. With the removal device 176, the removal element 16 is moved between the expanded position of FIG. 14 and the contracted position of FIG. 13 by axial movement of a catheter assembly 178 with respect to the drive shaft 92.

The drive assembly 12 comprises the housing 36 containing the motor 24, the power source 28, and the control switch 30. The housing 36 may be formed from a suitable material, such as polycarbonate, polyethylene or the like. In an exemplary embodiment of the removal device 176, the drive motor 24 may be a direct current micromotor, such as those disclosed hereinabove, which can produce a start up torque of about 2.6 ounce-inch and a no-load torque of about 0.015 ounce-inch. The drive motor 24 may have a speed range of about 5,000 to about 100,000 revolutions per minute, with a speed of about 20,000 revolutions per minute being the currently preferred operating speed of the device 176.

The drive motor 24 has the hollow drive shaft 26 so that the guidewire 42 can pass therethrough, thereby allowing the removal device 176 to be delivered over the guidewire 42. In an exemplary embodiment, the guidewire 42 may be substantially similar to guidewires used for percutaneous transluminal coronary angioplasty, although other guidewires may also be used. In some embodiments, at least a portion of the guidewire 42 may be coated with a silicone impregnated or fluoropolymer infused nickel material, such as nedox, or a nickel-silver alloy, such as nikasil and the like, to reduce friction between the guidewire 42 and the inner coil 92. If desired, a structure similar to that provided by the inner sheath 40 or the outer sheath 58 may be provided between the proximal end 32 of the drive shaft 26 and the aperture 44 in the housing 36 to direct the guidewire 42 from the proximal end 32 of the drive shaft 26 to the aperture 44.

In addition, the guidewire lock mechanism 50 illustrated in FIGS. 1 through 3 and 10 may also be provided, if desired, adjacent the aperture 44 to fix the guidewire 42 with respect to the removal device 176.

The distal end 34 of the drive shaft 26 extends through the aperture 38 in the housing 36 and is connected by suitable means, such as solder, braze and the like, to the proximal end of the drive shaft 92. A seal may be provided adjacent the aperture 38 through which the drive shaft 26 sealingly passes to limit fluid flow into the housing 36. Another seal may be provided within the drive shaft 26 adjacent the aperture 38 through which the guidewire 42 can sealingly pass to further limit fluid flow into the housing 36. While this embodiment 176 is shown in FIG. 12 as not including a manifold assembly, it is to be recognized that the embodiment 176 can employ a manifold assembly, such as the manifold assemblies 22 (FIG. 1) or 144 (FIG. 10). The addition of a manifold assembly, possibly along with addition of appropriate lumens and other structures in the catheter assembly 178, can enable the removal device 176 capable of providing irrigation, drug delivery, aspiration, etc. The removal device 176 can also include the dilation member 158.

The housing 36 includes a shoulder member 180 extending from the housing 36 and surrounding the aperture 38 and the portion of the drive shaft 26 extending distally of the aperture 38. The shoulder member 180 may be substantially cylindrical in shape. A portion of the outer surface of the shoulder member 180 includes threads or grooves 182, the significance of which will be discussed later, which extend substantially diametrically inward on the outer surface of the shoulder member 180. The grooves 182 are part of a removal element expansion control mechanism 184 for positively moving the removal element 16, located at a distal end of the drive shaft 92, between the contracted and expanded positions.

In an exemplary embodiment, the inner coil 94 may be a tri-filar coil of 0.005" diameter 304 stainless steel wire. The inner coil 94 may have an inner diameter of about 0.0165" and an outer diameter of about 0.0265". These dimensions allow the removal device 176 to be delivered over a guidewire 42 having a diameter of about 0.010" to 0.014". The choice of guidewire 42 outer diameter may depend upon utilization of aspiration. The axial length of the inner coil 94 may be about 140 cm, but other lengths are possible if desired. The inner coil 94 may be provided with various pre-load options, e.g. to reduce torsional flexibility and increase torsional rigidity of portions of the drive shaft 92, by known methods. The pre-load options of the inner coil 92 are chosen such that the inner coil 94 can efficiently deliver torque to the removal element 16 while also being able to navigate through a vascular lumen over a guidewire 42 and to effectively move the removal element 16 between the contracted and expanded positions. For instance, by pre-loading or axially twisting a wire during formation of a portion of the coil 92, that twisted portion can have increased rigidity as compared to another portion of the coil 92. The portion having increased rigidity can facilitate pushability of the removal device 176 while the other portion of the coil 92, having less rigidity, can facilitate trackability of the device 176.

The coating 100 may be provided, e.g. in the form of a 0.002" thick heat shrink fluoropolymer tube which is applied to the outer diameter surface of the drive shaft 92 along its entire axial length. However, the coating 100 may not cover the distal end 98 of the inner coil 94, the significance of which will become clear later. The length of the coating 100 may be chosen to determine the location of an irrigation port on a distal portion of the drive shaft 92. In an exemplary embodiment, the braid 96 may be formed from eight 0.002" diameter 304 stainless steel wires braided at about 40 pics per inch. The braid 96 may be about 100 cm long, and is tensioned and attached to the outer diameter surface of the inner coil 94 as discussed earlier. Because the braid 96 may not be as long as the inner coil 94, the outer diameter or profile of the drive shaft 92 reduces distally of a distal end 186 of the braid 96. Thus, the profile of the portions of the catheter assembly 178 distal of the distal end 186 can also be correspondingly reduced. This reduced profile can increase the accessibility of some vascular occlusions to the removal device 176.

The catheter assembly 178 includes a catheter shaft 188 which surrounds the length of the drive shaft 92 substantially from the distal end 34 of the drive shaft 26 to the proximal end of the removal element 16. In an exemplary embodiment, the catheter shaft 188 may be a 0.002" thick tube of a suitable polymeric material, such as KYNAR and the like, and may be about 135 cm long. The catheter shaft 188 may be provided in other lengths. For example, the proximal portion of the catheter shaft 188, measuring about 100 cm, may have an outer diameter of about 1.3 mm, while a distal portion thereof, measuring about 35 cm, may have an outer diameter of approximately 1 mm. The juncture between the proximal and distal portions of the catheter shaft 188 is adjacent the distal end 186 of the braid 96 or the outer coil of the drive shaft 92.

A proximal end 190 of the catheter shaft 188 is attached to an inner diameter surface of a strain relief tube 192 by a suitable adhesive, such as a cyanoacrylate, urethane or similar adhesive. The strain relief tube 192 may be substantially cylindrical and may have a thickness of about 0.003" and an axial length of about 4 cm. The strain relief tube 192 may be made from a suitable polymeric material, such as a nylon-polyether blend like PEBAX (France) and the like. The strain relief tube 192 is of suitable construction for absorbing strains on the catheter assembly 178.

The outer diameter surface of the strain relief tube 192 is attached to an adjustment member 194 by a suitable adhesive, such as a cyanoacrylate, a urethane, or the like. The adjustment member 194 may be made from a suitable polymeric material, such as polycarbonate, polyurethane and the like, and may be substantially cylindrical in configuration. The adjustment member 194 has an inner diameter sufficient so that the adjustment member 194 can surround the drive shaft 92, the shoulder portion 180, the catheter shaft 188 and the strain relief tube 192. A suitable seal may be disposed between the outer surface of the shoulder portion 180 and the inner surface of the adjustment member 194 to limit fluid from flowing between the shoulder portion 180 and the adjustment member 194.

The adjustment member 194 cooperates with the shoulder portion 180 to form the expansion control mechanism 184 for positively moving the removal element 16 between the contracted position of FIG. 13 and the expanded position of FIG. 14. Specifically, at least one tab 196 extends substantially diametrically inward from the inner surface of the adjustment member 194 towards the outer surface of the shoulder portion 180. The tab 196 has a configuration complementary to the configuration of the grooves 182 on the outer surface of the shoulder portion 180 so that the tab 196 can be inserted into and mate with the grooves 182. The tab 196 can be shifted out of one groove 182 and into an adjacent groove 182 by application of a suitable force to the adjustment member 194. To facilitate shifting of the tab 196 between adjacent grooves 182, the adjustment member 194 has an actuating portion 198 having a configuration adapted for accepting force manually applied by a treating physician.

By applying an appropriate force to the actuating portion 198, the physician can move the tab 196 between adjacent grooves 182 on the shoulder portion 180. The adjustment member 194 moves in unison with the tab 196, which also causes corresponding movement of the strain relief tube 192 and the catheter shaft 188. Because the tab 196 and the adjustment member 194 move axially with respect to the grooves 182 and the shoulder portion 180 responsive to application of forces by the treating physician to the actuating portion 198, the catheter shaft 188 conjointly moves axially with respect to the drive shaft 92. Relative axial movement of the drive shaft 92 and the catheter shaft 188 causes corresponding movement of the removal element 16 between the contracted position of FIG. 13 and the expanded position of FIG. 14. If the grooves 182 are thread-like, relative axial movement of the drive shaft 92 and the catheter shaft 188 may be accomplished by rotation of the adjustment member 194 about the shoulder portion 180. Scaling means 200 is also provided on the expansion control mechanism 184 for giving the treating physician a visual indication of the position of the removal element 16. The position of the removal element 16 may also be verifiable by radioscopic visualization techniques. It is to be noted that, in some alternative embodiments of the removal device 176, the expansion control mechanism 184 may be constructed so that catheter shaft 188 may be selectively detached from the drive assembly 12.

The construction of the distal end of the removal device 176 is more clearly illustrated in FIGS. 13 and 14. The inner coil 94 of the drive shaft 92 extends through the entire axial length of the removal element 16. The distal end 98 of the inner coil 94 is attached to the distal annulus 106 within the aperture 110 by suitable means, such as braze, solder or the like, as discussed earlier with respect to attachment of the wires 102 to the annuluses 104 and 106. In this embodiment 176, however, it is to be recognized that the guidewire 42 does not have a bearing surface 112 and that the aperture 110 in the distal annulus 106 may be of sufficient size to allow withdrawal of the guidewire 42 therethrough. This is a distinction over the previously-discussed embodiments of the invention and is possible because the guidewire 42 is not used to move the removal element 16 between the collapsed position and the expanded position. However, in some circumstances, it may be desirable to have a guidewire 42 which cannot be withdrawn from the removal device 176 during operation thereof, such as when it is desirable to retain the removal element 16 on the guidewire 42. With this embodiment 176, it may not be necessary to have a non-occluded lumen within the vasculature of sufficient size to accept the coil 114 or distal portions of the guidewire 42 in order to remove occlusion material with the removal device 176.

Proximal ends 202 of the wires 102 are attached to an annular expansion bearing surface or member 204 by suitable means, such as a weld, braze, solder or the like. In an exemplary embodiment, the proximal ends 202 are brazed to the bearing member 204 with a Turbo braze paste available from Turbo Braze Corporation of Union, N.J. The bearing member 204 cooperates with a complementary bearing surface or member 206 attached to a distal end 208 of the catheter shaft 188 by a suitable adhesive, such as a cyanoacrylate, urethane, or other adhesive. In an exemplary embodiment, the bearing members 204 and 206 may comprise 21XX hypotubes formed from 304 stainless steel and available from Micro Group, Inc. of Medway, Mass.

The bearing members 204 and 206 have complementary configurations such that one member 204 or 206 can freely rotate within the other member 204 or 206. For instance, the bearing members 204 and 206 may be flared and necked-down, respectively, to facilitate relative rotation of the members 204 and 206. In the illustrated embodiment, the bearing member 204 has a relatively large outer diameter portion 210 and a relatively small outer diameter portion 212 with the portion 210 being located distally of the portion 212. The wires 102 are attached to the outer surface of the portion 210 and the bearing member 204 has a constant inner diameter to accept the inner coil 94. In some embodiments of the removal device 176, the bearing member 204 may be substantially cylindrical in configuration having constant inner and outer diameters. The bearing member 206 has a relatively large inner diameter portion 214 and a relatively small outer diameter portion 216 with the portion 214 being located distally of the portion 216. The outer diameter of the portion 216 is substantially equal to the inner diameter of the distal end 208 of the catheter shaft 188 to insure a firm connection between the catheter shaft 188 and the bearing member 206. The inner diameter of the portion 214 of the bearing member 206 is slightly larger than the outer diameter of the portion 212 of the bearing member 204. Thus, the portion 212 of the bearing member 204 is insertable into the portion 214 of the bearing member 206. Accordingly, when the motor 24 is energized, the bearing member 204 can rotate within the bearing member 206. In some embodiments of the device 176, a lubricous or low friction substance 217, such as a fluoropolymer, nedox and the like, may be coated onto the outer surface of the portion 212 and the inner surface of the portion 214, as well as other mating surfaces, to facilitate rotation of the bearing member 204 within the bearing member 206. It is to be appreciated that, in other embodiments, the bearing member 206 may rotate within the bearing member 204. Any construction of the bearing members 204 and 206 is possible as long as the proximal end of the removal element 16 is capable of free-wheeling movement with respect to the catheter shaft 188.

Further structural details of the embodiment 176 may become more clear with reference to the following discussion of the operation thereof. Again, it is to be noted that the elements of each of the embodiments 10, 142 and 176 of the invention may be combined in any suitable fashion to produce a vascular occlusion material removal device having desired properties. For instance, it is to be recognized that any of the embodiments of the material removal element expansion limiting means may be included with the removal device 176. The removal device 176 functions substantially similarly to the removal devices 10 and 142 disclosed earlier except for the method of moving the removal element 16 between the contracted and expanded positions. Thus, the discussion of operation of the removal device 176 will be limited to the method of expanding the removal element 16.

It is to be noted that, in the contracted position, the adjustment member 194 is positioned closest to the drive assembly 12. With the removal element 16 in the contracted position of FIG. 13, a treating physician wishing to move the removal element 16 towards the expanded position (FIG. 14) applies a suitable force to the actuation portion 198 of the adjustment member 194. This force removes the tab 196 from the proximal-most groove 182 and shifts the tab 196, along with the adjustment member 194, distally along the shoulder portion 180. As the adjustment member 194 moves distally along the shoulder portion 180, the strain relief tube 192 and the catheter shaft 188 also conjointly move axially with respect to the drive shaft 92 in the distal direction.

Because the distal end 98 of the drive shaft 92 is fixed to the distal annulus 108 and the removal element 16, distal axial movement of the catheter shaft 188 with respect to the drive shaft 92 reduces the axial distance between the distal annulus 108 and the bearing members 204 and 206. The bearing member 206 transmits force from the catheter shaft 188 to the bearing member 204, and, from there, to the wires 102. Opposite ends of the braided wires 102 are attached to the distal annulus 108 and the bearing member 204, respectively, such that reduction of the axial distance between the distal annulus 108 and the bearing member 204 causes the wires 102 to bow radially outwardly from the inner coil 94 of the drive shaft 92.

In this manner, the removal element 16 moves between the contracted position of FIG. 13 and the expanded position of FIG. 14. Because the removal element 16 moves between the contracted and expanded positions responsive to movement of the catheter shaft 188, the scaling means 200 provides the treating physician with a visual indication of the diameter defined by the wires 102. It is to be noted that this removal element 16 expanding movement of the catheter shaft 188 can also be viewed, from a suitable reference frame, as the drive shaft 92 shifting with respect to the removal element 16. Therefore, it is equally valid to refer to expansion of the removal element 16 responsive to movement of the drive shaft 92 or the catheter shaft 188 with respect to the removal element 16.

Once the desired positioning of the removal element 16 is achieved, the treating physician releases the actuation portion 198, and the tab 196 comes to rest in a groove 182. This locks the removal element 16 in the desired position. If it is desired to move the removal element 16 back towards the contracted position, the above-discussed steps are repeated, but the direction of the force applied to the actuating portion 198 of the adjustment member 194 is reversed to cause movement of the adjustment member 194 and the catheter shaft 188 proximally towards the drive assembly 12.

Figure 17:
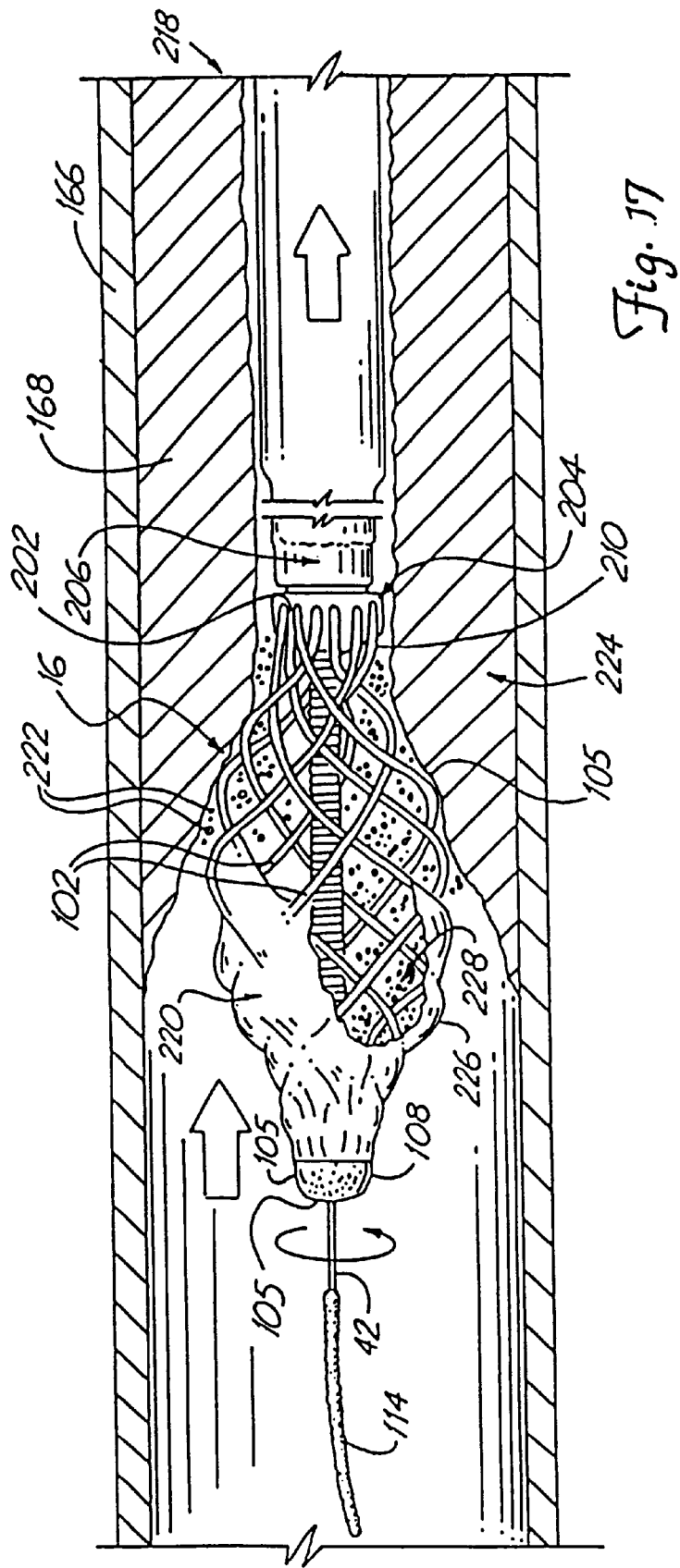
FIG. 17 is a sectional view of an alternative embodiment of a vascular occlusion material removal device expanded distally of an occlusion and moved towards the occlusion to remove occlusion material.

Yet still a further embodiment 218 of the invention is illustrated in FIG. 17. The embodiment 218 is substantially similar to the embodiment 176 except for the differences noted below, hence the like reference numerals for similar structures. The embodiment 218 differs from the embodiment 176 in that the removal element 16 includes a collection portion 220 for collecting occlusion particulate 222 removed from a vascular occlusion 224. The collection portion 220 may be provided with the removal devices 10 and 142 as well. Also, it is to be recognized that, while the collection portion 220 is illustrated in FIG. 17 as being disposed on a distal end of the removal element 16, the collection portion 220 may alternatively be disposed on the proximal end of the removal element 16. Generally, the collection portion 220 is located on the removal element 16 at a position where particulate 222 from the occlusion 224 may be collected, and thus, the disposition of the collection portion 220 may depend upon whether the removal element 16 is to be moved proximally or distally against the occlusion 224.

In the illustrated embodiment of the removal device 218, the collection portion 220 is disposed on a distal portion of the removal element 16 so that particulate 222 removed from the occlusion 224 will naturally move towards the collection portion 220 under the influence of fluid flow through the vasculature. Movement of particulate 222 into the collection portion 220 can further be insured by utilizing the removal device 218 to remove occlusion material while being moved proximally across the occlusion 224, viz. in a direction opposite to the direction of fluid flow through the lumen. This method of operation of the removal device 218 will be discussed in greater detail later. In an alternative embodiment of the removal device 218, fluid may be provided through the drive shaft 92 and/or the catheter shaft 188 so that this fluid flow can direct particulate 222 into the collection portion 220. The fluid may be filtered by a retention member or coating 226 forming the collection portion 220 and may be able to exit the collection portion 220 through the aperture 110 in the annulus 106. Because the collection portion 220 is disposed on the distal portion of the removal element 16, it may not be desirable to place abrasive 105 on the portions of the wires 102 forming the collection portion 220.

In an exemplary embodiment of the removal device 218, the collection portion 220 may be formed by a retention member in the form of a polymeric coating 226, such as polyurethane, Pellathane™ (Dow Chemical) and the like, disposed on the distal portion of the removal element 16. The polymeric coating 226 may be applied to the wires 102 in a number of ways, such as by dipping the removal element 16 in the polymer, spraying the polymer onto the wires 102 with, for example, an air brush, directly applying the polymer to the wires 102, etc. The coating 226 is applied to the wires 102 such that at least the outer surfaces of the wires 102 are coated, and so that, when the removal element 16 is moved into the expanded position, the coating 226 will stretch across and cover spaces between adjacent wires 102. In this manner, the coating 226 forms a boundary of a particulate collection chamber 228 located at the interior of the removal element 16. It is to be noted that, in some embodiments of the removal device 218, the collection portion 220 may not be formed from a polymeric coating 226, but may be formed from a fabric or filter-like material, such as GORTEX and the like, or a polypropylene screening material. In general, the collection portion 220 is formed from any suitable material having apertures whose diameters measure about 5 microns. These apertures may allow blood or other fluid to pass distally through the collection portion 220 while retaining occlusion particulate 222 larger than 5 microns within the collection portion 220. In some embodiments, the collection portion 220 may be able to occlude fluid flow. These embodiments of the collection portion 220 may facilitate removal of occlusion particulate by aspiration because fluid would not flow beyond the collection portion 220. Thus, the scope of the claims is not to be limited by the above-discussed constructions of the collection portion 220.

The various embodiments 10, 142, 176 and 218 of the present invention also provide a number of methods for performing intravascular treatments, such as removing or displacing vascular occlusion material. These methods comprise a plurality of steps, some of which have been discussed in detail already, so the following discussion of the methods will simply refer back to those detailed discussions, instead of restating them, where appropriate. As with the mechanical elements of the embodiments 10, 142, 176 and 218 of the invention, the steps of the methods may also be combined in suitable fashion to perform a desired treatment.

The expandable intravascular occlusion material removal device 10, 142, 176 or 218 is inserted into the patient's vascular system through a suitable puncture or other access site, such as via the femoral artery, in well known fashion. At this point, the expandable material removal element 16 is in the radially contracted position shown in FIG. 4. Because the removal device 10, 142, 176 or 218 has a low profile when the material removal element 16 is in the contracted position, the intravascular portion of the removal device 10, 142, 176 or 218 can be inserted through a conventional 7 French guide catheter, well known to those having ordinary skill in the relevant art. The removal device 10, 142, 176 or 218 is moved over the medical guidewire 42, which has been previously positioned in proximity to the intravascular treatment site, until the distal end of the annulus 106 is adjacent the proximal end of the bearing surface 112, if present, as discussed hereinabove. Now, the expandable material removal element 16, currently in the contracted position, is located in close proximity to the vascular occlusion material to be removed thereby.

At any time, a fluid, such as saline, a drug therapy, heparinized saline, an oxygenated fluid, such as FLUORSOL, and the like, can be applied to the port 80 on the manifold assembly 22 or 144 from a suitable fluid source. The fluid flows through the port 80 and into the portion of the main lumen 78 located between the fluid seal 84 and 86, and from there, through the aperture 88 into the hollow interior of the drive shaft 92. The fluid flows along the axial length of the drive shaft 92 and passes into the hollow interior defined by the braided wires 102 of the expandable material removal element 16. The fluid can flow through spaces between adjacent portions of the braided wires 102 to infuse the intravascular treatment site with fluid. Alternatively, with the embodiment 176, the fluid may flow through the aperture 110 in the distal annulus 106. Also, the location at which the fluid exits the drive shaft 92 may be predetermined by appropriately choosing the length of the coating 100. This may provide for maintenance of fluid within a vascular lumen if aspiration is used.

At any time, another fluid to be infused into the patient, or a negative pressure to aspirate the intravascular treatment site may be applied to the port 82 from a suitable source. The fluid or the negative pressure is applied through the port 82 to the hollow interior of the catheter sheath 90, 152 or 188 and from there to the vascular lumen adjacent the distal end 18, 160 or 208 of the catheter assembly 14, 146 or 178, respectively. Because of the relative locations of the distal ends of the drive shaft 92 and the catheter sheath 90, 152 or 188, as discussed earlier, effective aspiration of the treatment site may be provided. This is important because some vascular occlusion material, such as certain types of thrombus, may be removed from a vascular surface or another occlusion simply by aspiration.

In some other embodiments of the removal device 10, 142, 176 and 218, aspiration may be provided by an impeller-like element operatively attached to the drive shaft 92 such that rotation of the drive shaft 92 and the impeller element generates a fluid flow within the vascular lumen, thereby causing particulate 222 to flow into the catheter sheath 90, 158 or 188. In other embodiments, multiple impeller-like elements may be attached to the shaft 92 at various locations along the longitudinal axis thereof.

If desired, the removal devices 10, 142, 176 or 218 may be delivered through another catheter, such as the guide catheter discussed earlier. If this is done, fluid may be provided through the drive shaft 92 and/or through the catheter sheath 90, 152 or 188. This fluid may generate a positive pressure within the vascular lumen. At the same time, a negative pressure may be provided through the guide catheter. This could produce a pressure differential within the vascular lumen which could force fluid and occlusion particulate 222 proximally through the guide catheter and out of the patient's body. This method may also be used to force fluid and occlusion particulate 222 proximally through the catheter sheath 90, 158 or 188. In still other embodiments, a dilation member may be provided at the distal end of the guide catheter, and/or another dilation member, similar to an angioplasty balloon may be located distally of the removal element 16. By intravascularly inflating both of these dilation members, the intravascular treatment site may be substantially isolated, which can facilitate particulate 222 removal.

With the expandable material removal element 16 being positioned with respect to the vascular occlusion material to be removed, treating physician can expand the material removal element 16 to the desired degree by implementing the methods discussed earlier with respect to the guidewire lock mechanism 50 and the material removal element expansion control mechanism 52 for the embodiments 10 and 142, and with respect to the expansion control mechanism 184 for the embodiments 176 and 218. The material removal element 16 can be moved into a plurality of positions by variably expanding and/or contracting the material removal element 16. Thus, multiple material removal element 16 sizes, shapes, profiles and characteristics may be achieved with the use of a single occlusion material removal device 10, 142, 176 or 218. The controlled, incremental expansion and contraction of the expandable material removal element 16 can provide a treating physician with greater flexibility in performing intravascular treatments, as well as possibly reducing the costs of such treatments because multiple pieces of equipment need not be used. This is a significant improvement over some of the intravascular treatment devices of the prior art. In addition, the various constructions of the material removal element radial expansion limiting means may insure that the material removal element 16 is not over-expanded.

With the removal device 142, either before of after expansion of the expandable material removal element 16, the dilating member 158 can be inflated to a suitable pressure by application of a pressurized fluid to the port 148, as discussed above. The pressurized fluid flows through the port 148 and the lumen 156, and into the interior of the dilating member 158. The dilating member 158 expands sufficiently so that an outer surface thereof engages the interior surface of the vascular lumen. The dilating member 158 can be inflated to pressures on the order of 4 to 8 atmospheres and can center and stabilize distally-located portions of the removal device 142 during operation thereof. Inflation of the dilating member 158 can also be used to occlude blood flow through the vasculature being treated.

The removal device 10, 142, 176 or 218 is now ready to remove vascular occlusion material from a vascular surface or from a vascular occlusion by expansion and/or rotation of the expandable material removal element 16. It is to be noted that, because the expandable material removal element 16 is comprised of braided wires 102 which define spaces between adjacent wires 102, expansion of the material removal element 16 may not occlude fluid flow through the vascular lumen. For example, fluids infused into the vasculature by the device 142 at a location distally of the dilating member 158 can flow around and through the spaces between the braided wires 102 and continue through the patient's vasculature distally of the material removal element 16.

If the occlusion material were located radially above the material removal element 16, then appropriate expansion of the wires 102 can allow the abrasive 105 or other cutting surface on the wires 102 to bite into a portion of the occlusion material. This radial cutting of the wires 102 into the vascular occlusion material can cause a portion of the material to pass through spaces between adjacent wires 102 and be captured in the hollow interior of the material removal element 16 defined by the wires 102. The expansion of the braided wires 102 defines a radially directed cutting vector for severing occlusion material. The effectiveness of this radial cutting may depend upon the composition or hardness of the vascular occlusion material. If desired, the expandable material removal element 16 can be moved into the contracted position, thereby trapping occlusion material within the hollow interior defined by the braided wires 102. The material removal element 16 can be removed from the patient's vasculature if desired and the occlusion material will be retained within the hollow interior of the material removal element 16 because of the spring-like forces inherent in the wires 102. With the removal device 218, retention of occlusion material within the collection chamber 228 within the hollow interior of the braided wires 102 is enhanced by the coating 226. The captured material can be later retrieved for performing a biopsy or other procedure on the material.

Some occlusion material may not be susceptible to removal in this fashion. For instance, some occlusion material may be relatively hard or calcified, thereby making it rather difficult for the wires 102 to bite into the material upon expansion of the material removal element 16. If this is the case, then the material removal element 16 can be expanded such that the outer surfaces of the braided wires 102 contact the interior surface defined by the occlusion. In other words, the material removal element 16 is expanded to define a cutting diameter slightly larger than a non-occluded diameter of a particular portion of the vasculature. By expanding the diameter of the removal element 16 to a size slightly larger than the non-occluded diameter of the vascular lumen, more effective and more efficient removal of occlusive material is provided as compared to some prior art methods where a cutting element is expanded to define a diameter equal to that of the vascular lumen. The material removal element 16 is expanded and is locked in this expanded position according to the methods described earlier with respect to the guidewire lock mechanism 50 and the material removal element expansion control mechanism 52 for the embodiments 10 and 142, and with respect to the expansion control mechanism 184 for the embodiments 176 and 218. The maximum radial expansion of the material removal element 16 is limited by the radial expansion limiting means discussed hereinabove.

Once locked in the expanded position, the treating physician actuates the control switch 30, thereby energizing the motor 24. The motor 24 induces rotation of the drive shaft 26, which, in turn, causes the drive shaft 92 to rotate within the catheter sheath 90, 152 or 188. The material removal element 16 is also rotated conjointly with the drive shafts 26 and 92. The rotation of the material removal element 16 enables the sharp edges or abrasive 105 particles on the surfaces of the braided wires 102 to cut, abrade, ablate, or otherwise remove vascular occlusion material from a vascular lumen surface or a vascular occlusion.

Rotation of the braided wires 102 defines a cutting vector directed tangentially to the surface interface between a given wire 102 and the occlusion material. The removed occlusion material can pass through the spaces between adjacent wires 102 and be caught in the collection chamber 228 or the hollow interior defined by the braided wires 102 comprising the material removal element 16. This removed material can be trapped within the material removal element 16 upon contraction thereof, as described earlier, and subsequently removed from the patient's vasculature along with the material removal element 16. With the embodiment 218, the coating 226 can facilitate retention of particulate 222 within the chamber 228. Alternatively, the removed vascular occlusion material can be drawn into the interior of the catheter sheath 90 or 152 by means of negative pressure applied to the port 148. Thus, there are at least three ways by which removed vascular occlusion material can be carried away from the patient's vasculature.

After a sufficient amount of vascular occlusion material has been removed by rotation of the material removal element 16, the non-occluded diameter of the vascular lumen is enlarged, but further occlusive material may remain within the vascular lumen. It may be desirable to remove more occlusion material, thereby further enlarging the non-occluded diameter of the vascular lumen. To do this, the expandable material removal element 16 is further radially expanded, according to the steps of the method discussed earlier, to define a cutting diameter slightly larger than this second, non-occluded diameter of the vascular lumen. This process of expanding the cutting diameter of the material removal element 16 progressively—starting small and finishing large—can be repeated as often as necessary until a non-occluded diameter of the desired length is formed in the vascular lumen. This progressive cutting process allows for more efficient removal of the occluding material by always using a cutting diameter just slightly larger than the non-occluded diameter. The expandable nature of the material removal element 16 allows this process to be executed while utilizing only one intravascular device 10, 142, 176 or 218. Also, this process can be used in conjunction with moving the device 10, 142, 176 or 218 either distally or proximally against the occlusion.

It is possible that a particular vascular lumen might have more than one occlusion which may be located distally of a first occlusion. If this is the case, after sufficient material of the first occlusion is removed to revascularize that portion of the lumen, then the material removal element 16 can be repositioned intravascularly adjacent a second occlusion for removing its occluding material. To reposition the material removal element 16, the dilating member 158, if inflated, should be deflated. The material removal element 16 should also be moved into the contracted position. The material removal element 16, the dilating member 158 and the distal portion of the catheter assembly 14, 146 and 178 assume a low profile for facilitating intravascular movement of the removal device 10, 142, 176 or 218. The entire removal device 10, 142, 176 or 218 can now be freely repositioned for removing material from the second occlusion. It is envisioned that, in some embodiments of the invention, the drive shaft 92 and the cutting element 16 may be axially shiftable with respect to the catheter sheath 90, thereby facilitating intravascular repositioning of the removal element 16.

Once properly positioned adjacent the second occlusion, the material removal element 16 can be expanded as before and the same process of occlusion material removal can be performed. There may be some occlusions, however, which define a non-occluded diameter smaller than the outer diameter defined by the braided wires 102 in the contracted position. With the removal devices 176 and 218, the guidewire 42 may be withdrawn sufficiently such that the cutting surface 108 on the distal annulus 106 can engage and remove occlusion material. However, if the non-occluded diameter were large enough to accept the coil 114 of the guidewire 42 and the bearing surface 112, if present, then the occlusion material can still be removed by the material removal element 16. In this case, the coil 114 of the guidewire 42 and the bearing surface 112, if present, are passed through the non-occluded diameter sufficiently to bring the cutting surface 108 on the distal annulus 106 into contact with a proximal end of the occlusion. The cutting is surface 108 has a configuration or an abrasive 105 coating which facilitates removal of vascular occlusion material upon rotation of the distal annulus 106. In addition, as the Figures show, the cutting surface 108 is tapered so that a relatively smaller cutting diameter encounters the occlusion material initially.

The motor 24 is energized, thereby rotating the material removal element 16 and the distal annulus 106, and the cutting surface 108 begins to bore through the occlusion material. The cutting action of the cutting surface 108 is directed substantially longitudinally or axially within the vascular lumen, and the cutting surface 108 can grind away occlusion material from the occlusion or the vascular surface, thereby increasing the size of the non-occluded diameter in the vascular lumen. Of course, aspiration can be used to carry the removed material away from the patient. The treating physician can apply an axially directed force to the removal device 10, 142, 176 or 218 as the cutting surface 108 rotates to move the cutting surface 108 distally through the occlusion. Since the cutting surface 108 is tapered, a progressively larger cutting diameter is engaged against the vascular occlusion as the cutting surface 108 and the associated removal device 10, 142, 176 or 218 are moved distally within the vascular lumen. Thus, the cutting surface 108 also executes substantially the same occlusion material removal process described above by starting with a small cutting diameter and gradually increasing that diameter as progressively more occluding material is removed.

The cutting surface 108 is rotated against the occlusion and simultaneously advanced distally with respect to the occlusion to form an enlarged diameter pilot hole longitudinally through the occlusion. This process is illustrated in FIG. 15 with respect to the removal device 176. As more proximal portions of the cutting surface 108 encounter the occlusion material, the cutting surface 108 may cut occlusion material along vectors directed tangentially to the interface of the cutting surface 108 and the occlusion. It is to be noted that a proximal-most portion of the cutting surface 108 defines an outer diameter substantially equal to the outer diameter defined by the braided wires 102 when in the contracted position, as shown in FIG. 15. Thus, the pilot hole formed by the cutting surface 108 has dimensions sufficient for accepting the material removal element 16 in the contracted position. Therefore, once this pilot hole has been formed, the motor 24 can be stopped, which ceases rotation of the material removal element 16 and the cutting surface 108. The expandable material removal element 16 can be positioned within the pilot hole and the dilating member 158, if provided, can be expanded to provide added stability to the distally-located portions of the device 142 or to occlude blood flow through the vascular lumen. At this point, the expandable material removal element 16 can be expanded, according to the above-discussed processes, within the pilot hole so that the braided wires 102 engage the occlusion material. This method is substantially similar to that illustrated in FIG. 16 with respect to the embodiments 176. The spring-like properties of the wires 102 can allow the removal element 16 to conform to the configuration of the occlusion when expanded, as will be discussed in greater detail later. The motor 24 can again be energized, and the rotating material removal element 16 can remove additional occluding material. The removal elements 16 may be expanded while the motor 24 is running.

In any case, once sufficient occlusion material has been removed, it may be desirable to perform balloon angioplasty within the vascular lumen in order to displace any remnants of the occlusion. To perform both occlusion material removal and angioplastic displacement of an occlusion remnant, the removal device 142 is used. After the motor 24 and the rotation of the expandable material removal element 16 has been stopped, the material removal element 16 is moved into the contracted position so that the braided wires 102 of the removal device 142 define a low profile. If the dilating member 158 was expanded during operation of the material removal element 16, then it too should be deflated, by reversing the above-discussed pressure flow, so that the entire distal portion of the removal device 142 defines a low profile for facilitating intravascular movement of the removal device 142.

The catheter assembly 146 of the removal device 142 is shifted distally within the vascular lumen to locate the contracted dilating member 158 adjacent the remnants of the occlusion. The treating physician may have an easier time of properly positioning the dilating member 158 with respect to the occlusion remnants because the marker band 164 renders the position of the dilating member 158 radioscopically visible. Once proper position has been attained, the dilating member 158 can be inflated, as discussed above, to a sufficient pressure, typically on the order of 4 to 8 atmospheres, to displace the remnants and further revascularize the vascular lumen.

A further method of removing occlusion material begins with locating the removal element 16, in the contracted position, distally of the occlusion material. The removal element 16 is expanded, as described above, and is then shifted proximally in the lumen toward he occlusion. The removal element 16 may be energized such that the rotating removal element 16 removes occlusion material from a distal end of the occlusion upon contact with the occlusion. The removal element 16 can be moved proximally progressively until sufficient occlusion material has been removed to revascularize the lumen.

A variation of this method is illustrated in FIG. 17 with respect to the removal device 218. FIG. 17 shows the removal element 16 located distally of the occlusion 224. This location of the removal element 16 may be achieved if the non-occluded lumen through the occlusion 224 is sufficient to accept the removal element 16 in the contracted position, or by forming a pilot hole through the occlusion 224 as discussed hereinabove. The removal element 16 is moved towards the expanded position by operation of the expansion control mechanism 184 to deploy the wires 102 to remove occlusion material and to deploy the collection portion 220 to capture particulate 222.

Once expanded, the removal element 16 is energized and the element 16 and the removal device 218 are moved proximally against the occlusion 224. The wires 102 remove particulate 222 from a distal portion of the occlusion 224. Because the collection portion 220 is located distally of the abrasive-coated wires 102 and the occlusion 224, particulate 222 removed from the occlusion 224 moves towards the collection portion 220 under the influence of fluid flowing through the vascular lumen. As noted earlier, fluid may be supplied through the catheter shaft 188 to do this, although blood flow through the lumen may be sufficient.

As the particulate 222 is removed from the occlusion 224, the particulate 222 moves into the interior of the removal element 16 through the spaces between adjacent abrasive-coated wires 102 and into the collection chamber 228 defined by the retention member or coating 226. The coating 226 retains the particulate 222 within the collection chamber 228 while allowing fluid to flow therethrough. The energized removal element 16 is progressively moved proximally against the occlusion 224. The location of occlusion material removal, defined by contact between the abrasive-coated wires 102 and the occlusion 224, is always proximal of the location of particulate 222 collection, defined by the coating 226. Some, if not all, of the particulate 222 removed from the occlusion 224 should be collected within the collection portion 220. Thus, the collection portion 220 may reduce the amount of particulate 222 that floats away from the occlusion 224 and the removal device 218. Once sufficient occlusion material is removed, or once the collection portion 220 is filled with particulate 222, the removal element 16 can be moved towards the contracted position and removed from the patient. The coating 226 may insure that particulate 222 is retained within the collection portion 220.

According to another method for removing vascular occlusion material, the removal element 16 can be inserted into a vascular lumen and positioned proximally of an vascular occlusion. The removal element 16 can then be expanded, by use of the above-discussed methods, to a certain diameter, such as the diameter of a non-occluded portion of the lumen, and advanced within the lumen towards the occlusion. The removal element 16 is forced into contact with the occlusion, and the wires 102 forming the expanded element 16 bite into the occlusion material. The removal element 16 is then retracted from the occlusion and readied for another advance towards the occlusion. At any point, the removal element 16 can be collapsed and retracted, as may be desirable to determine the composition of the occlusion material, or may be contracted or further expanded, such as discussed above, to define different cutting diameters. The steps of this method can be repeated as often as desired.

Still a further method takes advantage of a property provided by the removal element 16, viz. the removal element 16 can absorb forces applied to it and correspondingly deform or deflect. This method also takes advantage of the ability of the drive shaft 92 to axially expand or contract during operation. These property may be more readily understood with reference to FIGS. 11 and 16. FIG. 11 illustrates a cross section of a vascular lumen 166 occluded by occluding material 168. The occluding material 168 defines an eccentric surface 170 offset from the vascular lumen 166 by a distance which defines a non-occluded diameter in the vascular lumen 166. The removal element 16 is inserted into the non-occluded diameter and expanded, as discussed above, until an outer surface of the removal element 16 contacts the eccentric surface 170. Because the removal element 16 can absorb forces applied to it, such as those attendant with expansion or rotation of the removal element 16, the removal element 16 deflects or deforms such that the removal element 16 defines a configuration which complements the corresponding configuration of the eccentric surface 170. Thus, the removal element 16 can take into account varying occlusion morphology.

Once the removal element 16 has assumed the complementing configuration, as shown in FIG. 16, the motor 24 is activated and the removal element 16 begins to rotate within the non-occluded diameter. Deflection of the removal element 16 formed by the wires 102 causes longitudinal or axial and radial cutting actions or vectors to be reduced correspondingly. This may reduce the probability that healthy tissues might be removed because a cushioned, softer engagement may be formed between the healthy tissues and the removal element 16 due to the spring-like nature of the removal element 16. In addition, because the configuration of the removal element 16 conforms to the configuration of the occlusion material 168, upon rotation of the element 16, a greater concentration of removing forces can be generated at an area, indicated generally by reference numeral 172, on the occlusion material 168 than the force concentration present at an area 174 on the vascular lumen 166. Specifically, cutting forces may be evenly distributed over the area 174. This can lead to more efficient removal of vascular occlusion material 168.

Furthermore, it is to be noted that the spring-like nature of the removal element 16 provides for another method for removing vascular occlusion material. Specifically, according to this method, the removal element 16 may be placed within a lumen constricted or reduced by an occlusion such that the wires 102 are in proper position with respect to the occlusion for removal of occlusion material 168. At this point, the wire lock mechanism 50 and the removal element expansion control mechanism 52 for the removal devices 10 and 142, or the expansion control mechanism 184 for the removal devices 176 and 218 can be actuated, as described hereinabove, in order to expand the removal element 16 to define a diameter equal to a non-occluded diameter of the same vascular lumen, i.e. the diameter of the vascular lumen with the occlusion material removed.

The removal element 16 expands to define a configuration which corresponds to the configuration of the eccentric surface 170, as shown in FIG. 11 and as similarly depicted in FIG. 16. However, because the occlusion material 168 prevents the removal element 16 from immediately expanding to define the non-occluded diameter, the wires 102 of the element 16 absorb and store expanding forces in the form of spring energy. This stored spring energy allows the removal element 16 to be essentially self-expanding during operation of the removal device 10, 142, 176 or 218.

Specifically, the motor 24 is energized and the removal element 16 begins to rotate within the lumen 166, thereby removing vascular occlusion material 168 from the occlusion. As progressively more and more occlusion material 168 is removed from the occlusion, the spring energy stored within the wires 102 of the element 16 is released which causes the removal element 16 to expand further responsive to the amount of occlusion material 168 removed. Stored spring energy may also be released if the drive shaft 92 axially expands or contracts during operation. The stored spring energy is progressively released as greater amounts of occlusion material 168 are removed until the braided removal element 16 is expanded to the degree indicated by the removal element expansion control mechanism 52 or the expansion control mechanism 184. The removal element expansion limiting means also insures that the removal element 16 is not over-expanded. The removal element 16 ceases to expand once sufficient occlusion material 168 has been removed and once sufficient stored spring energy has been released. At this point, the diameter defined by the expanded removal element 16 should be approximately equal to the original, non-occluded diameter of the vascular lumen 166.

The self-expanding nature of the removal element 16 provides another method of removing vascular occlusion material from a vascular lumen. According to this method, the removal element 16 is pre-formed or expanded such that the element 16 defines a certain, pre-determined configuration. By placing the removal element 16 in this configuration, the element 16 is provided with a memory of this shape. Forming the element 16 with shape memory alloys, such as nitinol and the like, also insures effective shape or configuration memory. The pre-formed configuration preferably has dimensions suitable for intravascular insertion and navigation. The pre-formed removal element 16 is positioned adjacent the occlusion material, which defines a non-occluded diameter within the vascular lumen. The removal element 16 is then inserted into the non-occluded lumen.

Contact of the removal element 16 with the occlusion material imparts forces to the braided wires 102 which deform the configuration of the removal element 16. The spring-like nature of the braided wires 102 comprising the removal element 16 allows the element 16 to deform or otherwise comply to a configuration defined by the occlusion material, as illustrated in FIGS. 11 and 16. The element 16 can now be energized so that occlusion material can be removed. As progressively more occlusion material is removed, the shape memory of the wires 102 allows the element 16 to move towards the initial, pre-determined configuration. Once sufficient occlusion material has been removed, the memory aspects of the removal element 16 allow it to recover from its deformed state to its original configuration.

As is evident from the foregoing discussion, the embodiments of the present invention provide treating physicians with a number of methods for performing intravascular treatments. The individual steps comprising these methods can be performed in any order, and steps of one method can be combined with steps of other methods to achieve desired results. By providing an expandable material removal element 16, the embodiments of the invention provide a plurality of material removal element 16 sizes, shapes and cutting profiles or characteristics combined in a single intravascular occlusion material removal device 10, 142, 176 or 218. These shapes, sizes and characteristics are positively variable by the controlled incremental expansion of the material removal element 16 offered by the guidewire lock mechanism 50 and the material removal element expansion control mechanism 52 or the expansion control mechanism 184. Also, the various constructions of the material removal element radial expansion limiting means prevents over-expansion of the material removal element 16. It is to be noted that more efficient removal of vascular occlusion material may be possible if the motor 24 is energized prior to moving the removal element 16 towards the expanded position because the removal element 16 will gain momentum prior to engagement with the occlusion material.

By combining the material removal element 16 with the cutting surface 108, a plurality of differently directed cutting actions can be performed by the removal devices 10, 142, 176 and 218. Specifically, the material removal element 16 is capable of producing cutting actions directed radially and tangentially with respect to the vascular lumen or occlusion. In addition, the cutting surface 108 can produce cutting actions directed tangentially and longitudinally with respect to the vascular lumen or occlusion. Thus, at least three differently directed cutting actions can be produced by the removal devices 10, 142, 176 and 218. In addition, the occlusion material can be cut, ground, displaced, captured or aspirated. Specifically, relatively soft occlusion material can be sliced or cut by the wires 102 and fall into the hollow interior of the removal element 16, while relatively hard occlusion material can be ground by the abrasive 105 on the wires 102. Occlusion material can be retained within the collection chamber 228 by the coating 226. Thus, a treating physician can have greater flexibility in performing intravascular treatments while using only one device 10, 142, 176 or 218.

Figure 18:
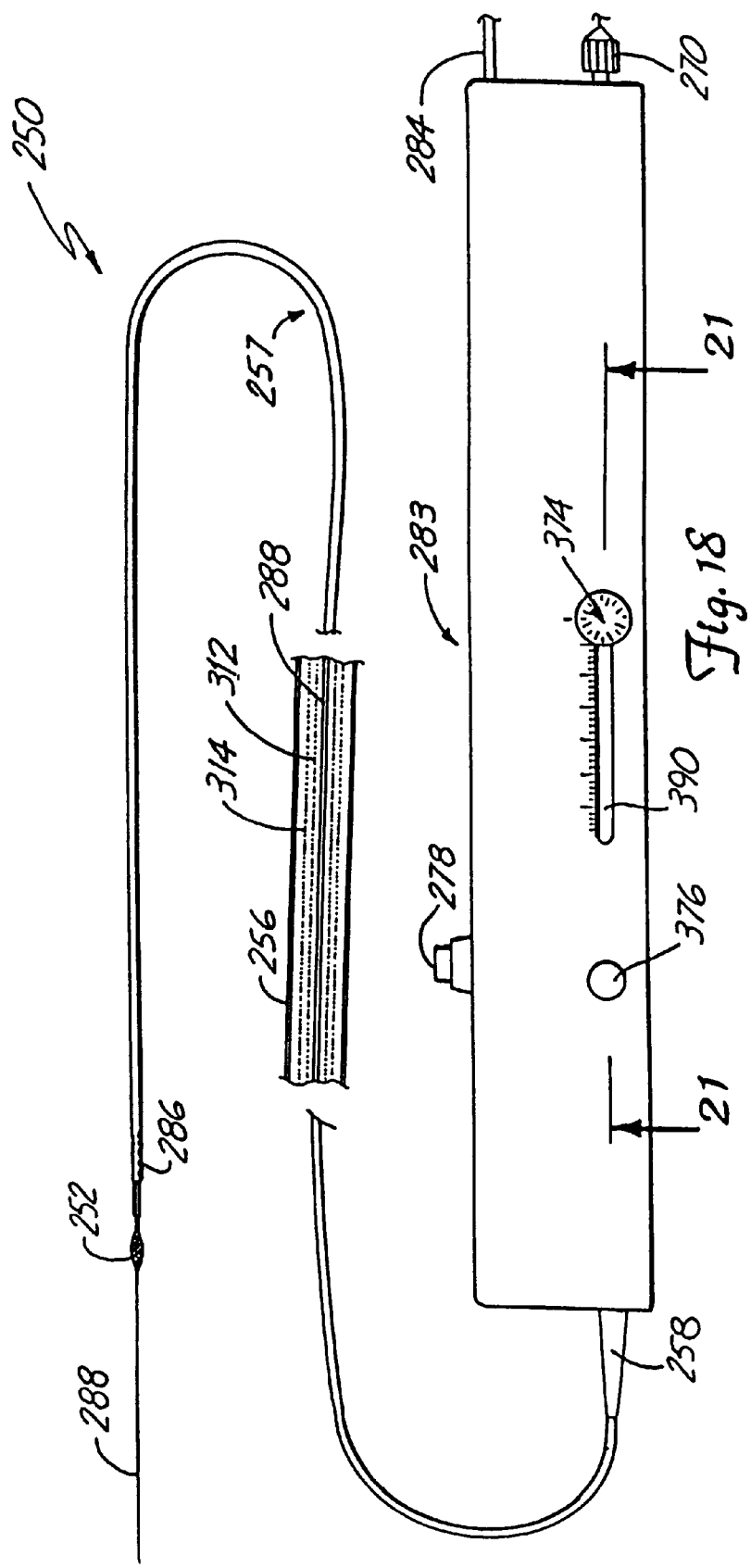
FIG. 18 is a side view of another embodiment of an expandable vascular occlusion material removal device.

FIG. 18 is a side view of another embodiment of an expandable vascular occlusion material removal device. The removal device 250 generally comprises a drive assembly 283, a drive shaft assembly 257, and an expandable removal element 252 located at a distal end of the drive shaft assembly 257. A proximal end of the drive shaft assembly 257 is connected to a strain relief 258 which forms a connection between the drive assembly 283 and the drive shaft assembly 257.

The drive shaft assembly 257 comprises two rotatable coaxial drive shafts including an inner drive shaft 312 and an outer drive shaft 314 wherein the inner drive shaft 312 and outer drive shaft 314 may be longitudinally slidable relative to one another and conjointly rotatable. In addition, the inner drive shaft 312 and the outer drive shaft 314 may move longitudinally together either proximally or distally. An outer sheath 256 receives the inner drive shaft 312 and the outer drive shaft 314 to prevent the vascular lumen of a patient from coming in direct contact with a substantial portion of outer drive shaft 314. The inner drive shaft 312 and outer drive shaft 314 may be longitudinally slidable and rotatable with respect to the outer sheath 256.

The distal end of the outer drive shaft 314 is operatively coupled to the proximal end of removal element 252. The distal end of inner drive shaft 312 passes through the removal element 252 and is coupled to the distal end of removal element 252. By sliding longitudinally the inner drive shaft 312 and the outer drive shaft 314 relative to one another, the expandable removal element 252 may move between a contracted position and an expanded position to engage occlusion material within a vascular lumen. In addition, by moving the inner drive shaft 312 and the outer drive shaft 314 conjointly in a proximal or distal direction, the removal element 252 may be moved proximally or distally within the vascular lumen.

Figure 19:
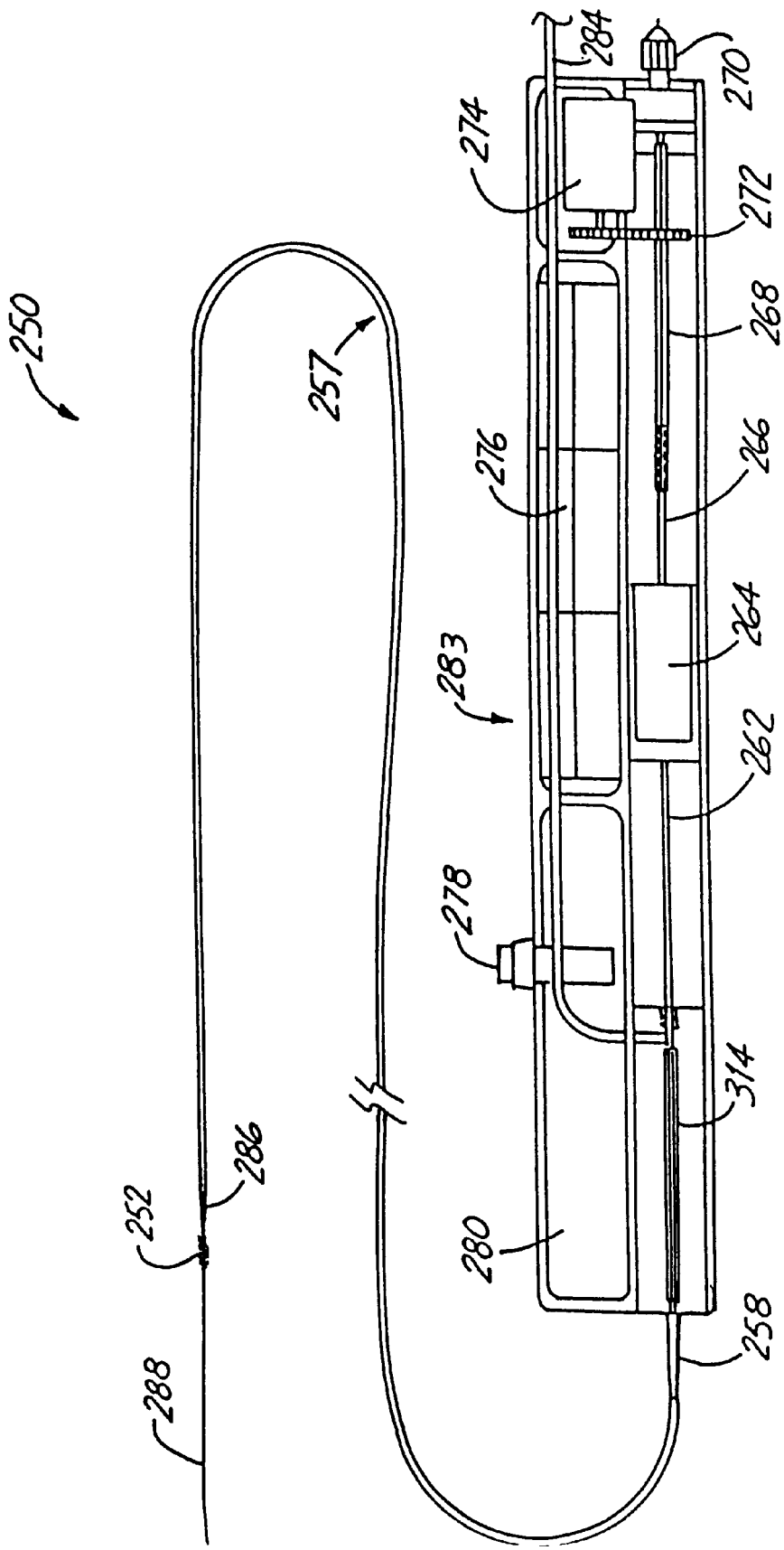
FIG. 19 is a partial sectioned side elevation view of another embodiment of an expandable vascular occlusion material removal device 250.

Now referring to FIGS. 18–19, the drive assembly 283 provides a mechanism for powering and controlling removal device 250 by providing the following apparatus: (1) a motor 274, turned on and off by power switch 278, for conjointly rotating inner drive shaft 312 and outer drive shaft 314; (2) an actuation control knob 374 for controlling the relative longitudinally shift between the inner drive shaft 312 and the outer drive shaft 314 thereby causing the expandable removal element 252 to move between a contracted position and an expanded position to engage occlusion material within the vascular lumen; (3) an elongated slot 390 for allowing actuation control knob 374 to be slid proximally or distally within elongated slot 390 for controlling gross longitudinal conjoint movement of the inner drive shaft 312 and the outer drive shaft 314 thereby causing the expandable removal element 252 to move longitudinally therewith within the vascular lumen; (4) a slide lock 376 for locking the longitudinal position of actuation control knob 374 within elongated slot 390; (5) a guide wire lock 270 for locking the longitudinal position of guidewire 288 relative to drive assembly 283; and (6) a solution flush line 284 for providing irrigation to the drive shaft assembly 257 and removal element 252 or for providing infusion of fluids, such as contrast media, a saline solution, a drug therapy, or the like, into the patient.

An exemplary use of the embodiments in FIGS. 18–19 comprises the following steps: (1) navigating a guide catheter (not shown) substantially into the vascular system of a patient; (2) sliding a guidewire 288 into the central cavity of the guide catheter until the guidewire 288 reaches the distal end of the guide catheter; (3) navigating the guidewire 288 from the distal end of the guide catheter further into the vascular system of a patient such that the guidewire 288 passes distally of the occlusion material to be removed; (4) advancing the removal element 252, drive shaft assembly 257, drive assembly 283, and guide wire lock 270 over the guidewire until the removal element 252 is adjacent to the occlusion material; (5) locking the guidewire into position using guidewire lock 270; (6) loosening slide lock 376 and sliding actuation control knob 374 proximally causing both the inner drive shaft 312 and the outer drive shaft 314, and therefore the removal element 252, to move conjointly in the distal direction thus engaging occlusion material; (7) engaging the control switch 278, thereby energizing motor 274 within drive assembly 283 and thus inducing rotation of the inner drive shaft 312 and outer drive shaft 314 which in turn rotates the material removal element 252 enabling the sharp edges or abrasive particles on the surfaces of removal element 252 to cut, abrade, ablate, or otherwise remove vascular occlusion material from a vascular lumen surface or a vascular occlusion; (8) turning the actuation control knob 374 to move the inner drive shaft 312 and outer drive shaft 314 relative to one another thus causing the removal element 252 to expand and engage the occlusion material; (9) advancing removal element 252 into the occlusion material at a given expanded position until the distal end of the occlusion material is reached; (10) returning removal element 252 proximally until the distal end of removal element 252 is proximal of the occlusion material; (11) rotating the actuation control knob 374 to increase the expansion of removal element 252, and proceeding to advance the removal element 252 through the occlusion material again. This process is continued until a predetermined amount of the occlusion material is removed. This description for using the present invention is only exemplary. Additional methods for using the present invention are contained herein.

FIG. 19 is a partial sectioned side elevation view of another embodiment of an expandable vascular occlusion material removal device 250. The detailed construction of the drive assembly 283 and the removal element 252 are more clearly shown in FIG. 20 and will be discussed in detail later. However, a general description of the major subcomponents of drive assembly 283 will be presented with respect to the embodiment shown in FIG. 19.

Drive assembly 283 may comprise motor 274 for rotating inner drive shaft 312 and outer drive shaft 314. As discussed in the text associated with FIG. 18, inner drive shaft 312 and outer drive shaft 314 are operatively coupled to the removal element 252. Therefore, motor 274 may provide the rotational force applied to removal element 252 for removing occlusion material.

Drive assembly 283 may also comprise a power source 276, illustrated as a plurality of batteries electrically connected in series, for energizing motor 274, and a control switch 278 connected electrically between the motor 274 and the power source 276 such that actuation of the control switch 278 allows current to flow between the power source 276 and the motor 274, thereby causing motor 274 to rotate. The motor 274 is attached to a set of gears 272 which transfers the torque provided by motor 274 to outer spline 268. Gears 272 may be in a one-to-one gear ratio but other gear ratios may be used to increase the power or speed of the device. Gears 272 are preferably spur gears model number 31800 available from Seitz Acetal Inc. but it is recognized that a suitable substitute may be available. In the exemplary embodiment of the invention, the motor 274 is a direct current micro-motor available from Micro Mo Electronics, Inc. of St. Petersburg, Fla., model number 2233T-04.5S, and the power source 276 comprises six (6) 1.5 Volt AA Alkaline batteries available from Duracell Corporation. It is recognized that there may be suitable substitutes for the above referenced elements and that the suitable substitutes may achieve similar results.

The motor 274 can rotate an outer spline 268, and therefore inner drive shaft 312 and outer drive shaft 314, at a speed of about 10,000 revolutions per minute, but it is envisioned that greater speeds, on the order of 100,000 revolutions per minute may be possible with different motor 274. For example, motor 274 may be similar to the brushless direct current motor available from Transicoil Inc. of Valley Forge, Pa., model number U-222285, which can reach speeds of 100,000 revolutions per minute. Thus, the removal device 250 could operate at speeds substantially within the range of 0 to 100,000 revolutions per minute. It is contemplated that outer spline 268 could be coupled directly to the drive shaft of motor 274 in a through-shaft configuration to achieve similar results.

The torque from motor 274 is transferred to outer spline 268 via gears 272. Outer spline 268 may be made from 3/32 square tubing that is 4.25 inches long made from stainless steel, injection molded plastic, injection molded ultra high density molecular weight polyetholene (UHMN-PE), or the like. An inner spline 266 is telescopically connected to outer spline 268. That is, the proximal end of inner spline 266 is received by the central cavity of the distal end of outer spline 268. Inner spline 266 is also made from square tubing so that when inner spline 266 is received by outer spline 268, torque is transferred from outer spline 268 to inner spline 266. Inner spline 266 can slide in and out of outer spline 268 even while torque is applied by motor 274. It is contemplated that spline 268 could be telescopically received by the central cavity of spline 266 and achieve the objectives of the present invention. It is also contemplated that inner spline 266 and outer spline 268 may have any cross sectional shape which allows a telescopic connection and the transfer of torque.

Inner spline 266 is operatively coupled to a proximal end of actuation mechanism 264. Actuation mechanism 264 provides for the following two primary functions; (1) controlling gross longitudinal conjoint movement of inner drive shaft 312 and outer drive shaft 314 thereby causing the expandable removal element 252 to move longitudinally therewith; and (2) controlling the relative shift between inner drive shaft 312 and an outer drive shaft 314 thereby causing the expandable removal element 252 to move between a contracted position and an expanded position to engage occlusion material within the vascular lumen. Because of the telescopic interface between inner spline 266 and outer spline 268, actuation mechanism 264 can move proximally or distally within drive assembly 283 to provide conjoint movement of an inner drive shaft 312 and outer drive shaft 314. The details of actuation mechanism 264 will be discussed further in conjunction with FIGS. 20–21.

Two coaxial hypotubes extend from the distal end of actuation mechanism 264 including an inner hypotube 318 (see FIG. 20) and an outer hypotube 262. Inner hypotube 318 and outer hypotube 262 are preferably made from stainless tubing coated with PTFE, injection molded plastic, injection molded ultra high density molecular weight polyetholene (UHMN-PE), or the like. However, it is recognized that other materials will work as well. The distal end of inner hypotube 318 is coupled to the proximal end of an inner drive shaft 312. The distal end of outer hypotube 262 is coupled to the proximal end of an outer drive shaft 314. A detailed description of the inner drive shaft 312 and the outer drive shaft 314 is contained in the text related to FIGS. 25–26. The inner drive shaft 312 and outer drive shaft 314 exit the distal end of drive assembly 283, pass through strain relief 258 and are received by outer sheath 256. Outer drive shaft 314 is coupled to the proximal end of expandable removal element 252. Inner drive shaft 312 passes through expandable removal element 252 and is coupled to the distal end of the expandable removal element 252. In this configuration, when inner drive shaft 312 and outer drive shaft 314 are moved longitudinally relative to one another by rotating actuation control knob 374 (see FIG. 18), the expandable removal element 252 moves between a contracted position and an expanded position thereby allowing expandable removal element 252 to engage or disengage intravascular occlusion material.

To insure that actuation mechanism 264 is able to move proximally and distally and therefore allowing the inner drive shaft 312 and outer drive shaft 314 and removal element 252 to move proximally and distally therewith, outer sheath 256 does not extend completely to the proximal end of expandable removal element 252. However, a sheath 286 may extend over the resulting exposed portion of the outer drive shaft 314 and substantially under outer sheath 256 for a distance substantially the same as, but greater than, that which actuation mechanism 264 can move proximally and distally within drive assembly 283. Sheath 286 is used to ensure that a vascular lumen is not in direct contact with the outer drive shaft 314. Sheath 286 may be made from, or coated with, PTFE or other lubricous material.

Drive housing 283 also contains a motor circuit cavity 280 and battery power supply 276. The motor control circuitry contained in motor circuit cavity 280 may provide several functions including a torque limiting function. When the physician is performing the atherectomy procedure, the interaction of expandable removal element 252 with the intravascular occlusion material will necessarily require motor 274 to provide various torque levels. If the physician has expanded removal element 252 too far or the physician is attempting to remove the intravascular occlusion material to fast, the torque provided by motor 274 will increase substantially. The torque limiting function of the electric motor control circuitry limits the level of torque that motor 274 can provide to a predetermined level. In one exemplary embodiment, the torque limit may be set to a level equivalent to approximately one half of the torque that the inner drive shaft 312 and the outer drive shaft 314 can sustain. In another exemplary embodiment, the torque limit may be set to the maximum level that can be sustained without causing damage to the patient's vascular system. It is contemplated that any predetermined limit may be is implemented in the torque limiting function.

An additional feature of the electric motor control circuitry is that prior to limiting the torque of motor 274, a warning signal, for example a tone or a light, is provided indicating to the physician that the maximum torque level is being approached. This feature enables the physician to back off before the electric motor control circuitry limits the torque provided by motor 274. Finally, the electric motor control circuitry may provide a torque meter comprising a plurality of LED elements. As the required torque increases, the number of LED elements that are turned on by the electric motor control circuitry is similarly increased. This provides the physician with an analog view of the torque developed during the atherectomy procedure.

The electric motor control circuitry may also provide for voltage regulation to insure that the torque and speed of motor 274 is not dependent on the battery resistance. In the exemplary embodiment, battery power supply 276 comprises six (6) 1.5 volt AA Duracell Alkaline batteries or the like connected in a series configuration. This results in approximately nine volts being supplied to the electric motor control circuitry. The voltage regulation feature regulates the nine volts provided by the battery power supply 276 to approximately six volts which is then ultimately supplied to motor 274. The voltage regulator feature of the motor control circuitry ensures that motor 274 operates at the same speed and provides the same torque despite having a slightly discharged battery power supply 276. In another embodiment, the voltage regulation level may be manually changed by the operator to increase the speed or power of the removal device 250.

The present invention may be advanced over a guidewire 288. The guidewire 288 may be received by removal element 252, inner drive shaft 312, inner hypotube 318, actuation mechanism 264, inner spline 266, outer spline 268, and guidewire lock 270. Thus, removal device 250 is of an over-the-wire construction which can facilitate removing the removal device 250 from, and replacing the removal device 250 in the patient because guidewire 288 can remain within the patient. Guidewire 288 may also provide support for removal element 252 within the vascular lumen of a patient. In an exemplary embodiment, guidewire 288 may be made slightly stiffer than removal element 252 such that guidewire 288 may help control the shape and position of removal element 252 within the vascular lumen, especially around corners. In addition, guidewire 288 can be slid distally of removal element 252 for facilitating intravascular navigation of removal element 252.

In an exemplary embodiment of the intravascular removal device 250, the guidewire 288 has an outer diameter measuring substantially within the range of 0.010" to 0.014". In addition, guidewire 288 is manufactured to be slightly stiffer than the expandable removal element 252 and drive shaft assembly 257 to ensure that guidewire 288 has the ability to control and direct the position of the expandable removal element assembly within the vascular lumen. Also, the guidewire 288 may be coated with a low friction coating, such as a nickel-silver alloy like nikasil, or a fluoropolymer infused nickel substance like nedox, or a nickel plating with PTFE spheres, for reducing friction between the guidewire 288 and the inner drive shaft 312. Finally, it is contemplated that guidewire 288 may have a 1 cm to 3 cm coiled tip at the distal end to be more easily navigated through the vascular structure. The distal tip of guidewire 288 may be made large enough such that removal element 252 cannot be pushed distally thereof to prevent removal element 252 from disengaging guidewire 288.

Guidewire lock 270 enables the physician to lock the guidewire in position relative to drive assemble 283. The details of Guidewire lock 270 are discussed fully above in the text relating to FIG. 2.

Finally, drive assembly 283 may comprise solution flush line 284. In one embodiment of the present invention, solution flush line 284 supplies a saline solution under slight positive pressure to drive shaft assembly 257. To insure the saline solution is in fluid communication with the cavity between inner drive shaft 312 and outer drive shaft 314 and the cavity within the inner drive shaft 312, holes 500 and 502 are provided for in the distal end of outer hypotube 262 and inner hypotube 318, respectively. In this exemplary embodiment, the saline solution acts as a lubricant between the inner drive shaft 312 and the outer drive shaft 314 as well as between the outer drive shaft 314 and outer sheath 256 and finally between the inner drive shaft 312 and the guidewire 288. The saline solution also purges air from the drive shafts and provides irrigation to the removal element 252 to block blood and the like from entering drive shaft assembly 257. Finally, solution flush line 284 can be utilized for infusion of fluids, such as contrast media, a saline solution, a drug therapy, and the like, into the patient, and for aspiration of the intravascular treatment site. Distal seal 260 provides a seal around outer hypotube 262 such that the saline solution provided by solution flush line 284 cannot flow proximally through the cavity defined by outer hypotube 262 and an outer wall 317 (see FIG. 20).

Figure 20:
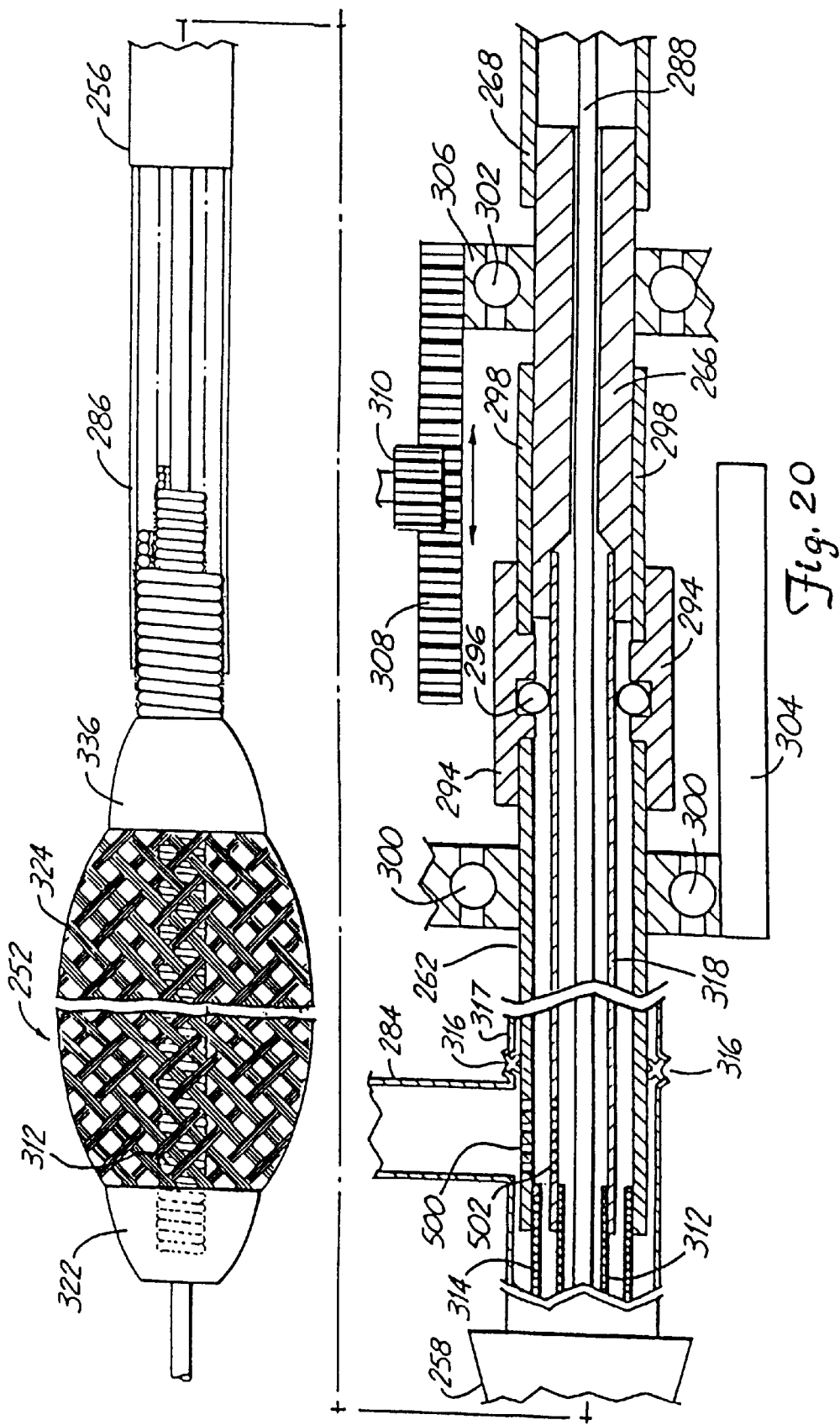
FIG. 20 is an enlarged sectional view of FIG. 19 showing the details of the drive assembly 283 of an exemplary embodiment of the present invention.

FIG. 20 is an enlarged sectional view of FIG. 19 showing the details of the drive assembly 283 of an exemplary embodiment of the present invention. The torque from motor 274 is provided to outer spline 268 via gears 272 (gears 272 and motor 274 are shown in FIG. 19). Outer spline 268 is telescopically coupled to inner spline 266 such that inner spline 266 can slide proximally and distally with respect to outer spline 268. Outer spline 268 and inner spline 266 are shaped such that torque can be applied from one to the other. An inner shaft bearing 302, preferably model number 7Y55-PSS 2507 available from Stock Drive Products, is pressed onto inner spline 266 such that if inner shaft bearing 302 is moved proximally or distally, inner spline 266 moved conjointly therewith. Inner shaft bearing 302 is coupled to an inner-actuator housing 306.

A rack gear 308, preferably made from nylon and available from Stock Drive Products as model number A-1M12-N48, is coupled to inner-actuator housing 306. A pinion gear 310, preferably made from nylon and available from Stock Drive Products as model number A-1M-2-N48012, engages rack gear 308 such that when pinion gear 310 is rotated, rack gear 308 moves relative to pinion gear 310 either proximally or distally depending on the direction of rotation. The movement of rack gear 308 is transmitted to inner spline 266 which moves conjointly with rack gear 308. Inner spline 266 is telescopically connected to outer actuation spline 298. Again, inner spline 266 and outer actuation spline 298 are shaped such that torque can be transmitted from one to the other. Therefore, inner spline 266 may slide proximally or distally with respect to outer actuation spline 298 in a telescoping fashion when pinion gear 310 is rotated. Inner spline 266 is operatively connected to the proximal end of inner hypotube 318. The distal end of inner hypotube 318 is coupled to inner drive shaft 312. Therefore, torque applied to inner spline 266 by motor 274 can be transmitted to inner drive shaft 312.

As previously stated, inner spline 266 and outer actuation spline 298 are shaped such that torque can be transferred from one to the other. Therefore, outer actuation spline 298 may rotate conjointly with inner spline 266. Outer actuation spline 298 is operatively coupled to reciprocating seal housing 294. Reciprocating seal housing 294 comprises reciprocating seal 296 for preventing saline solution from traversing proximally of reciprocating seal housing 294 through the cavity defined by outer hypotube 262 and inner hypotube 318. Reciprocating seal housing 294 is operatively connected to the proximal end of outer hypotube 262. The distal end of outer hypotube 262 is operatively connected to outer drive shaft 314. Therefore, torque applied to inner spline 266 by motor 274 can be transmitted to outer drive shaft 314. An outer shaft bearing 300, preferably part number 7Y55-PSS 2512 available from Stock Drive Products, is pressed onto outer hypotube 262 and further coupled to outer actuator housing 304. Outer shaft bearing 300 holds outer hypotube 262 in a stationary position with respect to actuation mechanism 264. Quad ring seal 316 is provided around outer hypotube 262 to prevent fluid from traversing proximally along the outer edge of outer hypotube 262.

Guidewire 288, inner drive shaft 312 and outer drive shaft 314 traverse coaxially through outer sheath 256 to expandable removal element 252. Outer drive shaft 314 is operatively coupled to the proximal tip 336 of expandable removal element 252 and provides torque thereto. Inner drive shaft 312 traverses through expandable removal element 252 and is operatively coupled to the distal tip 322 of expandable removal element 252 and provides torque thereto. In one embodiment of the present invention, outer sheath 256 does not extend all the way to the proximal tip 336 of expandable removal element 252 thus exposing a portion of outer drive shaft 314 to the vascular lumen of the patient. Outer drive shaft 314 may be shielded from direct contact with the vascular lumen by a coating 286 placed over outer drive shaft 314 that extends proximally of the distal end of outer sheath 256 for a distance substantially similar to, but greater than, the distance actuation mechanism can move proximally and distally. The coating may be made from PTFE or the like.

As stated earlier, solution flush line 284 can be utilized for infusion of fluids, such as contrast media, a saline solution, a drug therapy, and the like, into the patient, and for aspiration of the intravascular treatment site. This infused fluid can also provide for increased lubrication to the drive shaft assembly 257, which may be beneficial during operation of the motor 274, and for allowing irrigation of an intravascular treatment site, which may be necessary to maintain a fluid balance within a vascular lumen if aspiration techniques are also used. Therefore, in one embodiment of the present invention, it is desirable to have saline solution flow into the inner cavity of inner drive shaft 312, between inner drive shaft 312 and outer drive shaft 314, and between outer drive shaft 314 and outer sheath 256.

To enable fluid to enter the outer drive shaft 314 and inner drive shaft 312, holes 500 are provided in the distal portion of outer hypotube 262 and holes 502 are provided in the distal portion of inner hypotube 318. Therefore, solution flush line 284 is in fluid communication with the inner cavity of inner drive shaft 312, the cavity between inner drive shaft 312 and outer drive shaft 314, and the cavity between outer drive shaft 314 and outer sheath 256. The preferred pressure of the saline solution results in approximately 10 cc of fluid being pumped into solution flush line 284 per minute. However, all of the fluid supplied to solution flush line 284 may not be delivered to removal element 252 because some of the fluid may escape past quad ring seal 316, reciprocating seal 296, and the inner portion of inner spline 266.

An advantage of providing positive pressure to the saline solution is that blood and other particulates are kept from entering the distal end of drive shaft assembly 257 and hence from causing friction therein.

It is undesirable to have saline solution or the like, provided by solution flush line 284, to travel proximally of reciprocating seal housing 294 and engage motor 274. Therefore, quad ring seal 316 prevents fluid from traveling proximally along the outer surface of outer hypotube 262. Reciprocating seal 296 prevents fluid from traveling proximally between inner hypotube 318 and outer hypotube 262. Finally, the inner portion of inner spline 266 is necked down to be in close tolerance with guidewire 288. The tolerance between guidewire 288 and the inner portion of inner spline 266 is such that a significant amount of fluid cannot pass proximally of that point. The combination of these three seals prevents most fluid provided by solution flush line 284 from flowing proximally to engage motor 274. A drain hole is supplied in drive housing 283 to allow any fluid that leaks past quad ring seal 316, reciprocating seal 296, and the inner portion of inner spline 266 to drain from drive housing 283 before reaching motor 274.

In some embodiments of the present invention, aspiration may be provided or enhanced by an impeller-like element operatively attached to the drive shafts such that rotation of the drive shafts and the impeller element generates a fluid flow within the vascular lumen, thereby causing particulates to flow into the space defined by outer sheath 256. In other embodiments, multiple impeller-like elements may be attached to the drive shafts at various locations along the longitudinal axis thereof.

Figure 21:
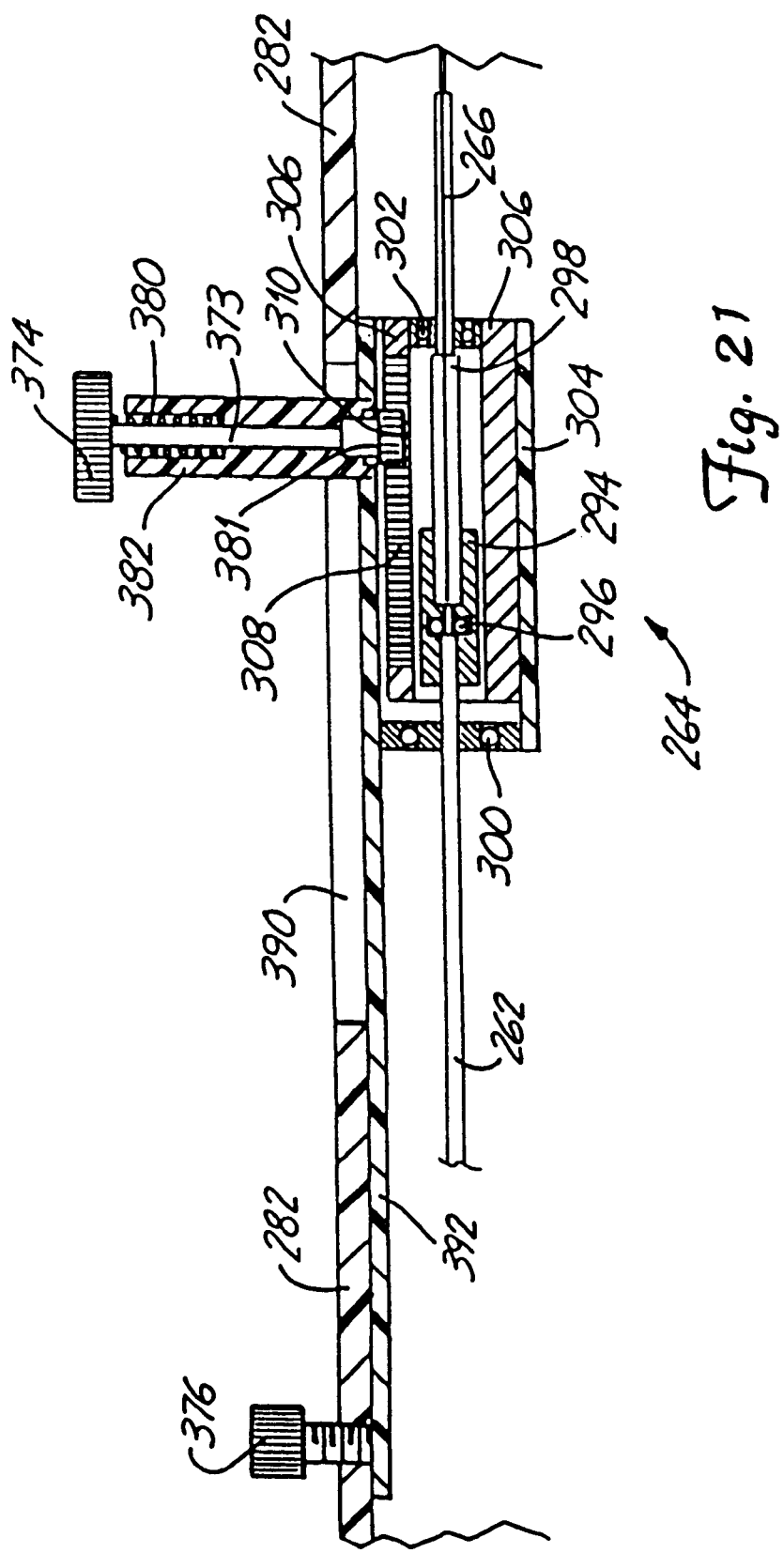
FIG. 21 is a sectional view along lines 21 of FIG. 18.

FIG. 21 is a sectional view along lines 21 of FIG. 18. The details of one view of actuation mechanism 264 have already been described in detail in FIG. 20. However, a further description of a sectional view is contained herein. Slide lock 376 passes through drive housing 282 and engages actuation sliding member 392. Actuation sliding member 392 is coupled to advance control housing 382 and outer shaft bearing 300. An outer shaft bearing 300 is pressed onto outer hypotube 262 such that outer hypotube 262 moves conjointly with outer shaft bearing 300. An inner shaft bearing 302 is pressed onto inner spline 266 such that inner spline 266 moves conjointly with inner shaft bearing 302. Inner spline 266 is telescopically coupled to outer actuation spline 298 such that inner spline 266 can move proximally and distally with respect to outer actuation spline 298. Inner shaft bearing 302 is pressed into inner actuation housing 306. Rack gear 308 is operatively coupled to inner actuator housing 306.

In addition, a spring 380 is placed in advancement control housing 382 such that spring 380 engages actuation control knob 374 forcing it in an upward direction. This, in turn, forces pinion gear 310 also in an upward direction. Advancement control housing 382 has a set of gear teeth 381 located near pinion gear 310 to engage pinion gear 310 when spring 380 forces pinion gear 310 upwardly. This, in effect, prevents pinion gear 310 from rotating while spring 380 forces pinion gear 310 in an upward direction. To allow pinion gear 310 to rotate and cause inner spline 266 to move with respect to outer actuation spline 298, the physician must depress actuation control knob 374 such that pinion gear 310 does not engage teeth 381 provided on the advancement control housing 382 and only engages rack gear 308.

In the exemplary embodiment, outer actuation spline 298, reciprocating seal housing 294, outer shaft bear 300, outer hypotube 262, and outer drive shaft 314 are held stationary with respect to actuation sliding member 392 and advancement control housing 382. Therefore, by depressing actuation control knob 374 and rotating it in either direction, pinion gear 310 engages rack gear 308 and moves rack gear 308, inner actuator housing 306, inner shaft bearing 302, inner spline 266, and finally inner drive shaft 312 with respect to outer drive shaft 314 thereby causing the removal element 252 to expand or contract depending on the direction of rotation of actuation control knob 374. In the exemplary embodiment, to slide removal element 252 to the expanded position, the actuation control knob is rotated clockwise thereby moving the inner drive shaft 312 proximately with respect to the outer drive shaft 314.

The degree of expansion of removal element 252 is directly proportional to the amount of relative sliding between the inner drive shaft 312 and the outer drive shaft 314. Thus, the degree of expansion and/or contraction of removal element 352 can be measured by suitable scaling means disposed on the drive housing 282 or on the actuation control knob 374 as shown. When a desired degree of expansion of removal element 252 has been achieved, the actuation control knob 374 can then be released. The spring 380 then expands and forces a portion of the teeth of pinion gear 310 into engagement with teeth 381 located on the inner portion of advancement control housing 382, while a portion of the teeth on pinion gear 310 remain engaged with the teeth located on rack gear 308. Interengagement of the teeth on pinion gear 310 with teeth 381 on the inner portion of advancement control housing 382 positively locks the relative axial position of inner drive shaft 312 and outer drive shaft 314 and hence the expanded position of the material removal element 352. Therefore, the actuation mechanism 264 allows for a positively controlled analog expansion of the removal element 252 by rotating the actuation control knob 274. It is contemplated that the present embodiment of the present invention employs a radial expansion limiting means as described in FIG. 7 and FIG. 8.

An embodiment of the present invention allows actuation mechanism 264 to move proximally and distally within elongated slot 390. This allows the physician to move both inner drive shaft 312 and outer drive shaft 314 conjointly in a proximal or distal direction. The degree of distal or proximal movement of the removal element 352 can be measured by suitable scaling means disposed on the drive housing 282 as shown. The physician may lock the position of the inner drive shaft 312 and outer drive shaft 314 by turning slide lock 376 such that it engages actuation sliding member 392 (see FIG. 21).

Figure 22:
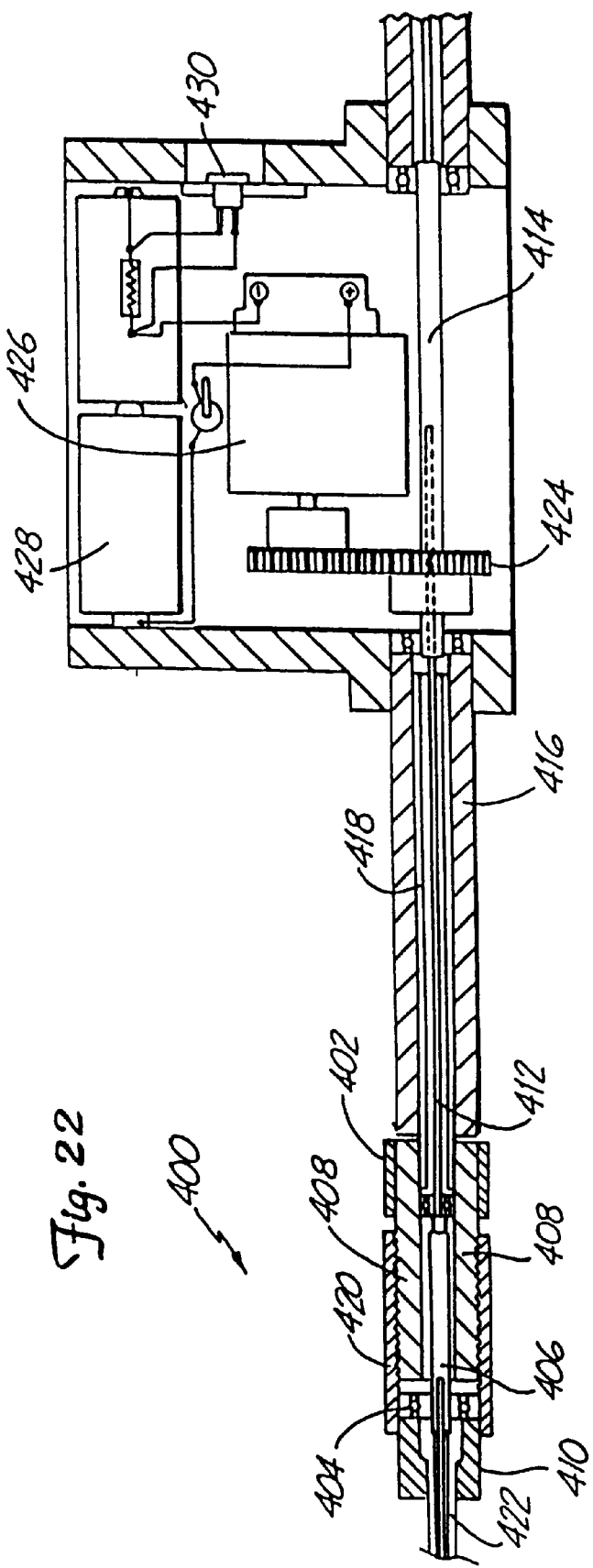
FIG. 22 is a sectional view of another embodiment of a vascular occlusion material removal device.

FIG. 22 is a sectional view of another embodiment of a vascular occlusion material removal device. This embodiment operates similar to the embodiment described in FIG. 18, however, the actuation mechanism 400 is somewhat different. In this embodiment, actuation mechanism 400 is controlled by turning actuation control sleeve 420 rather than activation control knob 374 as in FIG. 21. Activation control sleeve 420 engages outer activator spline 406 via screw-like threads. By turning actuation control sleeve 420, outer shaft bearing 404, outer activator housing 410, and outer activator spline 406 all move relative to inner activator housing 408 and outer sheath 256. Therefore, in this exemplary embodiment, the physician turns activation control sleeve 420 to move outer drive shaft 314 distally with respect to inner drive shaft 312.

To longitudinally move inner drive shaft 312 and outer drive shaft 314 conjointly, the physician places his hand on activation mechanism 400 or directly on the proximal end of outer sheath 422 and slides it in either a proximal or distal direction. FIG. 22 shows activation mechanism 400 moved to its furthest proximal position. As the physician moves actuation mechanism 400 distally, inner spline 412 telescopes out from outer spline 414. As in the embodiment shown in FIG. 18, inner spline 412 is telescopically coupled to outer spline 414. FIG. 22 shows inner spline 412 as being received by outer spline 414, however, it is contemplated that inner spline 412 could receive outer spline 414 and achieve similar results. This embodiment also comprises a battery power supply 428, a power switch 430, an electric DC motor 426, and gears 424.

Figure 23:
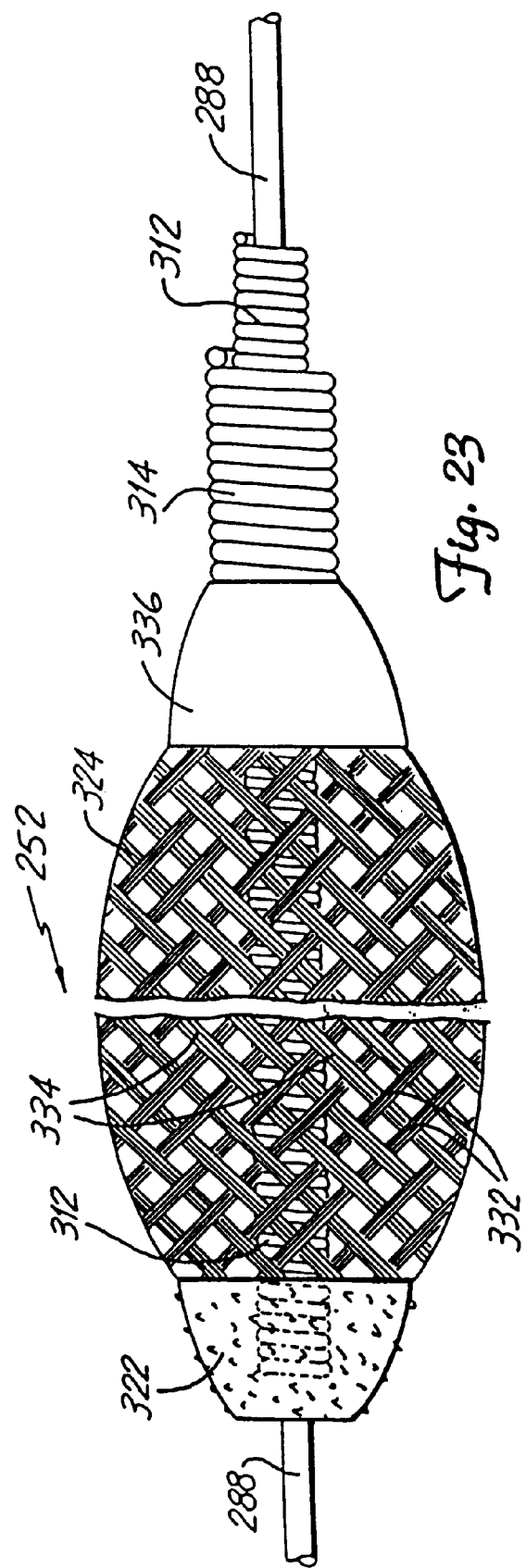
FIG. 23 is an enlarged side elevational view of an exemplary embodiment of expandable removal element 252.

FIG. 23 is an enlarged side elevational view of an exemplary embodiment of expandable removal element 252. Outer drive shaft 314 is operatively coupled to proximal tip 336 of expandable removal element 252. Inner drive shaft 312 extends through expandable removal element 252 and is operatively coupled to distal tip 322. Guidewire 288 extends through the center of inner drive shaft 312 and extends distally of expandable removal element 252. The cutting element of expandable removal element 252 comprises a plurality of braided strands 324. Each strand within the braid comprises at least one wire.

Figure 24:
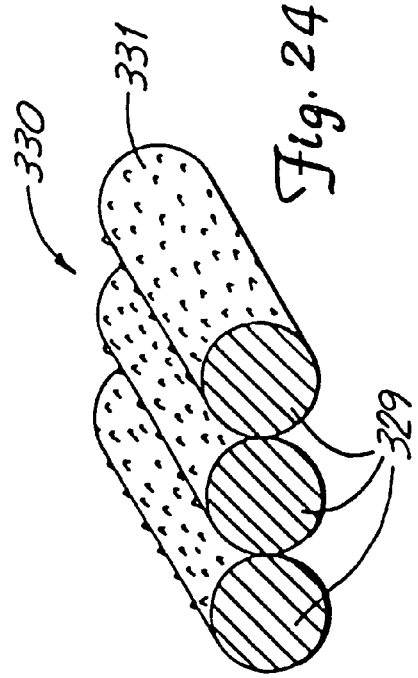
FIG. 24 shows a cross-section of one strand within the braid of expandable removal element 252 containing three wires per strand.

FIG. 24 shows a cross-section of one strand within the braid of expandable removal element 252 containing three wires per strand. More or less than three wires may be included in each strand. By increasing the number of wires per strand, the surface area available for cutting increases. In addition, the "window" size between wires decreases, thus reducing the likelihood that large sections of the occlusion material will be broken away from the vascular lumen. Adding multiple wires per strand, however, decreases the flexibility of the removal element.

One embodiment of the present invention uses a two over/two under braid pattern. Strand 324 passes over two strands at 334 and subsequently passes under two strands at 332. This is known as a two over/two under braid pattern. Another embodiment of the present invention includes a one over/one under braid pattern (not shown). The braid pattern used in a particular embodiment of expandable removal element 252, along with a number of wires per braid, define the cutting performance and flexibility of the expandable removal element 252.

The material removal element 252 of the exemplary embodiment generally comprises a plurality, preferably about 8 to 48, of strands 324. Each wire within strand 324 preferably has a substantially round latitudinal cross section having an outer diameter of about 0.001" to 0.005", although wires having flat, square, or triangular cross sections can also be used. As stated in the previous paragraph, the wires 329 within each braid comprise nitinol super-elastic wire, chromium-doped, having a diameter of about 0.002". In this embodiment, up to 48 strands are braided at about 20 to 120 pics per inch and heat set at approximately 350 degrees Celsius for about 30 minutes. In addition, the removal element 252 has a length substantially within the range of about 0.5 cm to 3 cm, a contracted diameter substantially within the range of 1 mm to 1.5 mm, and a maximum expanded diameter in the range of 2 mm to 4 mm.

The wires 329 within each strand may be made from any suitable material. However, it is recommended that the wires 329 be made from a super-elastic or shape memory metal alloy, such as nitinol and the like, which allows the wires to recover from strains greater than those recoverable by other metals. This increased strain recovery allows the wires 329 to resist permanent deformation during repeated expansions and contractions as well as during contact with vascular occlusion material. The use of super-elastic alloys for the wires within the braids facilitates return of the material removal element 252 to its original low profile, contracted condition, which also makes intravascular navigation of the material removal element 252 easier.

The outer surfaces of the wires 329 in the strands 324 may be sharpened, etched or coated with an abrasive 331, such as a diamond grit and the like, to improve the removing or cutting characteristics of the removal element 252. In one embodiment, a diamond grit having a grit size substantially within the range of 3 to 100 microns is electroplated onto the wires 329 in substantially uniform manner, however, the grit may be asymmetrically deposited on the wires 329 if desired. In another exemplary embodiment, the abrasive 331 may comprise a diamond grit or synthetic abrasive, such as a cubic boron nitride and the like, having a grit size approximately within the range of 3 to 25 microns, attached to the wires 329 by a nickel electroplating process.

Before the abrasive coating 331 is applied via a conventional nickel electroplating process, a cleaning and pre-plating process may be used to prepare wires 329. This process involves three basic steps: (1) performing an anodic caustic cleaning to degrease wires 329 and to decrease hydrogen embrittlement of the wire material during the nickel electroplating process; (2) performing an anodic etch in sulfuric acid to remove oxide from the wire material and to decrease hydrogen embrittlement of the wire material during the nickel electroplating process; and (3) performing a low phosphorous electroless nickel bath wherein in the reverse current or anodic mode of this step, oxide may be removed from the wire material and in the direct current or cathodic mode of this step, a nickel plating substrate may be applied to wires 329. After these cleaning and pre-plating steps are completed, wires 329 may be plated with an abrasive coating as is conventional in the art. It may be desirable to shot peen wires 329 prior to the cleaning or pre-plating steps described herein above to clean wires 329 and to increase the fatigue strength of wires 329 by compressing their surface.

It is contemplated that at least one of the plurality of wires contained in each braid of expandable removal element 252 can be replaced with a wire made from a radiopaque material such as gold, platinum, or the like. This allows the physician to observe the location of expandable removal element 252 its expansion setting using X-ray or other means.

A distal tip 322 is attached to the distal end of the inner drive shaft 312 by suitable means, such as an adhesive, solder, braze, weld, tin solder mold, or mechanical swag, and the distal ends of the strands 324 are attached to the distal tip 322 by similar means. Similarly, a proximal tip 336 is attached to the distal end of the outer drive shaft 314 by suitable means, such as an adhesive, solder, braze, weld, or tin solder mold, and the proximal ends of the strands 324 are attached to the proximal tip 336 by similar means. Thus, the braided wires 329 comprising the material removal element 252 rotate conjointly with drive shafts 312 and 314 and are under the influence of forces generated by the motor 274. The distal tip 322 is provided with a cutting surface located distally of the point of attachment of the wires 329. The cutting surface may be coated with an abrasive, such as the diamond grit or synthetic abrasive as disclosed earlier.

FIG. 25 is an enlarged side elevational view of an exemplary embodiment of removal element 252. Outer drive shaft 314 is operatively coupled to a proximal tip 336 of removal element 252. Inner drive shaft 312 extends through removal element 252 and is operatively coupled to a distal tip 322. Guidewire 288 extends through the center of inner drive shaft 312 and extends distally of removal element 252. The cutting means of removal element 252 comprises a plurality of braided strands 351.

FIG. 26 shows an expanded view of an exemplary embodiment of one strand 351 within the braid pattern of removal element 252. The cutting means of removal element 252 comprise a plurality of braided strands 351 wherein each strand 351 is radially wrapped with a wrapping wire 342. Although only one primary braid wire 340 is shown per strand 351, it is recognized that a number of primary braid wires 340 may be included in each strand 351 of the braid. Also, primary braid wire 340 may be wrapped with a number of wrapping wires 342 before primary braid wires 340 are braided together to form removal element 252. One advantage of the exemplary embodiment is that primary braid wire 340 may be manufactured from a material with advantageous properties to enhance proper expansion and contraction of removal element 252 while wrapping wire 342 may be made from a material which readily accepts an abrasive coating 344. In addition, primary braid wire 340 may continually be expanded and contracted as removal element 252 is expanded and contracted and therefore primary braid wire 340 may experience significant surface strain. Wrapping wire 342, on the other hand, is in a coil configuration wrapped around primary braid wire 340 and therefore may not experience the same level of surface strain as primary braid wire 340. Therefore, abrasive coating 344 placed on wrapping wire 342 may then last longer than if applied directly to the braid wire 340.

Primary braid wires 340 may be made from any suitable material. However, it is recommended that primary braid wires 340 be made from a super-elastic or shape memory metal alloy, such as nitinol and the like, which allows the wires to recover from strains greater than those recoverable by other metals. This increased strain recovery allows primary braid wires 340 to resist permanent deformation during repeated expansions and contractions as well as during contact with vascular occlusion material. The use of super-elastic alloys for primary braid wires 340 within strands 351 facilitates return of removal element 252 to its original low profile, contracted condition, which also eases intravascular navigation of removal element 252. It is also recommended that wrapping wires 342 be made from stainless steel or some other material such as a radiopaque material that may be readily plated with abrasive 344.

Removal element 252 of this exemplary embodiment generally comprises a plurality, preferably about 8 to 48, of strands 351. Primary braid wires 340 within each strand 351 preferably have a substantially round latitudinal cross section defining an outer diameter of about 0.001" to 0.005", although wires having flat, square, or triangular cross sections can also be used. It is preferred that primary braid wires 340 within each braid comprise nitinol super-elastic wire, chromium-doped, having a diameter of about 0.003". Wrapping wires 342 preferably have a substantially round latitudinal cross section defining an outer diameter of about 0.001" to 0.005", although wires having flat, square, or triangular cross sections can also be used. Wrapping wires 342 preferably comprise stainless steel wire and are wound radially around primary braid wires 340 with a spacing between adjacent coils of 0.002" to 0.005" with 0.0025" preferred. In this embodiment, up to 48 strands 351 are braided together at about 20 to 120 pics per inch and heat set at approximately 350 degrees Celsius for about 30 minutes. The resulting braid preferably has an overall length substantially within the range of about 0.5 cm to 3 cm, a contracted diameter substantially within the range of 1 mm to 1.5 mm, and a maximum expanded diameter in the range of 2 mm to 4 mm. However, it is recognized that wrapping wire 342 may comprise Elgiloy alloy which is a cobalt, chromium, nickel alloy available from Elgiloy Limited Partnership. It is further recognized that wrapping wire 342 may comprise Kevlar thread or any other suitable material.

One exemplary embodiment of the present invention uses a two over/two under braid pattern. Another embodiment of the present invention uses a one over/one under braid pattern. The braid pattern used in a particular embodiment of removal element 252, along with the number of primary braid wires 340 per strand 351, define the cutting characteristics and flexibility of removal element 252. It is recognized that different braid patterns and different numbers of primary braid wires 340 per strand 351 may be used to obtain substantially similar results. Finally, it is recognized that each strand 351 within the braid pattern may be radially wrapped with a plurality of wrapping wires 342.

The outer surfaces of wrapping wires 342 may be sharpened, etched or coated with abrasive 344, such as a diamond grit and the like, to improve the removing or cutting characteristics of removal element 252. In one embodiment, a diamond grit having a grit size substantially within the range of 3 to 100 microns is electroplated onto wrapping wires 342 in a substantially uniform manner, however, the grit may be asymmetrically deposited on wrapping wires 342 if desired. Natural diamonds are preferred over hand made diamonds because natural diamonds have a more jagged surface and therefore may be bonded to more easily. Natural diamonds also provide for better abrasive characteristics. In another exemplary embodiment, abrasive 344 may comprise a synthetic abrasive, such as a cubic boron nitride and the like, having a grit size approximately within the range of 3 to 25 microns, attached to wrapping wires 342 by a nickel electroplating process known in the art.

To increase the flexibility of removal element 252, smaller abrasive particles and a thinner plating process may be used in plating removal element 252. Also, because primary braid wires 340 experiences higher levels of stress than wrapping wires 342, it is preferable to only plate wrapping wires 342 with abrasive 344 and not plate the primary braid wire 340. This can be accomplished using known plating techniques.

Finally, bridging of abrasive plating 344 between coils 346 and 348 of wrapping wire 342 is undesirable because cracking of the abrasive plating can occur in these areas. Therefore, wrapping wire 342 may be wrapped such that coils 346 and 348 are a sufficient distance apart to prevent bridging between them during the plating process. The preferred spacing between adjacent coils of wrapping wire 342 may be 0.001" to 0.005" with 0.0025" preferred.

Distal tip 322 is attached to the distal end of inner drive shaft 312 by suitable means, such as an adhesive, solder, braze, weld, tin solder mold, or mechanical swag, and the distal ends of primary braid wires 340 are attached to distal tip 322 by similar means. Similarly, proximal tip 336 is attached to the distal end of outer drive shaft 314 by suitable means, such as an adhesive, solder, braze, weld, or tin solder mold, and the proximal ends of primary braid wires 340 are attached to proximal tip 336 by similar means. Thus, primary braid wires 340 comprising removal element 252 rotate conjointly with drive shafts 312 and 314 and are under the influence of forces generated by motor 274. Distal tip 322 is provided with a cutting surface located distally of the point of attachment of primary braid wires 340. The cutting surface may be coated with an abrasive 319, such as the diamond grit or synthetic abrasive disclosed earlier.

Finally, it is recognized that at least one of the plurality of primary braid wires 340 and/or wrapping wires 342 may be replaced with a wire made from a radiopaque material such that a physician can view the position and the degree of expansion of removal element 252 using X-rays or similar means.

FIG. 27 is an enlarged partially-sectioned side elevational view of the dual drive shaft embodiment of the present invention. In the exemplary embodiment, both inner drive shaft 312 and outer drive shaft 314 comprise two oppositely wound helices. Inner drive shaft 312 comprises an inner helix 362 and an outer helix 360. The inner helix 362 of inner drive shaft 312 is formed by wires wound in a direction relative to the intended direction of rotation such that inner helix 362 may radially expand upon rotation of the inner drive shaft 312. Outer helix 360, formed by wires wound in the opposite direction of inner helix 362 and surrounds inner helix 362. Therefore, outer helix 360 is wound in a direction relative to the intended direction of rotation such that outer helix 360 may radially contract upon rotation of inner drive shaft 312. The radial expansion of the inner helix 362 is balanced by the radially contraction of outer helix 360. Inner helix 362 and outer helix 360 may contain the same number of windings per inch. Outer drive shaft 314 may be formed in a similar manner.

Each helix is wound at a given winding angle whereby the winding angle is the angle of the coils of the helix to the latitudinal axis of the helix. The winding angle of inner helix 362 and outer helix 360 depends primarily on the diameter of the wire used in the helix and on the major diameter of the respective helix. To increase the winding angle of a particular helix, a multi-filar coil configuration may be used. A multi-filar configuration is a coil having a plurality of substantially parallel wires simultaneously wound to form a helix thereby increasing the effective diameter of the wrapping wire while still maintaining a low profile helix. In the exemplary embodiment shown in FIG. 23, inner drive shaft 312 and outer drive shaft 314 each have three (3) wires wound simultaneously, i.e. a three filar configuration, to increase the winding angle of the coil. It is recognized that other numbers of wires may be used in the multi-filar configuration to achieve various winding angles.

Another advantage to having an increased winding angle in the helices is that the flexibility of the helix may increased and that it may be less likely that the coils will overlap each other when the helix is bent. This is particularly important in the present application because the helices are used in rotating drive shafts which must traverse a contorted vascular lumen. In addition, the increased winding angle may reduce the interference between inner drive shaft 312 and outer drive shaft 314 when inner drive shaft 312 and outer drive shaft 314 are slid longitudinally relative to one another.

The helices used in the inner drive shaft 312 and outer drive shaft 314 may be prestressed by providing an axial torque about the longitudinal axis of the wire used to form the helices while the wire is being wrapped around a winding mandrel. In an exemplary embodiment, the axial torque applied to the wire forming a helix may not exceed the linear elastic yield point of the wire. By prestressing the wires used to form the helices in this manner, the initial expansion of the helices may be reduced when a longitudinal force is applied thereto thereby giving the helices increased longitudinal strength. This may increase the responsiveness of inner drive shaft 312 and outer drive shaft 314 when longitudinal force is applied to them, like for example, when sliding inner drive shaft 312 and outer drive shaft 314 relative to one another to expand and contract removal element 252. It is also recognized that the wires used to form the inner helix 362 and outer helix 360 can prestressed using conventional shot pinging techniques.

Outer drive shaft 314 receives inner drive shaft 312 such that inner drive shaft 312 is slidable longitudinally with respect to outer drive shaft 314. Similarly to inner drive shaft 312, outer drive shaft 314 comprises two oppositely wound helices. Outer drive shaft 314 is constructed in a similar manner as inner drive shaft 312. The winding angle of the windings of outer drive shaft 314 may be less than that employed in inner drive shaft 312.

Another embodiment of inner drive shaft 312 and outer drive shaft 314 comprises only a single wound helix. In this embodiment, the inner and outer drive shafts may axially expand or contract responsive to radial contraction or expansion, respectively, thereof during operation of the removal device 352. However, to combat this problem, the dual drive shaft configuration is preferred and may be constructed, by appropriately winding the inner and outer coils, to render axial expansion and/or contraction of inner drive shaft 312 controllable. Both inner drive shaft 312 and outer drive shaft 314 are received by outer sheath 256 such that outer drive shaft 314 can rotatably and slidably move within outer sheath 256. Outer sheath 256 may comprise an inner sheath layer 292 and an outer sheath layer 290. Inner sheath layer 292 may be thinner than outer sheath layer 290 and may be made from a lubricous material. Outer sheath layer 290 may be made from a low density material to keep outer sheath 256 flexible and is relatively thick to reduce the likelihood of kinking. However, the thickness of the distal end of sheath 256 may be tapered down to provide a smooth transition to outer drive shaft 314 or PTFE coating 286. It is envisioned that the outer surface of outer sheath 256 may be coated with a hydrophilic coating or silicon coating to provide a lubricous surface for sliding within the vascular lumen. It is contemplated that the entire assembly including the inner drive shaft 312, the outer drive shaft 314, and the outer sheath 256 may be used in conjunction with a guide catheter.

In another embodiment of the present invention, a lubricous or low friction coating 367, comprised of a fluoropolymer and the like, can be applied to the inner and/or outer surfaces of the inner drive shaft 312 and the inner and/or outer surfaces of outer drive shaft 314. This coating may improve trackability of the vascular material removal device 250, as well as to reduce friction between the drive shafts and between the outer drive shaft 314 and the outer sheath 256, and between the inner drive shaft 312 and the guidewire 288. The lubricous coating may be provided in the form of a sheath of a fluoropolymer which shrinks upon application. In this manner, the lubricous coating can reduce friction between the drive shafts, provide the drive shafts with increased torsional rigidity, limit radial expansion of the drive shafts, and form a fluid-tight lumen through the drive shafts. The coating can also aid proper aspiration through sheath 256 by minimizing friction between the drive shafts and occlusion material aspirated into sheath 256.

FIG. 28 is an expanded partial sectional side view of another embodiment of inner drive shaft 312. In this embodiment, a ribbon 368 is wound around inner helix 362 with a higher winding angle than that of inner helix 362. In one embodiment of the present invention, ribbon 368 has a rectangular cross section but it is recognized that any shape wire may be used. In the exemplary embodiment, ribbon 368 is wound in the same direction as inner helix 362 with a winding angle substantially the same or larger than the winding angle of inner helix 362. However, it is envisioned that ribbon 386 may have a winding angle substantially less than the winding angle of inner helix 362 or that ribbon 386 may be placed longitudinally between inner helix 362 and outer helix 360 thus having an effective wrapping angle of substantially 90 degrees. Ribbon 368 provides additional longitudinal strength to inner drive shaft 312. It is contemplated that ribbon 368 could be applied to outer drive shaft 314 in the same manner and that ribbon 368 could be wound in the opposite direction of the inner helix in either drive shaft configuration. Finally, it is contemplated that ribbon 368 could be wound around the outer helix of either inner drive shaft 312 and/or outer drive shaft 314.

It is contemplated that the inner drive shaft 312 and outer drive shaft 314 construction may comprise any number of coaxial helices to obtain similar drive characteristics. Furthermore, it is contemplated that any number of coaxial drive shafts can be employed in the expandable vascular material removal device 250.

The various embodiments of the present invention also provide a number of methods for performing intravascular treatments, such as removing or displacing vascular occlusion material. These methods comprise a plurality of steps, most of which have been discussed in detail with respect to embodiments 10, 142, 176 and 218, so the following discussion of the methods will simply supplement those detailed discussions, instead of restating them, where appropriate.

The present expandable intravascular occlusion material removal device is inserted into the patient's vascular system through a suitable puncture or other access site, such as via the femoral artery, in well known fashion. At this point, the expandable removal element 252 is in the radially contracted position. The removal device 252 can be inserted through a conventional guide catheter, well known to those having ordinary skill in the relevant art. The removal device 252 is moved over guidewire 288, which has been previously positioned in proximity to the intravascular treatment site, until the distal end of the distal tip 322 is adjacent the proximal end of the occlusion material to be removed thereby.

At any time, a fluid, such as saline, a drug therapy, heparinized saline, an oxygenated fluid, such as FLUORSOL, and the like, can be applied to the solution flush line 284. The fluid flows along the axial length of the drive shafts and passes into the hollow interior defined by the braided wires of removal element 252. At any time, another fluid to be infused into the patient, or a negative pressure to aspirate the intravascular treatment site may be applied to the solution flush line 284 from a suitable source.

With the expandable material removal element 252 being positioned with respect to the vascular occlusion material to be removed, the treating physician can expand the material removal element 252 to the desired degree by turning the actuation control knob 374. The controlled, analog expansion and contraction of the expandable removal element 252 can provide a treating physician with the most flexibility in performing intravascular treatments, as well as possibly reducing the costs of such treatments because multiple pieces of equipment need not be used. This is a significant improvement over some of the intravascular treatment devices of the prior art. In addition, the various constructions of the removal element radial expansion limiting means may insure that the removal element 252 is not over-expanded (see FIG. 8 and FIG. 9). In one exemplary embodiment of the radial expansion limiting means, the distal end of outer drive shaft 314 is extended a predetermined distance into the braid portion of removal element 252 such that the distal tip 322 of removal element 252 may engage the distal end of outer drive shaft 314 at a predetermined degree of radial expansion.

The removal device is now ready to remove vascular occlusion material from a vascular surface or from a vascular occlusion by rotation of the expandable material removal element 252. The treating physician actuates the control switch 278, thereby energizing the motor 274. The motor 274 induces rotation of the inner drive shaft 312 and the outer drive shaft 314, which, in turn, causes the removal element to rotate. The rotation of the material removal element 252 enables the sharp edges or abrasive particles on the surfaces of the braided wires to cut, abrade, ablate, or otherwise remove vascular occlusion material from a vascular lumen surface or a vascular occlusion. The physician then loosens slide lock 376 and begins to slide the advancement control housing 382 proximally thus causing both the inner drive shaft 312 and the outer drive shaft 314, and therefore the removal element 252, to move conjointly in the proximal direction. As the removal element 252 is moved proximally, it engages more occlusion material. The physician continually monitors an analog torque signal, for example a variable tone or LED lights on the drive housing, which indicate to the physician the torque provided by the motor at any given time. The removal element is advanced through the occlusion material at a given expanded position. Once clear of the distal side of the occlusion material, the physician will then rotate the actuation control knob 374 to increase the expansion of the removal element 252, and proceed to advance the removal element through the occlusion material again. This process is continued until a substantial portion of the occlusion material is removed.

This description of the method for using the exemplary embodiment or the present invention is only supplemental to those methods already disclosed. It is contemplate that the methods disclosed previously do apply to the present exemplary embodiment.

While preferred embodiments of the present invention are shown and described, it is envisioned that those skilled in the art may devise various modifications of the embodiments of the present invention without departing from the spirit and scope of the appended claims.

What is claim is:

1. A vascular occlusion material removal device for removing vascular occlusion material in a vascular lumen, comprising:
    a removal element having a proximal end and a distal end, and having a surface and an abrasive coating disposed thereon; and
    a distal tip located at said distal end of said removal element, said distal tip having a surface being less abrasive than said surface of said removal element having an abrasive coating, wherein said abrasive surface of said removal element is comprised of a plurality of strands which are braided together wherein each one of said plurality of strands comprises at least one wire.

2. A vascular occlusion material removal device according to claim 1 wherein the removal element is expandable and moves between a contracted position and an expanded position to allow said removal element to engage said vascular occlusion material within said vascular lumen.

3. A vascular occlusion material removal device according to claim 2 wherein a diameter of said removal element at said abrasive surface when said removal element is in said contracted position is equal to or less than a diameter of said distal tip.

4. A vascular occlusion material removal device according to claim 3 wherein said diameter of said removal element at said abrasive surface is measured at a location approximately equidistant between said proximal end and said distal end of said removal element.

5. A vascular occlusion material removal device according to claim 4 further comprising a proximal tip located at said proximal end of said removal element, said proximal tip having a surface being less abrasive than said removal element.

6. A vascular occlusion material removal device according to claim 5 wherein said diameter of said removal element at said abrasive surface when said removal element is in said contracted position is equal to or less than a diameter of said proximal tip.

7. A vascular occlusion material removal device according to claim 6 further comprising:
    an outer drive shaft operatively coupled to said proximal tip to provide torque thereto; and
    an inner drive shaft disposed through said removal element and operatively coupled to said distal tip, said inner drive shaft being shiftable within said removal element and said outer drive shaft, said inner drive shaft being shifted with respect to said removal element to expand said removal element from said contracted position to said expanded position.

8. A vascular occlusion material removal device according to claim 2 wherein said surface of said distal tip is smooth.

9. A vascular occlusion material removal device according to claim 1 wherein said at least one wire used in said plurality of strands is coated with an abrasive material.

10. A vascular occlusion material removal device according to claim 1 wherein said plurality of strands are each wrapped circumferentially with at least one wrapping wire.

11. A vascular occlusion material removal device according to claim 10 wherein an abrasive material is deposited on said at least one wrapping wire.

12. A vascular occlusion material removal device according to claim 1 wherein said plurality of strands have a diameter which is equal to or less than a diameter of said distal tip when said removal element is in said contracted position.

* * * * *

UNITED STATES PATENT AND TRADEMARK OFFICE
CERTIFICATE OF CORRECTION

PATENT NO. : 5,897,567
DATED : April 27, 1999
INVENTOR(S) : Ressemann et al.

It is certified that error appears in the above-identified patent and that said Letters Patent is hereby corrected as shown below:

Column 51, line 33, delete "arc", insert --are--.

Signed and Sealed this

Sixth Day of June, 2000

Attest:

Q. TODD DICKINSON

*Attesting Officer*  *Director of Patents and Trademarks*